(12) United States Patent
Inoue et al.

(10) Patent No.: US 8,247,086 B2
(45) Date of Patent: Aug. 21, 2012

(54) ORGANOMETALLIC COMPLEX AND LIGHT-EMITTING ELEMENT, LIGHT-EMITTING DEVICE AND ELECTRONIC DEVICE USING THE SAME

(75) Inventors: Hideko Inoue, Kanagawa (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1183 days.

(21) Appl. No.: 11/607,649

(22) Filed: Dec. 1, 2006

(65) Prior Publication Data
US 2007/0129545 A1 Jun. 7, 2007

(30) Foreign Application Priority Data
Dec. 5, 2005 (JP) .................. 2005-350807

(51) Int. Cl.
*H01L 51/54* (2006.01)
*C09K 11/06* (2006.01)
(52) U.S. Cl. . 428/690; 428/917; 313/504; 257/E51.044; 544/225
(58) Field of Classification Search .......... None
See application file for complete search history.

(56) References Cited

U.S. PATENT DOCUMENTS

| | | | |
|---|---|---|---|
| 5,484,922 A * | 1/1996 | Moore et al. ............ | 546/7 |
| 6,780,528 B2 | 8/2004 | Tsuboyama et al. | |
| 6,821,646 B2 | 11/2004 | Tsuboyama et al. | |
| 6,953,628 B2 | 10/2005 | Kamatani et al. | |
| 7,094,477 B2 | 8/2006 | Kamatani et al. | |
| 7,147,935 B2 | 12/2006 | Kamatani et al. | |
| 7,220,495 B2 | 5/2007 | Tsuboyama et al. | |
| 7,527,879 B2 | 5/2009 | Kamatani et al. | |
| 7,544,426 B2 | 6/2009 | Kamatani et al. | |
| 7,569,692 B2 | 8/2009 | Nii et al. | |
| 7,589,203 B2 | 9/2009 | Stössel et al. | |
| 7,687,155 B2 | 3/2010 | Kamatani et al. | |
| 7,709,100 B2 | 5/2010 | Kwong et al. | |
| 7,883,785 B2 | 2/2011 | Stossel et al. | |
| 7,960,038 B2 | 6/2011 | Ohsawa et al. | |
| 2001/0019782 A1* | 9/2001 | Igarashi et al. ............. | 428/690 |
| 2002/0063516 A1 | 5/2002 | Tsuboyama et al. | |
| 2002/0121638 A1 | 9/2002 | Grushin et al. | |
| 2003/0059646 A1* | 3/2003 | Kamatani et al. ............ | 428/690 |
| 2005/0025996 A1 | 2/2005 | Tsuboyama et al. | |
| 2005/0221123 A1 | 10/2005 | Inoue et al. | |
| 2006/0127696 A1 | 6/2006 | Stossel et al. | |
| 2006/0177694 A1 | 8/2006 | Kamatani et al. | |
| 2006/0228583 A1 | 10/2006 | Kamatani et al. | |
| 2007/0154733 A1 | 7/2007 | Fukuoka et al. | |
| 2007/0170843 A1 | 7/2007 | Kawamura et al. | |
| 2007/0212570 A1 | 9/2007 | Kamatani et al. | |
| 2007/0216294 A1 | 9/2007 | Kamatani et al. | |
| 2009/0015143 A1 | 1/2009 | Inoue et al. | |
| 2009/0174324 A1 | 7/2009 | Nii et al. | |
| 2009/0184634 A1 | 7/2009 | Kamatani et al. | |

FOREIGN PATENT DOCUMENTS

| | | |
|---|---|---|
| CN | 1478372 A | 2/2004 |
| CN | 1678617 A | 10/2005 |
| EP | 1 191 612 | 3/2002 |
| EP | 1 191 614 A2 | 3/2002 |
| EP | 1 348 711 A1 | 10/2003 |
| EP | 1 349 435 A1 | 10/2003 |
| EP | 1 722 602 A1 | 11/2006 |
| EP | 1 722 605 A1 | 11/2006 |
| EP | 1 881 050 A2 | 1/2008 |
| EP | 1 889 891 A2 | 2/2008 |
| JP | 48-8788 A | 2/1973 |
| JP | 2002-105055 A | 4/2002 |
| JP | 2002-175884 A | 6/2002 |
| JP | 2003-081988 | 3/2003 |
| JP | 2005-251639 | 9/2005 |
| JP | 2005-314414 | 11/2005 |
| WO | WO 02/45466 A1 | 6/2002 |
| WO | WO 2004/037836 A1 | 5/2004 |
| WO | WO 2004/108857 A1 | 12/2004 |

(Continued)

OTHER PUBLICATIONS

Zhang, Guo-Lin et al, Gaodeng Xuexiao Huaxue Xuebao (2004), vol. 25, No. 3, pp. 397-400 (with English abstract), Chemical Journal of Chinese Universities.
International Search Report (Application No. PCT/JP2006/323882), dated Jan. 16, 2007.
Written Opinion (Application No. PCT/JP2006/323882), dated Jan. 16, 2007.
Tsutsui, T. et al., "High Quantum Efficiency in Organic Light-Emitting Devices with Iridium-Complex as a Triplet Emissive Center," Japanese Journal of Applied Physics, vol. 38, No. 12B, Dec. 15, 1999, pp. L1502-L1504.

(Continued)

*Primary Examiner* — Marie R. Yamnitzky
(74) *Attorney, Agent, or Firm* — Husch Blackwell LLP

(57) ABSTRACT

An organometallic complex having a structure represented by the general formula (G1) is synthesized and applied to a light-emitting element.

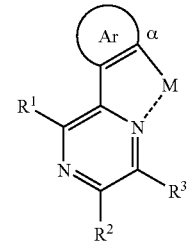

(G1)

In the formula, $R^1$ represents either an alkyl group having 1 to 4 carbon atoms, an alkoxy group having 1 to 4 carbon atoms, or an alkoxycarbonyl group having 1 to 5 carbon atoms; $R^2$ and $R^3$ each show either hydrogen or an alkyl group 1 to 4 carbon atoms; Ar represents an arylene group having 6 to 25 carbon atoms; M is a center metal selected from Group 9 element and Group 10 element.

35 Claims, 18 Drawing Sheets

FOREIGN PATENT DOCUMENTS

| | | |
|---|---|---|
| WO | WO 2005/086540 A1 | 9/2005 |
| WO | WO 2005/115061 | 12/2005 |

OTHER PUBLICATIONS

O'Brien, D.F. et al., "Improved Energy Transfer in Electrophosphorescent Devices," Applied Physics Letters, vol. 74, No. 3, Jan. 18, 1999, pp. 442-444.

Baldo, M.A. et al., "High-Efficiency Fluorescent Organic Light-Emitting Devices Using a Phosphorescent Sensitizer," Nature, vol. 403, Feb. 17, 2000, pp. 750-753.

Tsutsui, T. "Mechanism of Organic EL Element and Luminous Efficiency," Textbook of the 3rd Seminar at Division of Organic Molecular Electronics and Bioelectronics, 1993, pp. 31-37, Division of Molecular Electronics and Bioelectronics, The Japan Society of Applied Physics.

Thompson, M.E. et al., "Phosphorescent Materials and Devices," Proceedings of the 10th International Workshop on Inorganic and Organic Electroluminescence (EL'00), Dec. 4, 2000, pp. 35-38.

Duan, J.-P. et al., "New Iridium Complexes as Highly Efficient Orange-Red Emitters in Organic Light-Emitting Diodes," Advanced Materials, vol. 15, No. 3, Feb. 5, 2003, pp. 224-228.

Zhang, G.-L. et al, "Synthesis and Phosphorescence Property of a New Pyrazine Iridium(III) Complex," Acta Phys.-Chim. Sin., vol. 19, No. 10, 2003, pp. 889-891(with English translation).

Steel, P.J. et al., "Cyclometallated Compounds v. Double Cyclopalladation of Diphenyl Pyrazines and Related Ligands," Journal of Organometallic Chemistry, vol. 395, No. 3, 1990, pp. 359-373.

Slater, J.W. et al., "Cyclometallated Nitrogen Heterocycles," Journal of Organometallic Chemistry, vol. 688, Aug. 29, 2003, pp. 112-120.

International Search Report re Application No. PCT/JP2006/305474, Dated Apr. 11, 2006.

Written Opinion re Application No. PCT/JP2006/305474, Dated Apr. 11, 2006.

Shavaleev, N.M. et al., "Sensitized Near-Infrared Emission from Complexes of YB III, ND III, and ER III by Energy-Transfer from Covalently Attached PT II—Based Antenna Units," Chemistry—A European Journal, vol. 9, No. 21, 2003, pp. 5283-5291.

Usyatinsky, A. Ya., et al, "Microwave-Assisted Synthesis of Substituted Imidazoles on a Solid Support Under Solvent-Free Conditions,"Tetrahedron Letters, vol. 41, No. 26, 2000, pp. 5031-5034.

Kidwai, M. et al, "Microwave Assisted Synthesis of Novel 1,2,4-Triazines in 'Dry Media'," Synthetic Communications, vol. 31, No. 11, 2001, pp. 1639-1645.

Konno, H. et al,"Selective One-Pot Synthesis of Facial Tris-Ortho-Metalated Iridium(III) Complexes Using Microwave Irradiation," Chemistry Letters, vol. 32, No. 3, 2003, pp. 252-253.

European Search Report re application No. EP 07005200.6, dated Jul. 23, 2007.

Office Action re U.S. Appl. No. 11/092,816, dated May 20, 2010.

European Search Report re application No. EP 06715702.4, dated Jul. 23, 2010.

Declaration of Satoshi Seo, filed in U.S. Appl. No. 11/092,816, dated Sep. 21, 2010.

Office Action re Chinese application No. CN 200680045339.7, dated Feb. 24, 2011 (with English translation).

Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with full English translation).

Yersin, H. et al, "Triplet Emitters for Organic Light-Emitting Diodes: Basic Properties," *Highly Efficient OLEDs with Phosphorescent Materials*, Wiley-VCH Verlag GmbH & Co. KGaA, 2008, pp. 1-18.

Office Action re Chinese application No. CN 200710087859.0, dated Mar. 2, 2011 (with English translation).

Office Action re European application No. EP 06715702.4, dated Jun. 24, 2011.

Inoue, H. et al, *Basic Chemistry Course Photochemistry I* (Maruzen Co., Ltd.), pp. 106-110, "A Reaction of Singlet Oxygen with an Unsaturated Organic Molecule, 6.1.4, Quencher and Photosensitizer", Sep. 30, 1999.

* cited by examiner

ORGANOMETALLIC COMPLEX AND LIGHT-EMITTING ELEMENT, LIGHT-EMITTING DEVICE AND ELECTRONIC DEVICE USING THE SAME

TECHNICAL FIELD

The present invention relates to an organometallic complex. In particular, the present invention relates to an organometallic complex that is capable of converting a triplet excited state into luminescence. In addition, the present invention relates to a light-emitting element, a light-emitting device and an electronic device which use the organometallic complex.

BACKGROUND ART

Organic compounds are brought into an excited state by absorbing light. By going through this excited state, various reactions (such as photochemical reactions) are caused in some cases, or luminescence is produced in some cases. Therefore, various applications of the organic compounds have been being made.

As one example of the photochemical reactions, a reaction (oxygen addition) of singlet oxygen with an unsaturated organic molecule is known (refer to Reference 1: Haruo INOUE, et al., Basic Chemistry Course PHOTOCHEMISTRY I (Maruzen Co., Ltd.), pp. 106-110, for example). Since the ground state of an oxygen molecule is a triplet state, oxygen in a singlet state (singlet oxygen) is not generated by a direct photoexcitation. However, in the presence of another triplet-excited molecule, singlet oxygen is generated to achieve an oxygen addition reaction. In this case, a compound that is capable of forming the triplet excited molecule is referred to as a photosensitizer.

As described above, in order to generate singlet oxygen, a photosensitizer that is capable of forming a triplet excited molecule by photoexcitation is necessary. However, since the ground state of an ordinary organic compound is a singlet state, photoexcitation to a triplet excited state is a forbidden transition, and a triplet excited molecule is unlikely to be generated. Therefore, as such a photosensitizer, a compound in which intersystem crossing from the singlet excited state to the triplet excited state easily occurs (or a compound in which the forbidden transition of photoexcitation directly to the triplet excited state is allowed) is required. In other words, such a compound can be used as a photosensitizer, and is useful.

Also, such a compound often discharges phosphorescence. The phosphorescence is luminescence generated by transition between different energies in multiplicity and, in the case of an ordinary organic compound, indicates luminescence generated in returning from the triplet excited state to the singlet ground state (in contrast, luminescence in returning from a singlet excited state to a singlet ground state is referred to as fluorescence). Application fields of a compound that is capable of discharging phosphorescence, that is, a compound that is capable of converting a triplet excited state into luminescence (hereinafter, referred to as a phosphorescent compound), include a light-emitting element using an organic compound as a luminescent substance.

This light-emitting element has a simple structure in which a light-emitting layer including an organic compound that is a luminescent substance is provided between electrodes. This light-emitting element is a device attracting attention as a next-generation flat panel display element in terms of characteristics such as being thin and light in weight, high speed response, and direct current low voltage driving. In addition, a display device using this light-emitting element is superior in contrast, image quality, and wide viewing angle.

The emission mechanism of a light-emitting element in which an organic compound is used as a luminescent substance is a carrier injection type. Namely, by applying a voltage with a light-emitting layer interposed between electrodes, electrons and holes injected from electrodes are recombined to make the luminescent substance excited, and light is emitted when the excited state returns to a ground state. As the type of the excited state, as in the case of photoexcitation described above, a singlet excited state (S*) and a triplet excited state (T*) are possible. Further, the statistical generation ratio thereof in a light-emitting element is considered to be S*:T*=1:3.

As for a compound capable of converting a singlet excited state to luminescence (hereinafter, fluorescent compound), luminescence from a triplet excited state (phosphorescence) is not observed but luminescence from a singlet excited state (fluorescence) only is observed at a room temperature. Accordingly, the internal quantum efficiency (the ratio of generated photons to injected carriers) in a light-emitting element using a fluorescent compound is assumed to have a theoretical limit of 25% based on S*:T*=1:3.

On the other hand, when the phosphorescent compound described above is used, the internal quantum efficiency can be improved to 75 to 100% in theory. Namely, a luminous efficiency that is 3 to 4 times as much as that of the fluorescence compound can be achieved. For these reasons, in order to achieve a high efficient light-emitting element, a light-emitting element using a phosphorescent compound has been developed actively (for example, Reference 2: Zhang, Guo-Lin, et al., Gaodeng Xuexiao Huaxue Xuebao (2004), vol.25, No. 3, pp. 397-400). In particular, as the phosphorescent compound, an organometallic complex using iridium or the like as a center metal has been attracting attention, due to its high phosphorescence quantum yield.

DISCLOSURE OF INVENTION

The organometallic complex disclosed in Reference 2 can be expected to be used as a photosensitizer, since it easily causes intersystem crossing. In addition, since the organometallic complex easily generates luminescence (phosphorescence) from a triplet excited state, a high efficient light-emitting element is expected by using the organometallic complex for the light-emitting element. However, in the present state, the number of types of such organometallic complexes is small.

For example, a pyrazine derivative which is used as a ligand of the organometallic complex disclosed in Reference 2 is synthesized by a dehydration condensation reaction of ethylenediamine and α-diketone (benzyl) and a dehydrogenation reaction following the dehydration condensation reaction; however, there are limitations on the types of ethylenediamine derivatives and α-diketone which can be used as raw materials, and thus, the types of pyrazine derivatives are also limited. Therefore, naturally, there are also limitations on the types of organometallic complexes using the pyrazine derivative as a ligand.

Further, the organometallic complex disclosed in Reference 2 has a problem that the emission spectrum is broad. This lowers the color purity and thus, is disadvantageous for application to full color display devices in terms of color reproductively. This organometallic complex emits red-orange color light; however, if the emission spectrum is broad, the spectrum extends to a region of deep red to infrared, which leads to lower luminous efficiency (visibility efficiency (cd/A)).

The present invention has been made in view of the above problems. It is an object of the present invention to enrich variations of organometallic complexes which can emit phosphorescence by applying organometallic complexs which can be used for easily synthesizing various derivatives to a ligand. Further, it is another object of the present invention to provide an organometallic complex having a sharp emission spectrum. Moreover, it is still another object of the present invention to provide an organometallic complex having high luminous efficiency.

Moreover, it is another object of the present invention to provide a light-emitting element with wide variations of light emission of green to red colors by manufacturing a light-emitting element using such an organometallic complex. It is still another object of the present invention to provide a light-emitting element with high color purity. Further, it is another of the present invention to provide a light-emitting element having high luminous efficiency. Moreover, it is still another object of the present invention to provide a light-emitting device and an electronic device with lowered power consumption.

The present inventors have made researches keenly. As a result, the present inventors have invented that a pyrazine derivative represented by the following general formula (G0) is ortho metalated with a metal ion of Group 9 or Group 10, thereby obtaining an organometallic complex. In addition, the present inventors have also found that the organometallic complex having an ortho metalated structure of the general formula (G0) easily causes intersystem crossing, and can emit phosphorescence.

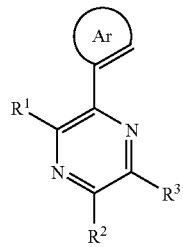

(G0)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ and $R^3$ each show any one of hydrogen and an alkyl group having 1 to 4 carbon atoms; and Ar represents an aryl group having 6 to 25 carbon atoms, and the aryl group may have an additional substitute(s).

Therefore, a structure of the present invention is an organometallic complex comprising a structure represented by a general formula (G1).

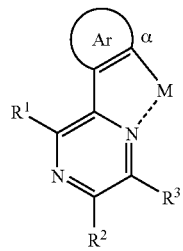

(G1)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ and $R^3$ each show any one of hydrogen and an alkyl group having 1 to 4 carbon atoms; Ar represents an arylene group having 6 to 25 carbon atoms and the arylene group may have an additional substitute(s); M is a center metal selected from Group 9 element and Group 10 element; and α represents a position of carbon which bonds the center metal in the arylene group.

In addition, when $R^3$ in the above general formula (G0) is hydrogen, the pyrazine derivative represented by the general formula (G0) is easy to be ortho metalated with a metal ion, since sterric hindrance is small, which is preferable in terms of yield in synthesis. Accordingly, a preferred structure of the present invention is an organometallic complex including a structure represented by the following general formula (G2).

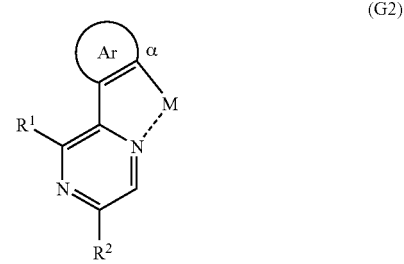

(G2)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ shows any one of hydrogen and an alkyl group having 1 to 4 carbon atoms; Ar represents an arylene group having 6 to 25 carbon atoms and the arylene group may have an additional substitute(s); M is a center metal selected from Group 9 element and Group 10 element; and a represents a position of carbon which bonds the center metal in the arylene group.

In the above general formula (G1) or (G2), the arylene (Ar) group is preferably a phenylene group. By introducing a substituent to the phenylene group, emission color with wide region of green color to red color can be realized. Therefore, a preferred structure of the present invention is an organometallic complex including a structure represented by the general formula (G3) or (G4). (G4) is more preferable in terms of yield in synthesis, in the same reason as (G2).

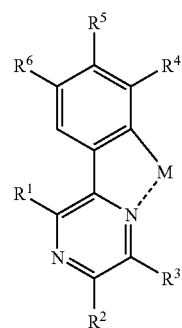

(G3)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ and $R^3$ each represent any one of hydrogen and an alkyl group having 1 to 4 carbon atoms; $R^4$ to $R^6$ each represent any one of hydrogen, an alkyl group having 1 to 4 carbon atoms, an alkoxy group having 1 to 4 carbon atoms, a halogen group, a trifluoromethyl group, an aryl group having 6 to 12 carbon atoms, a dialkylamino group having 2 to 8 carbon atoms, and a diarylamino group having 12 to 24 carbon atoms; and M is a center metal selected from Group 9 element and Group 10 element.

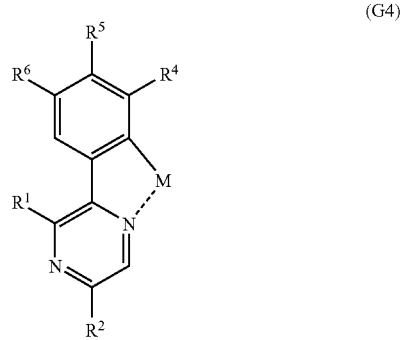

(G4)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ represents any one of hydrogen and an alkyl group having 1 to 4 carbon atoms; $R^4$ to $R^6$ each represent any one of hydrogen, an alkyl group having 1 to 4 carbon atoms, an alkoxy group having 1 to 4 carbon atoms, a halogen group, a trifluoromethyl group, an aryl group having 6 to 12 carbon atoms, a dialkylamino group having 2 to 8 carbon atoms, and a diarylamino group having 12 to 24 carbon atoms; and M is a center metal selected from Group 9 element and Group 10 element.

In addition, when $R^4$ and $R^6$ in the above general formula (G4) are hydrogen, the pyrazine derivative is more preferable in terms of yield in synthesis since sterric hindrance is small. Further, there is also advantageous effect that isomer is difficult to generate. Accordingly, a more preferred structure of the present invention is an organometallic complex including a structure represented by the following general formula (G5).

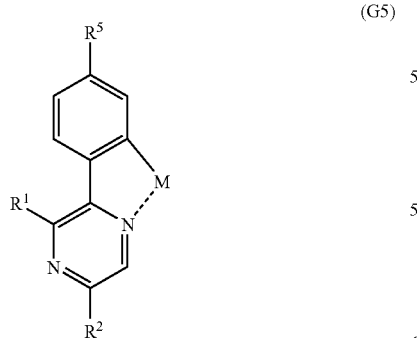

(G5)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ represents any one of hydrogen and an alkyl group having 1 to 4 carbon atoms; $R^5$ represents any one of hydrogen, an alkyl group having 1 to 4 carbon atoms, an alkoxy group having 1 to 4 carbon atoms, a halogen group, a trifluoromethyl group, an aryl group having 6 to 12 carbon atoms, a dialkylamino group having 2 to 8 carbon atoms, and a diarylamino group having 12 to 24 carbon atoms; and M is a center metal selected from Group 9 element and Group 10 element.

In addition, in the organometallic complex having the structure represented by the above general formula (G1) or (G2), conjugation of the arylene group (Ar) is expanded to obtain red emission color, which is useful. Accordingly, another structure of the present invention is an organometallic complex in which the arylene group in the organometallic complex having the structure of the above general formula (G1) or (G2) is represented by any one of the following formulas (G6) to (G9).

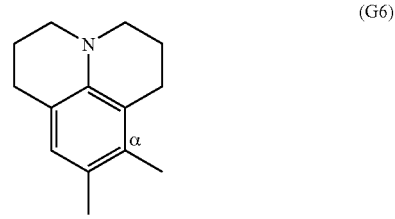

(G6)

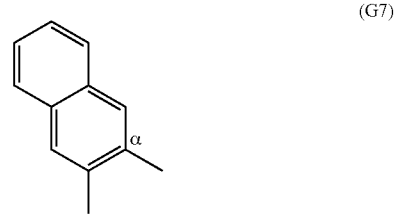

(G7)

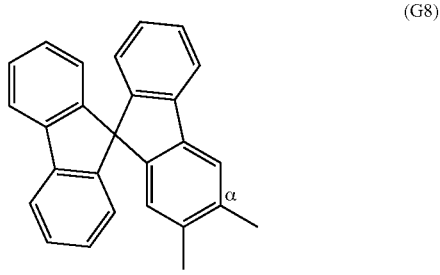

(G8)

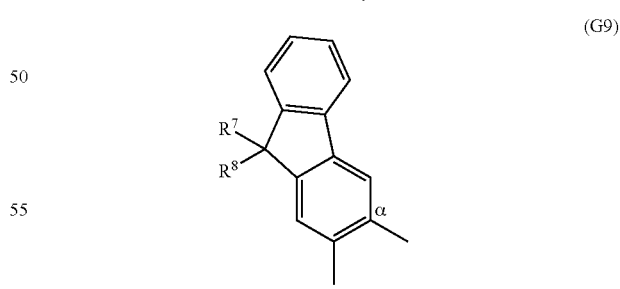

(G9)

In the formula, $R^7$ and $R^8$ represent an alkyl group having 1 to 4 carbon atoms, and a represents a position of carbon which bonds the center metal in the arylene group.

Here, as the organometallic complex having the structure represented by the general formula (G1), more specifically, an organometallic complex represented by the following general formula (G10) is preferable since it is easy to synthesize.

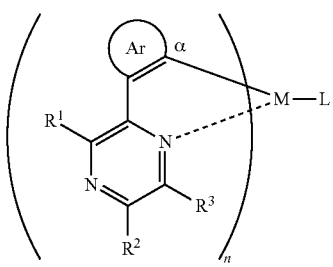

(G10)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ and $R^3$ each show any one of hydrogen and an alkyl group having 1 to 4 carbon atoms; Ar represents an arylene group having 6 to 25 carbon atoms and the arylene group may have an additional substitute(s); M is a center metal selected from Group 9 element and Group 10 element; α represents a position of carbon which bonds the center metal in the arylene group; L represents an monoanionic ligand; and n is 2 when the center metal is an element belonging to Group 9, and n is 1 when the center metal is an element belonging to Group 10.

Further, as the organometallic complex having the structure represented by the above general formula (G2), more specifically, an organometallic complex represented by the following general formula (G11) is preferable since it is easy to synthesize.

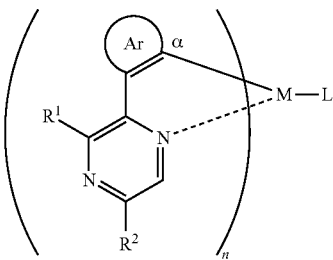

(G11)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ represents any one of hydrogen and an alkyl group having 1 to 4 carbon atoms; Ar represents an arylene group having 6 to 25 carbon atoms and the arylene group may have an additional substitute(s); M is a center metal selected from Group 9 element and Group 10 element; α represents a position of carbon which bonds the center metal in the arylene group; L represents an monoanionic ligand; and n is 2 when the center metal is an element belonging to Group 9, and n is 1 when the center metal is an element belonging to Group 10.

Further, as the organometallic complex having the structure represented by the above general formula (G3), more specifically, an organometallic complex represented by the following general formula (G12) is preferable since it is easy to synthesize.

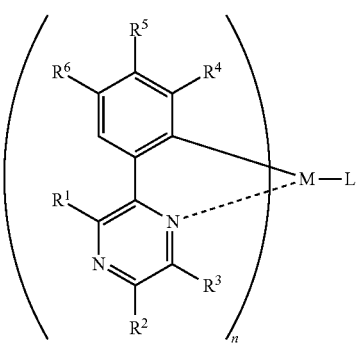

(G12)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ and $R^3$ each show any one of hydrogen and an alkyl group having 1 to 4 carbon atoms; $R^4$ to $R^6$ each represent any one of hydrogen, an alkyl group having 1 to 4 carbon atoms, an alkoxy group having 1 to 4 carbon atoms, a halogen group, a trifluoromethyl group, an aryl group having 6 to 12 carbon atoms, a dialkylamino group having 2 to 8 carbon atoms, and a diarylamino group having 12 to 24 carbon atoms; M is a center metal selected from Group 9 element and Group 10 element; L represents an monoanionic ligand; and n is 2 when the center metal is an element belonging to Group 9, and n is 1 when the center metal is an element belonging to Group 10.

Furthermore, as the organometallic complex having the structure represented by the above general formula (G4), more specifically, an organometallic complex represented by the following general formula (G13) is preferable since it is easy to synthesize.

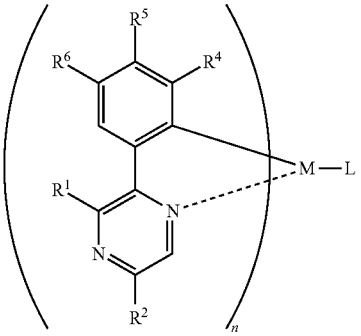

(G13)

In the formula, $R^1$ represents any one of an alkyl group having 1 to 4 carbon atoms, an alkoxy group having 1 to 4 carbon atoms, and an alkoxycarbonyl group having 1 to 5 carbon atoms; $R^2$ represents any one of hydrogen and an alkyl group having 1 to 4 carbon atoms; $R^4$ to $R^6$ each represent any one of hydrogen, an alkyl group having 1 to 4 carbon atoms, an alkoxy group having 1 to 4 carbon atoms, a halogen group, a trifluoromethyl group, an aryl group having 6 to 12 carbon atoms, a dialkylamino group having 2 to 8 carbon atoms, and a diarylamino group having 12 to 24 carbon atoms; M is a center metal selected from Group 9 element and Group 10 element; L represents an monoanionic ligand; and n is 2 when the center metal is an element belonging to Group 9, and n is 1 when the center metal is an element belonging to Group 10.

In addition, as the organometallic complex having the structure represented by the above general formula (G5), more specifically, an organometallic complex represented by the following general formula (G14) is preferable since it is easy to synthesize.

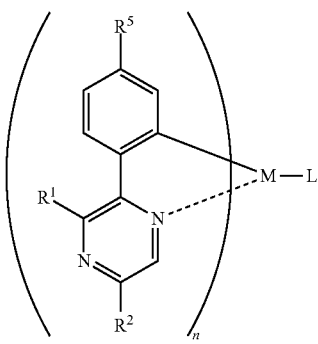

(G14)

In the formula, $R^1$ represents any one of an alkyl group having 1 to 4 carbon atoms, an alkoxy group having 1 to 4 carbon atoms, and an alkoxycarbonyl group having 1 to carbon atoms; R 2 represents any one of hydrogen and an alkyl group having 1 to 4 carbon atoms; $R^5$ represents any one of hydrogen, an alkyl group having 1 to 4 carbon atoms, an alkoxy group having 1 to 4 carbon atoms, a halogen group, a trifluoromethyl group, an aryl group having 6 to 12 carbon atoms, a dialkylamino group having 2 to 8 carbon atoms, and a diarylamino group having 12 to 24 carbon atoms; M is a center metal selected from Group 9 element and Group 10 element; L represents an monoanionic ligand; and n is 2 when the center metal is an element belonging to Group 9, and n is 1 when the center metal is an element belonging to Group 10.

In addition, in the organometallic complex represented by the above general formula (G10) or (G11), conjugation of the arylene group (Ar) is expanded to obtain red light emission, which is useful. Accordingly, another structure of the present invention is an organometallic complex in which the arylene group in the organometallic complex having the structure of the above general formula (G10) or (G11) is represented by any one of the following formulas (G6) to (G9).

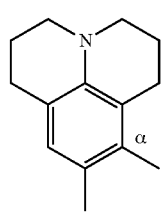

(G6)

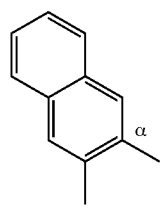

(G7)

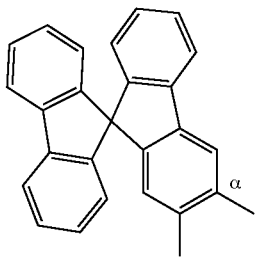

(G8)

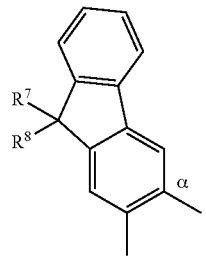

(G9)

In the formula, $R^7$ and $R^8$ represent an alkyl group having 1 to 4 carbon atoms, and α represents a position of carbon which bonds the center metal in the arylene group.

The above-mentioned monoanionic ligand L is preferably either a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen. More preferably, the monoanionic ligand L is a monoanionic ligand represented by the following structural formulas (L1) to (L8). Since these ligands have high coordinative ability and can be obtained at low price, they are useful.

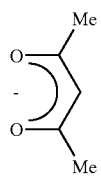

(L1)

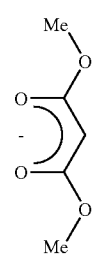

(L2)

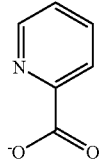

(L3)

-continued

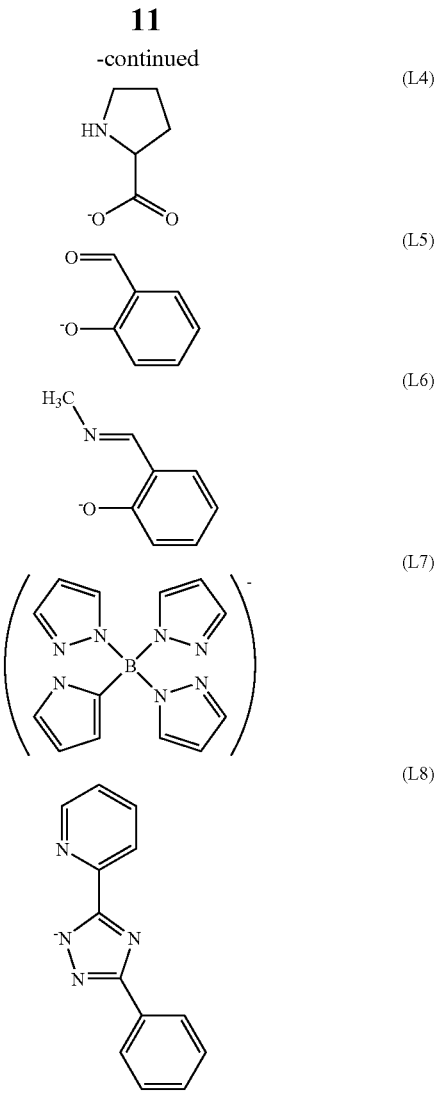

In order to emit phosphorescence more effectively, a heavy metal is preferable as a center metal in terms of heavy atom effect. Therefore, one feature of the present invention is that iridium or platinum is employed as the center metal M in each of the above organometallic complexes of the present invention.

In the organometallic complex including the structure represented by the above general formulas (G1) to (G5) (in other words, including the organometallic complexes represented by the above general formulas (G10) to (G14)), the coordinate structure in which the pyrazine derivative represented by the general formula (G0) is ortho metalated with a metal ion, contributes emission of phosphorescence greatly. Therefore, another structure of the present invention is a light-emitting material including an organic metallic complex as described above.

In addition, the organometallic complex of the present invention can emit phosphorescence. In other words, a triplet excited energy can be converted into light, and thus, high efficiency can be obtained by applying the organometallic complex to a light-emitting element. Thus, the organometallic complex of the present invention is very effective. Therefore, the present invention includes a light-emitting element using the organometallic complex of the present invention.

At this time, the organometallic complex of the present invention is effective when it is used for a luminescent substance in terms of luminous efficiency. Therefore, one feature of the present invention is a light-emitting element using the organometallic complex of the present invention as a luminescent substance.

The thus obtained light-emitting element of the present invention can realize a high luminous efficiency, and thus, a light-emitting device (such as an image display device or an emission device) using this light-emitting element can realize low power consumption. Accordingly, the present invention includes a light-emitting device, an electronic device, and the like using the light-emitting element of the present invention.

In this specification, the term "light-emitting device" refers to an image display device or a light-emitting device including a light-emitting element. Further, the category of the light-emitting device includes a module including a light-emitting element attached with a connector such as a module attached with an anisotropic conductive film, TAB (Tape Automated Bonding) tape, or a TCP (Tape Carrier Package); a module in which the top of the TAB tape or the TCP is provided with a printed wire board; or a module in which an IC (Integrated Circuit) is directly mounted on a light-emitting element by COG (Chip On Glass); and the like. Further, the category includes a light-emitting device used for lightning equipment and the like.

By carrying out the present invention, the variations of organometallic complexes which can emit phosphorescence can be enriched. Further, an organometallic complex having sharp emission spectrum can be provided. Moreover, an organometallic complex having high luminous efficiency can be provided.

Further, by manufacturing a light-emitting element using an organometallic complex of the present invention, a light-emitting element having wide variation of light emission of green to red colors can be provided. A light-emitting element having high color purity can be provided. Moreover, a light-emitting element having high luminous efficiency can be provided.

By using an organometallic complex of the present invention, a light-emitting device and an electronic device which have lowered power consumption can be provided.

BEST MODE FOR CARRYING OUT THE INVENTION

Embodiment Modes

Figure 1:
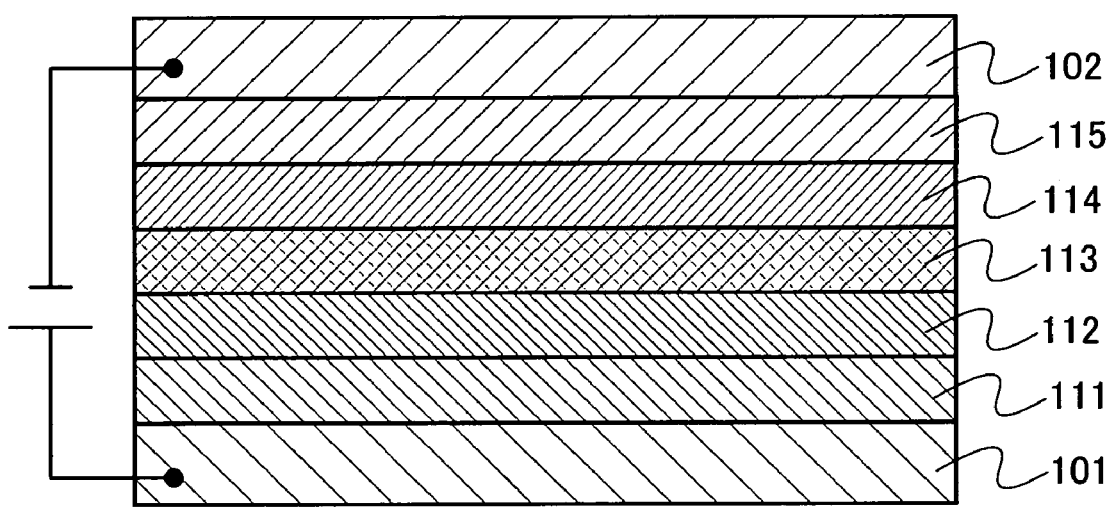
FIG. 1 shows a structure of a light-emitting element using an organometallic complex in accordance with an aspect of the present invention.

Embodiment Modes of the present invention will be described with reference to the drawings. The present invention can be carried out in many different modes without being limited to the description given below. It is easily understood by those skilled in the art that modes and details disclosed herein can be modified in various ways without departing from the spirit and the scope of the present invention. It should be noted that the present invention should not be interpreted as being limited to the description of the embodiment mode and examples given below.

Embodiment Mode 1

Embodiment Mode 1 will describe an organometallic complex in accordance with one feature of the present invention.
<Synthesis Method of a Pyrazine Derivative Represented by the General Formula (G0)>

An organometallic complex of the present invention is formed by ortho metalation of a pyrazine derivative represented by the following general formula (G0) with respect to a metal ion belonging to Group 9 or Group 10.

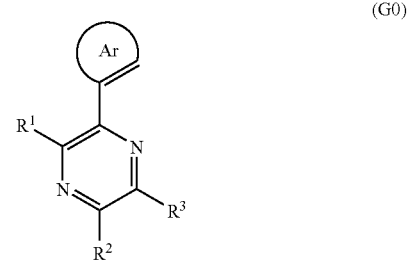

In the formula, R$^1$ represents either an alkyl group having 1 to 4 carbon atoms, an alkoxy group having 1 to 4 carbon atoms, or an alkoxycarbonyl group having 1 to 5 carbon atoms. In addition, R$^2$ and R$^3$ represent hydrogen or an alkyl group having 1 to 4 carbon atoms. Ar represents an aryl group having 6 to 25 carbon atoms, and further, the aryl group may have an additional substituent(s).

The pyrazine derivative represented by the general formula (G0) can be synthesized by a simple and easy synthesis scheme as shown below. For example, as shown in the following scheme (a), a halide of arene (A1) is lithiated with alkyllithium or the like, and is reacted with pyrazine (A2), thereby obtaining the pyrazine derivative. Alternatively, as shown in the scheme (a'), the pyrazine derivative can be obtained by coupling boronic acid of arene (A1') and halide of pyrazine (A2'). X in the formula denotes a halogen element.

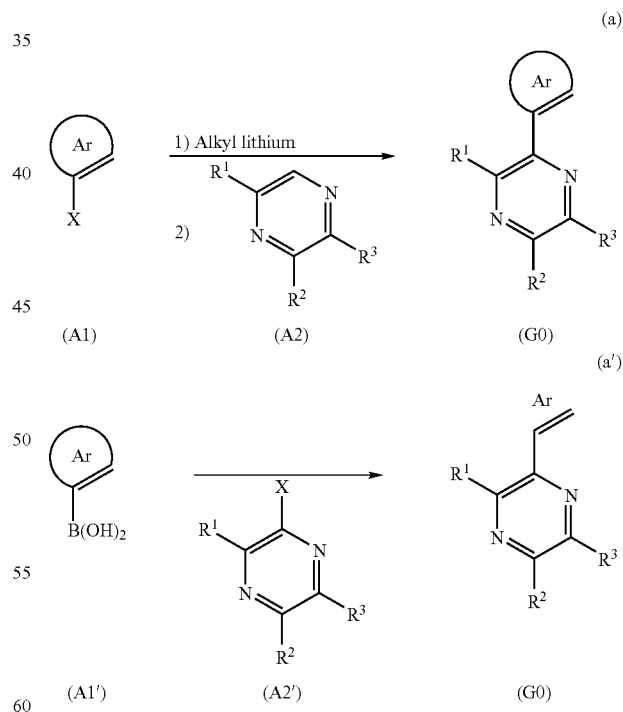

Various types of the above compounds (A1), (A2), (A1') and (A2') are commercially available or can be synthesized, and thus, a large number of types of the pyrazine derivative represented by the general formula (G0) can be synthesized. Accordingly, an organometallic complex of the present invention has a feature of wide variations of a ligand.

<Synthesis Method of an Organometallic Complex of the Present Invention having a Structure Shown by the General Formula (G1)>

Next, an organometallic complex of the present invention which is formed by ortho metalation of the pyrazine derivative represented by (G0), i.e., the organometallic complex having the structure represented by the following general formula (G1) will be described.

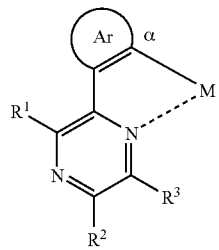

(G1)

In the formula, $R^1$ represents either an alkyl group having 1 to 4 carbon atoms, an alkoxy group having 1 to 4 carbon atoms, or an alkoxycarbonyl group having 1 to 5 carbon atoms. $R^2$ and $R^3$ represent hydrogen or an alkyl group having 1 to 4 carbon atoms. Ar represents an arylene group having 6 to 25 carbon atoms, and the arylene group may have an additional substituent(s). M is a center metal, and denotes an element belonging to Group 9 or Group 10. α represents a position of carbon which bonds the center metal in the arylene group.

First, as shown in the synthesis scheme (b), the pyrazine derivative represented by the general formula (G0) and a compound of a metal belonging to Group 9 or Group 10 and including halogen (such as a metal halide or metal complex) are heated in an appropriate solvent, thereby obtaining a dinuclear complex (B) which is a kind of organometallic complexes of the present invention and which has the structure represented by the general formula (G1). As a compound including a metal belonging to Group 9 or Group 10, and including halogen, there are given rhodium chloride hydrate, palladium chloride, iridium chloride hydrate, iridium chloride hydrate hydrochloride, potassium tetrachloroplatinate (II), and the like; however, the present invention is not limited to these examples. In the scheme (b), M denotes an element belonging to Group 9 or Group 10, and X denotes a halogen element. α represents a position of carbon which bonds the center metal in the arylene group Ar. In addition, n is 2 when M is an element belonging to Group 9, and n is 1 when M is an element belonging to Group 10.

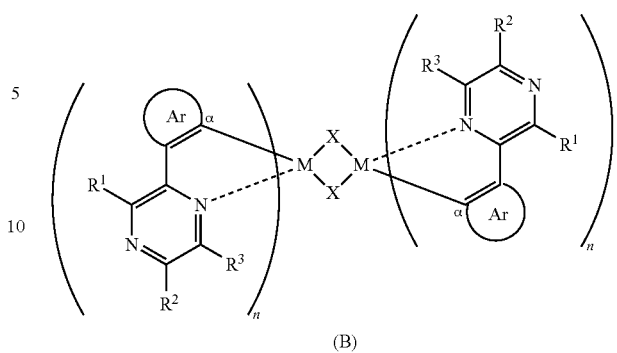

(B)

Further, as shown by the following synthesis scheme (c'), the dinuclear complex (B) and the pyrazine derivative represented by the general formula (G0) are heated at a high temperature of about 200° C. in a high boiling solvent of glycerol or the like, and thus, one type (C') of organometallic complexes of the present invention including the structure represented by the general formula (G1) can be obtained. As shown in the synthesis scheme (c"), a dinuclear complex (B) and a compound which can be ortho metalated, such as phenylpyridine (more typically, a compound which can be cyclometalated) are heated at a high temperature of around 200° C. in a high boilingsolvent of glycerol or the like, and thus, one type (C") of organometallic complexes of the present invention including the structure represented by the general formula (G1) can be obtained. In the schemes (c') and (c"), M denotes an element belonging to Group 9 or Group 10, and X denotes a halogen element. α represents a position of carbon which is bound to the center metal M in the arylene group Ar. In addition, n is 2 when M is an element belonging to Group 9, and n is 1 when M is an element belonging to Group 10.

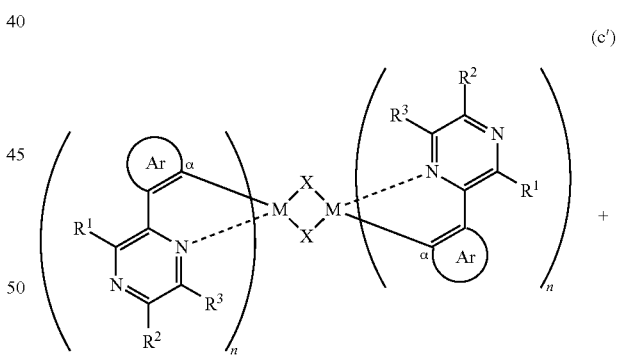

(c')

Compound including a metal belonging to Group 9 or Group 10 and including halogen + 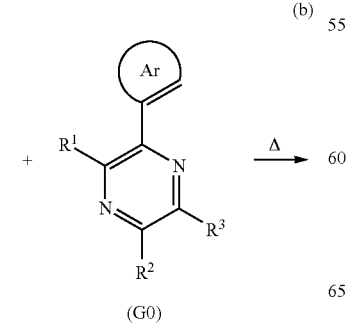 $\xrightarrow{\Delta}$ (G0)

2 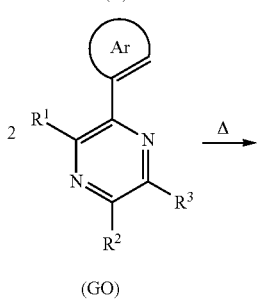 $\xrightarrow{\Delta}$ (G0)

(b)

(B)

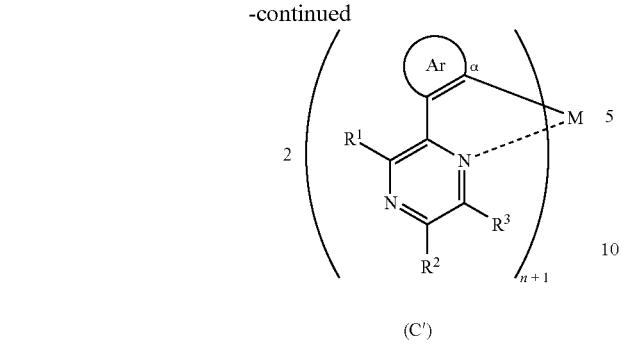

(C')

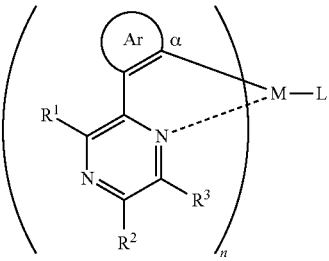

(G10)

In the formula, $R^1$ represents either an alkyl group having 1 to 4 carbon atoms, an alkoxy group having 1 to 4 carbon atoms, or an alkoxycarbonyl group having 1 to 5 carbon atoms. R and $R^3$ represent hydrogen or an alkyl group having 1 to 4 carbon atoms. Ar represents an arylene group having 6 to 25 carbon atoms, and the arylene group may have an additional substituent(s). M is a center metal, and denotes an element belonging to Group 9 or Group 10. α represents a position of carbon which bonds the center metal in the arylene group. L denotes a monoanionic ligand. In addition, n is 2 when M is an element belonging to Group 9, and n is 1 when M is an element belonging to Group 10.

The organometallic complex of the present invention represented by the general formula (G10) can be synthesized by the following scheme (c). In other words, the dinuclear complex (B) obtained by the above scheme (b) is reacted with a material HL of a monoanionic ligand, and a proton of HL is eliminated and coordinated to the central metal M. In this manner, an organometallic complex of the present invention represented by the general formula (G10) can be obtained. In the schemes (c), M denotes an element belonging to Group 9 or Group 10, and X denotes a halogen element. α represents a position of carbon which bonds the center metal M in the arylene group Ar. In addition, n is 2 when M is an element belonging to Group 9, and n is 1 when M is an element belonging to Group 10.

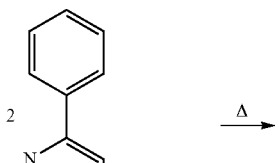

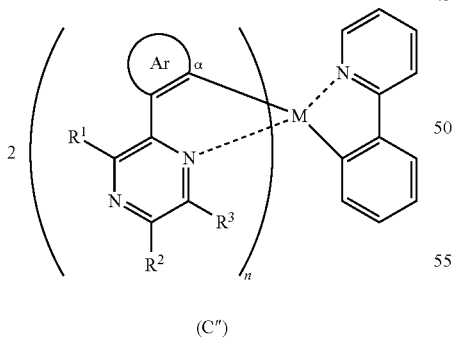

(C")

<Synthesis Method of an Organometallic Complex of the Present Invention Represented by the General Formula (G10)>

A most preferable example, i.e., an organometallic complex represented by the general formula (G10), among organometallic complexes having the structure represented by the above general formula (G1), will be described.

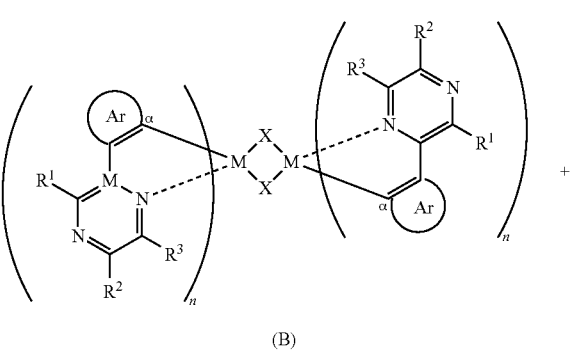

(B)

(c)

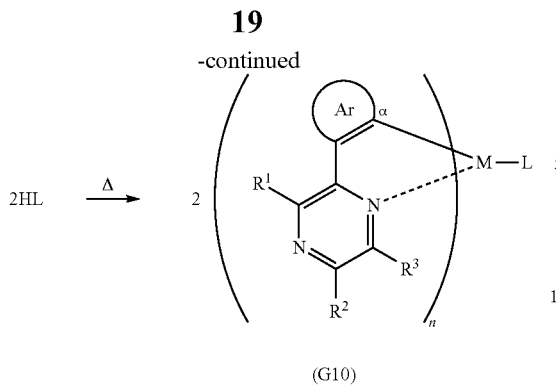

(G10)

<Specific Structural Formulas of the Organometallic Complex of the Present Invention having a Structure Shown by the General Formula (G1), and the Organometallic Complex of the Present Invention Represented by the General Formula (G10)>

Then, specific structural formulas of the organometallic complex of the present invention having the structure shown by the general formula (G1), and the organometallic complex of the present invention represented by the general formula (G10) will be described.

The center metal M is selected from elements belonging to Group 9 or Group 10; however, iridium(III) or platinum(II) is preferable in terms of luminous efficiency. In particular, when iridium(III) is preferably used, since it is thermally stable.

Then, a ligand portion P surrounded by the broken line in the general formulas (G1) and (G10) will be described. As described above, M denotes an element belonging to Group 9 or Group 10. α represents a position of carbon which bonds the center metal in the arylene group. L denotes a monoanionic ligand (specific examples are described below). In addition, n is 2 when M is an element belonging to Group 9, and n is 1 when M is an element belonging to Group 10.

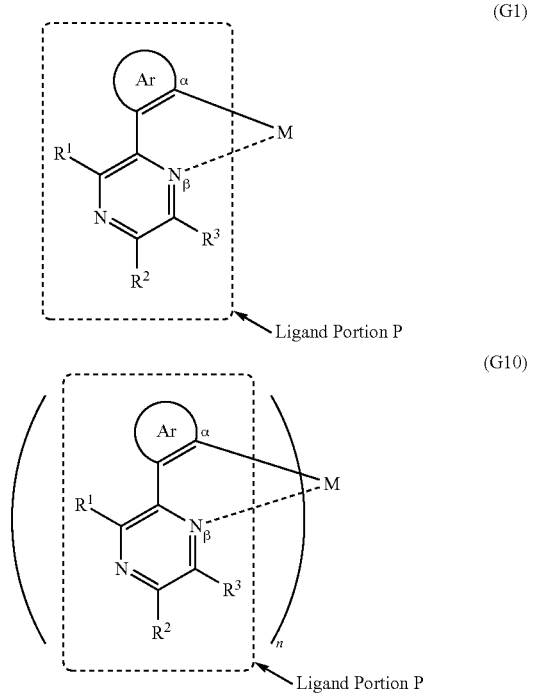

As specific examples of $R^1$, an alkyl groups such as a methyl group, an ethyl group, an isopropyl group, or an n-butyl group; an alkoxy group such as a methoxy group, an ethoxy group, an isopropoxy group, or an n-butoxy group; or an alkoxycarbonyl group such as a methoxycarbonyl group, an ethoxycarbonyl group, an isopropoxycarbonyl group, or an n-butoxycarbonyl group are given. By adopting these substituents to $R^1$, a synthesis yield of an organometallic complex can be more enhanced than when $R^1$ is hydrogen. As compared with when a conjugated group (such as a phenyl group) is used for $R^1$, emission spectrum can be more sharpened and thus, color purity can be increased.

As specific examples of $R^2$ and $R^3$, an alkyl group typified by a methyl group, an ethyl group, an isopropyl group, an n-butyl group or the like can be used as well as hydrogen.

As specific examples of Ar, a phenylene group, a phenylene group substituted by an alkyl group such as a metyl group, a phenylene group substituted by an alkoxy group such as a methoxy group, a phenylene group substituted by a hologen group such as a fluoro group, a phenylene group substituted by a trifluorometyl group, a phenylene group substituted by a phenyl group, a phenylene group substituted by a dialkylamino group such as a dimethylamino group, a phenylene group substituted by a diarylamino group such as a diphenylamino group are given. In particular, by using a phenylene group substituted by a halogen group or a trifluoromethyl group for Ar, emission wavelength can be shifted to a shorter wavelength than when an unsubstituted phenylene group is used for Ar. By using a phenylene group substituted by a dialkylamino group or a diarylamino group for Ar, emission wavelength can be shifted to a longer wavelength than when an unsubstituted phenylene group is used for Ar. Moreover, as Ar, a julolidylene group, a naphthylene group, a spiro fluorene-diyl group, a 9,9-dialkylfluorene-diyl group such as a 9,9-dimethylfluorene-diyl group can be applied. In that case, emission wavelength can be shifted to a longer wavelength side than when Ar adopts an unsubstituted phenylene group.

As the structure of a ligand portion P in the above general formulas (G0) and (G10), more specifically, any structure of ligand groups 1 to 7 below can be applied. However, the present invention is not limited to these ligand groups. α denotes a position of carbon which is bound to the center metal M. β denotes a position of nitrogen which is coordinated to the center metal M.

ligand group 1

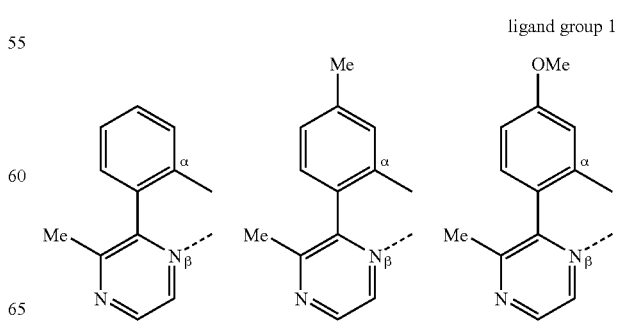

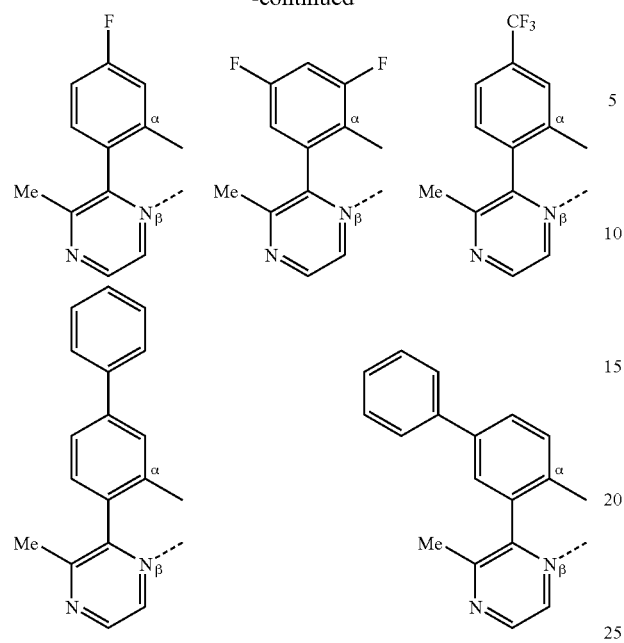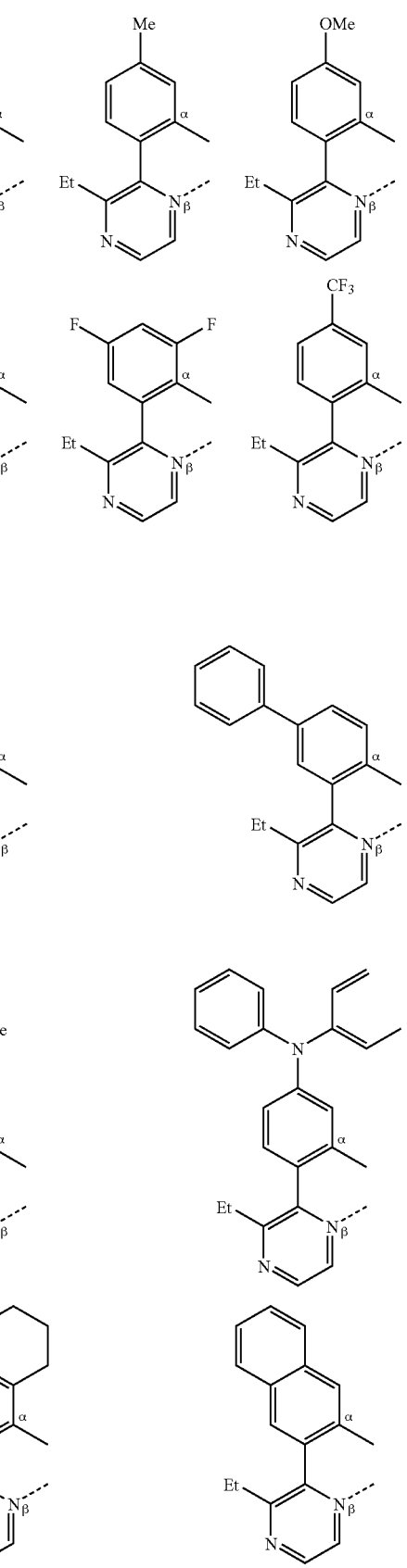

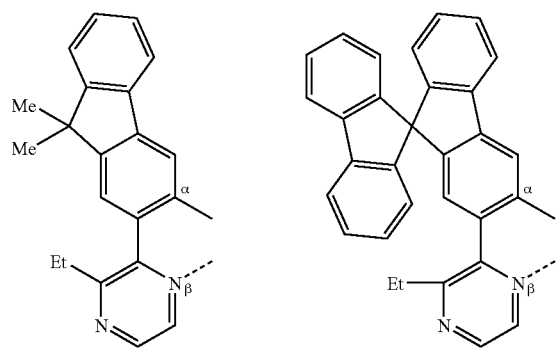
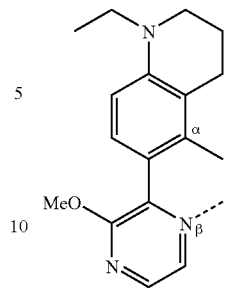
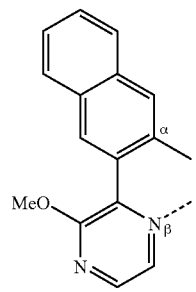
ligand group 3
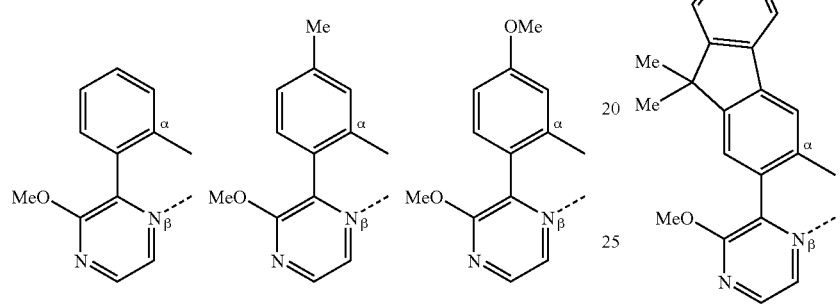
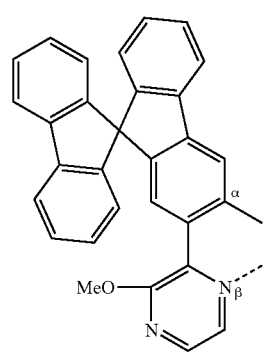
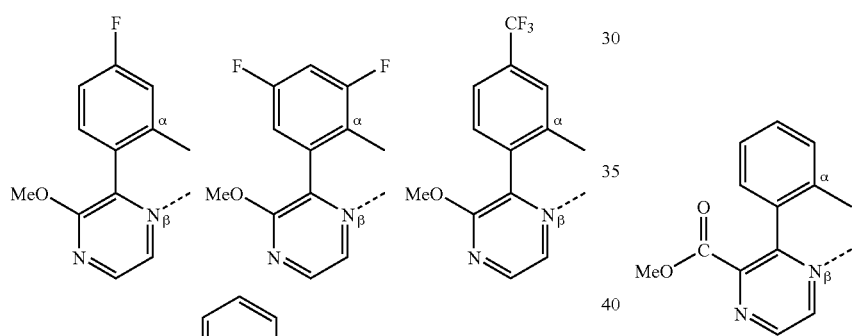
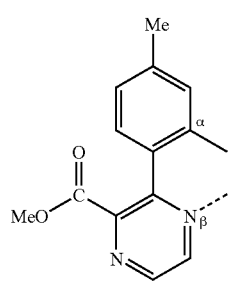
ligand group 4
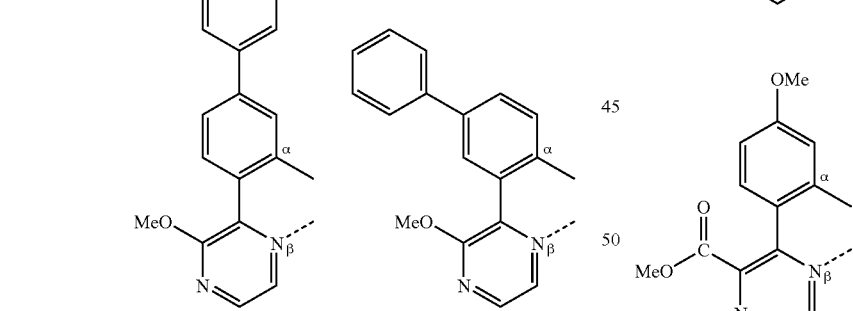
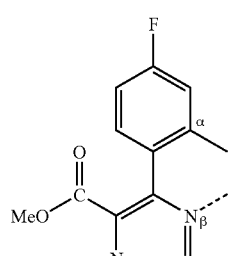
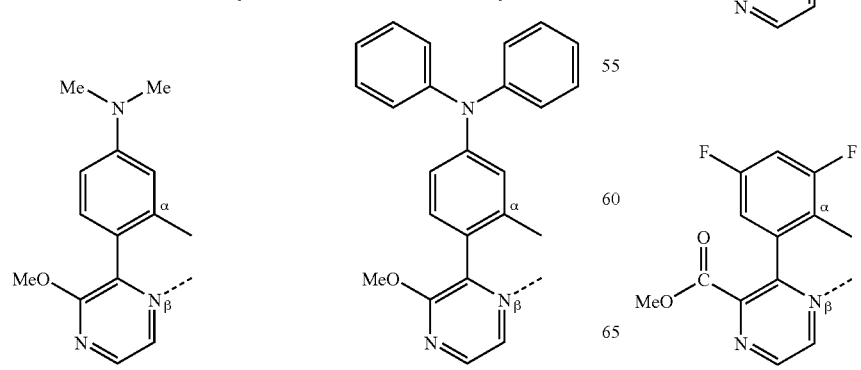
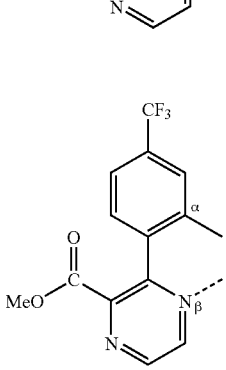

-continued
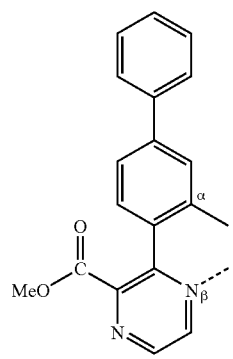 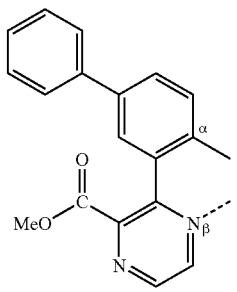 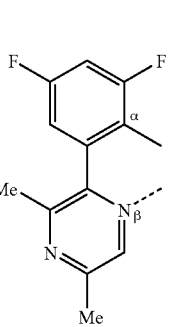 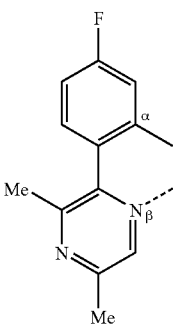 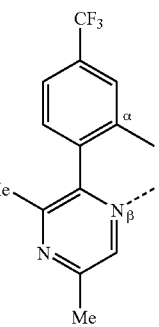
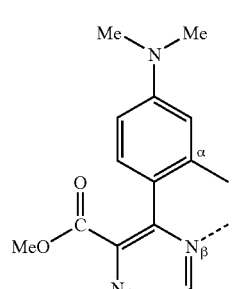 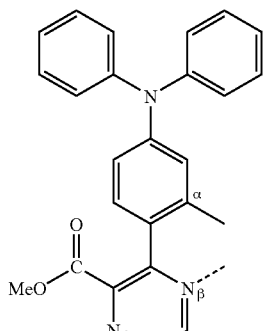 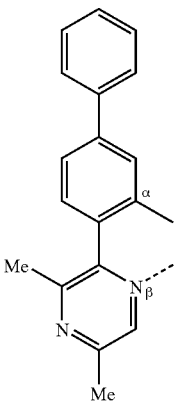
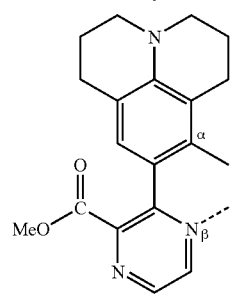 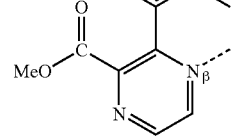 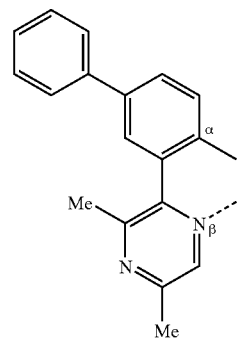
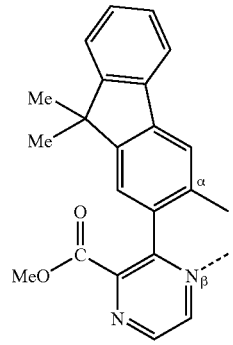 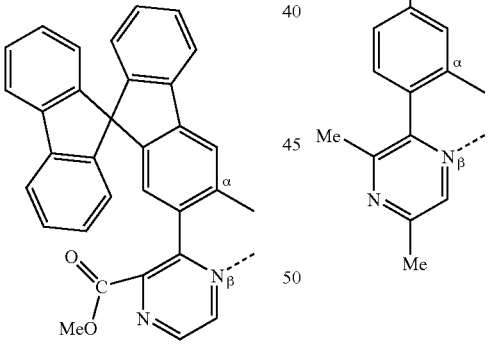 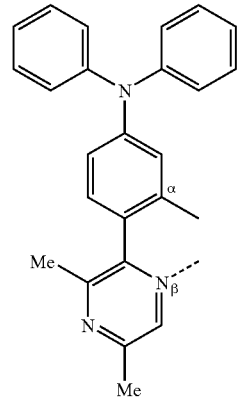
ligand group 5
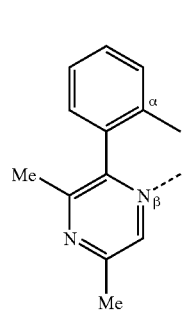 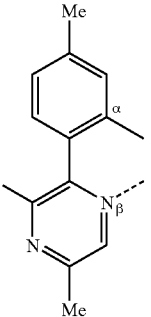 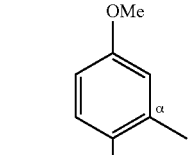 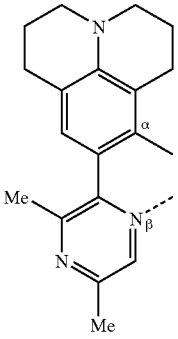 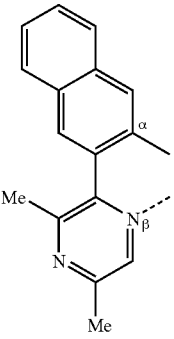

-continued
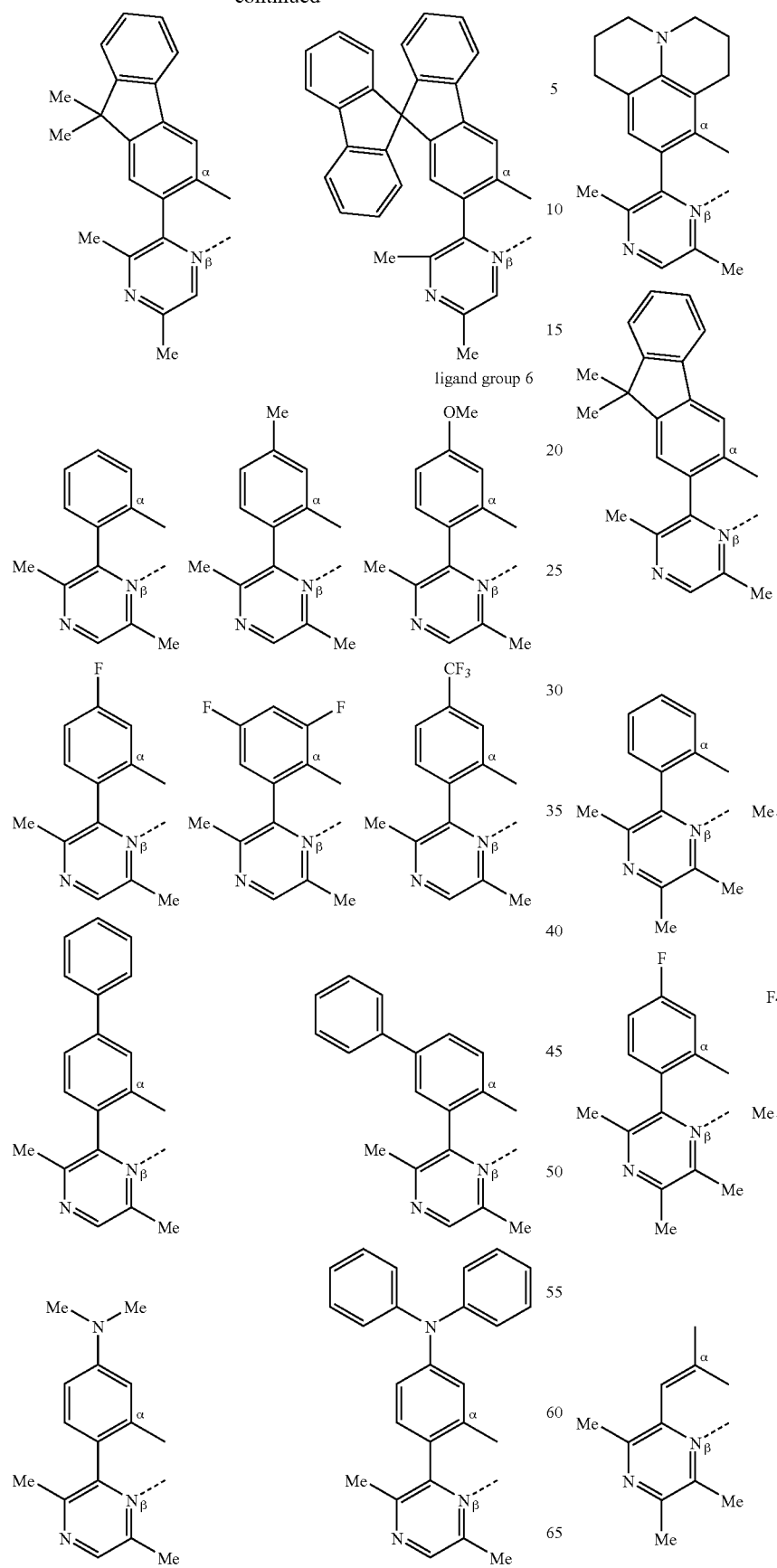
ligand group 6
-continued
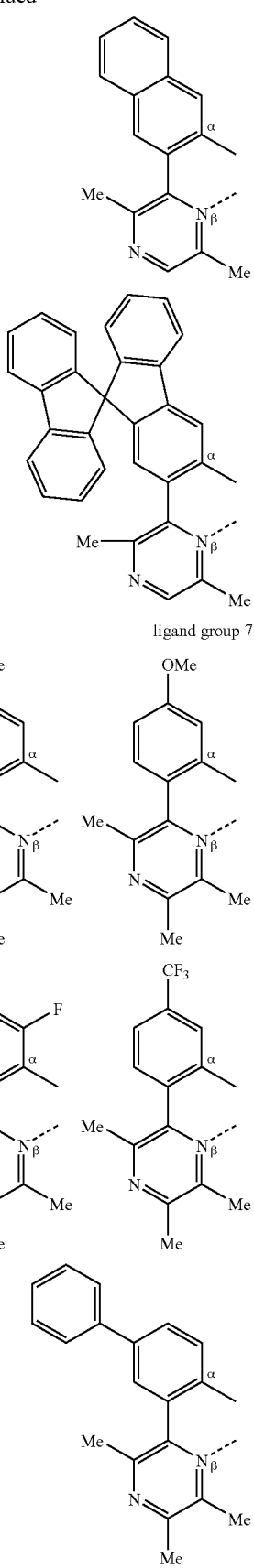
ligand group 7

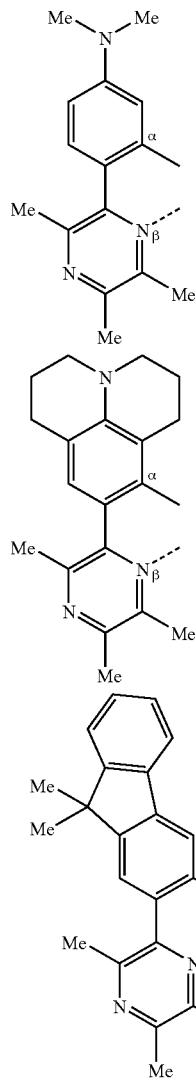

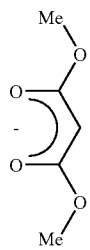
(L2)

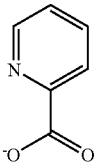
(L3)

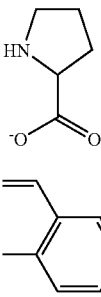
(L4)

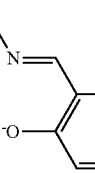
(L5)

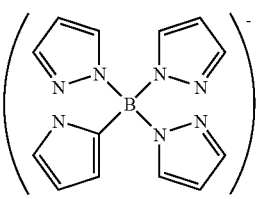
(L6)

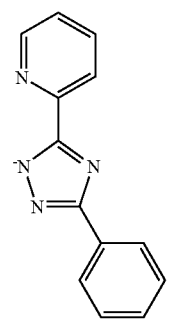
(L7)

Then, the monoanionic ligand L in the general formula (G10) is described. The monoanionic ligand L is preferably either a monoanionic bidentate chelate ligand having a β-diketone structure, a monoanionic chelate bidentate ligand having a carboxyl group, a monoanionic bidentate chelate ligand having a phenolic hydroxyl group, or a monoanionic bidentate chelate ligand in which two ligand elements are both nitrogen. This is because these ligands have high coordinative ability. More specifically, monoanionic ligands represented by the structural formulas (L1) to (L8) are given; however, the present invention is not limited to these.

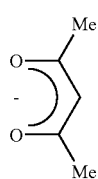
(L1)

(L8)

By using the center metal M, the ligand groups 1 to 7, the monoanionic ligand L as described above in combination as appropriate, an organometallic complex of the present invention is constituted. Hereinafter, specific structural formulas (1) to (56) of organometallic complexes of the present invention are given. However, the present invention is not limited to these.

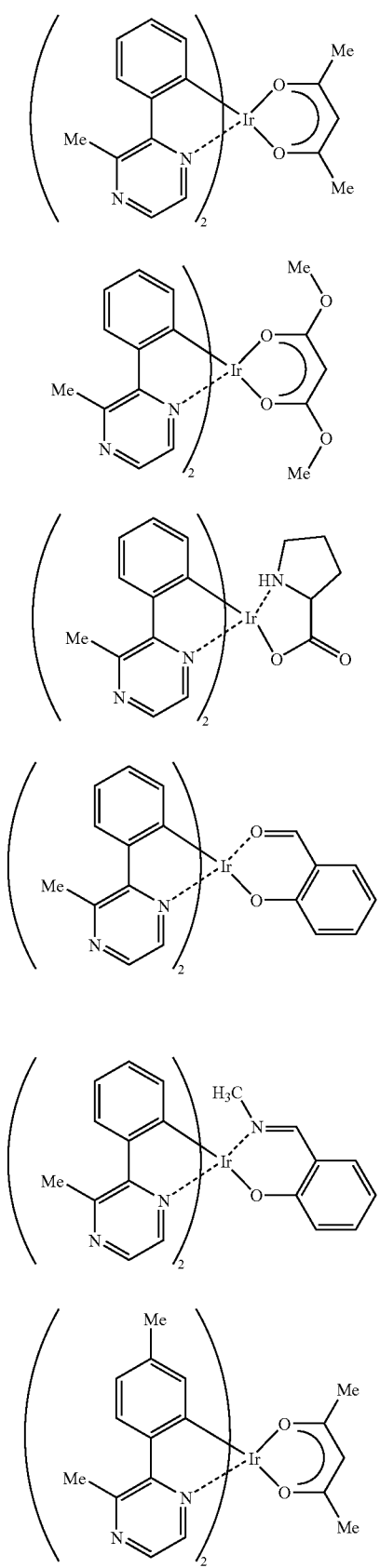
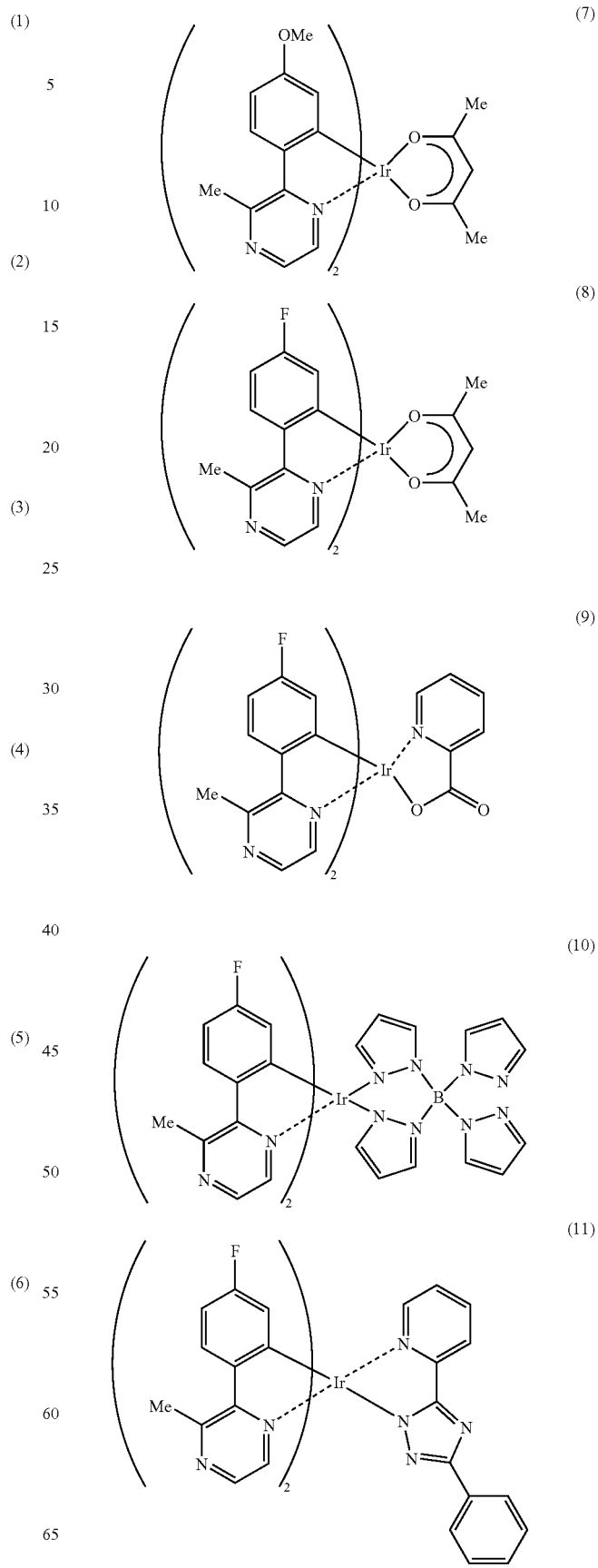

-continued
(12)
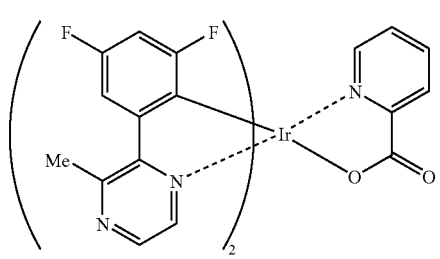
(13)
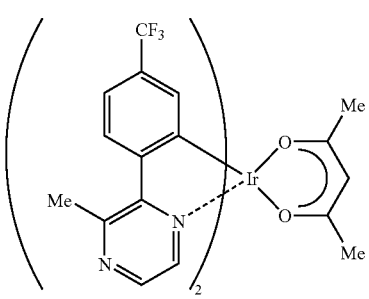
(14)
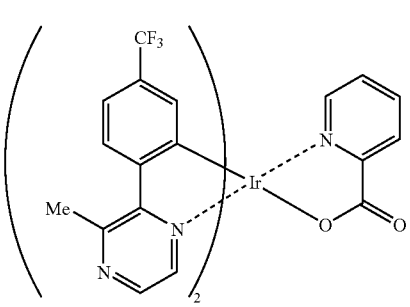
(15)
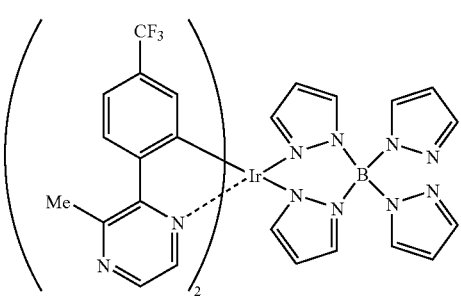
(16)
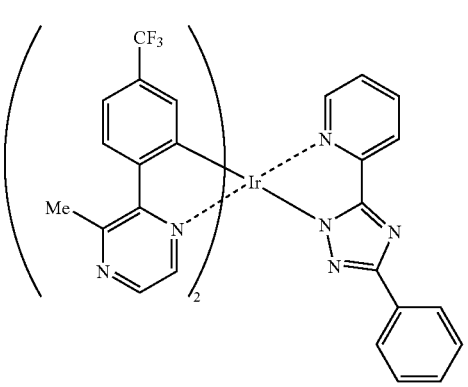
-continued
(17)
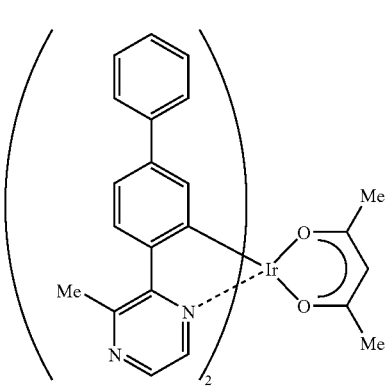
(18)
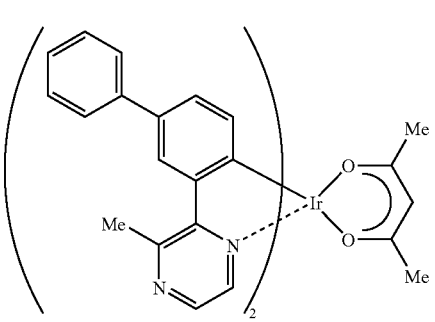
(19)
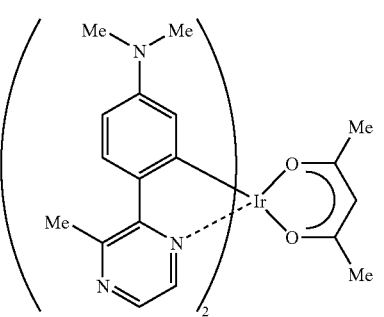
(20)
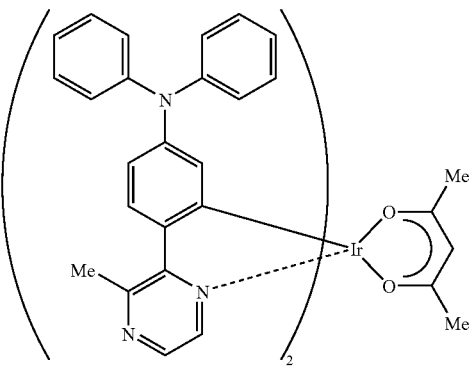

-continued
(21)
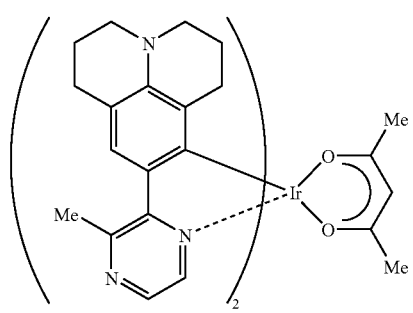
(22)
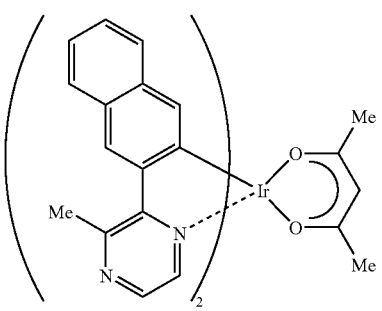
(23)
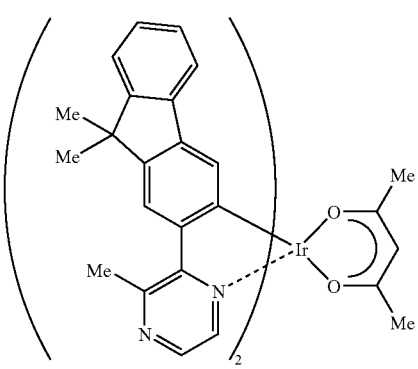
(24)
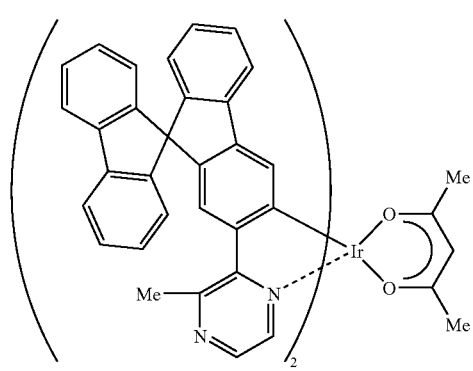
(25)
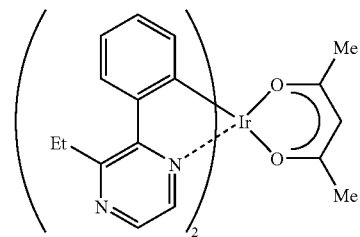
-continued
(26)
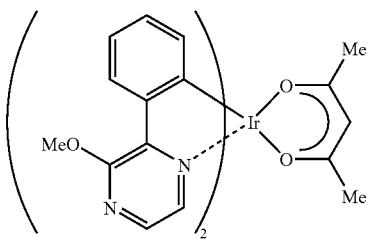
(27)
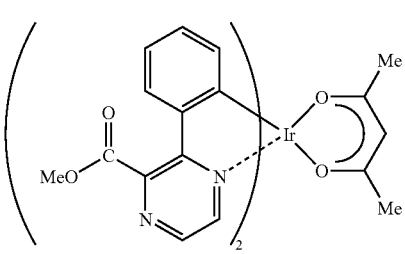
(28)
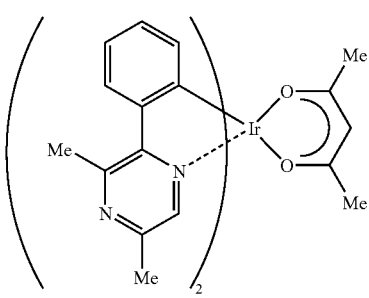
(29)
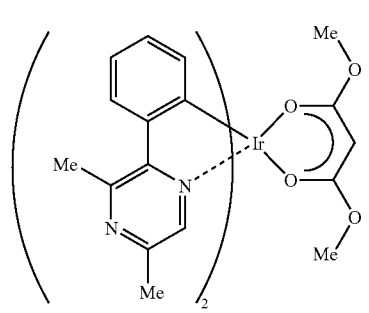
(30)
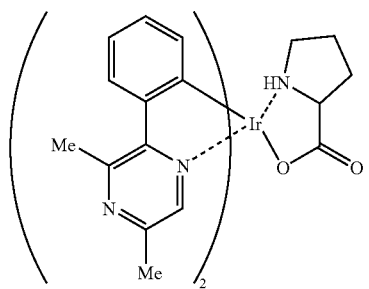

-continued
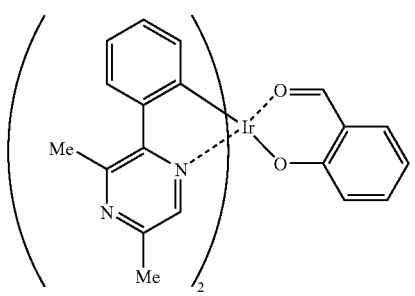 (31)
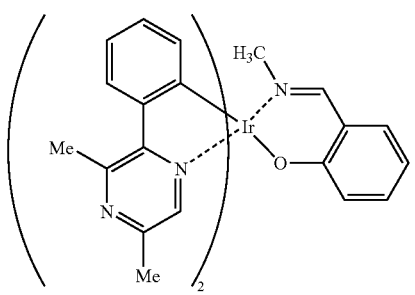 (32)
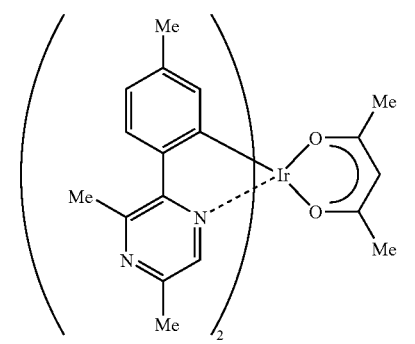 (33)
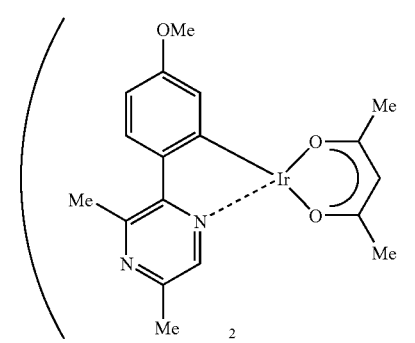 (34)
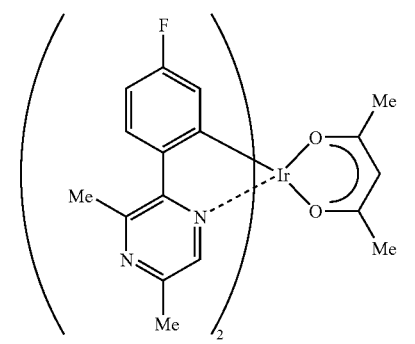 (35)
-continued
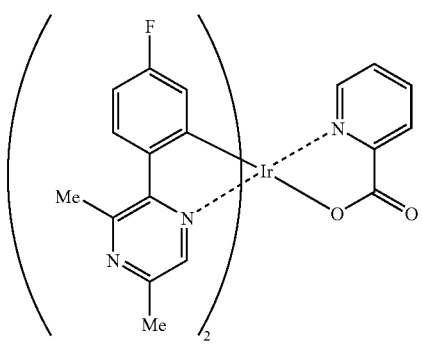 (36)
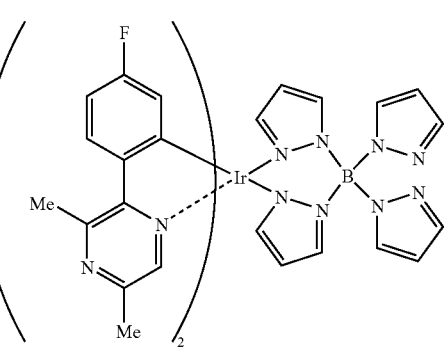 (37)
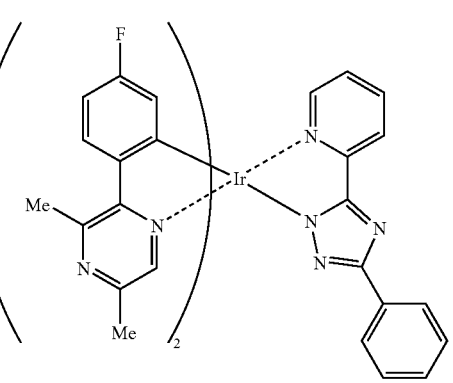 (38)
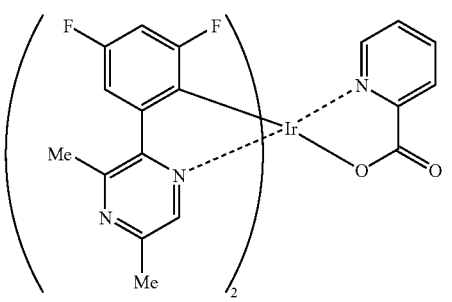 (39)

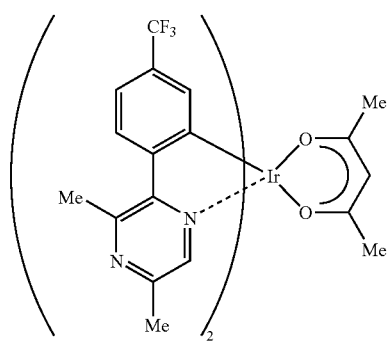
(40)
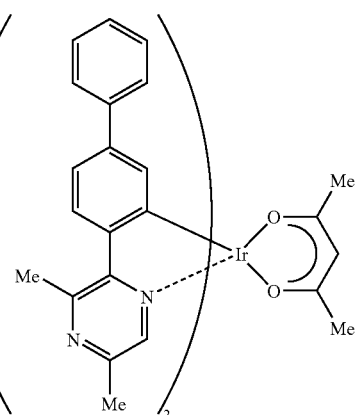
(44)
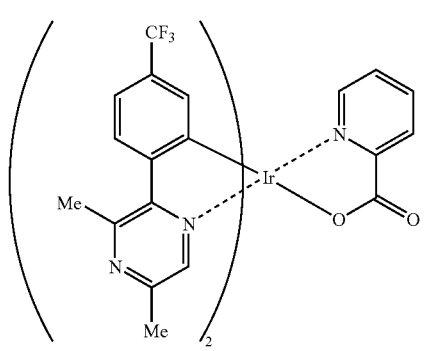
(41)
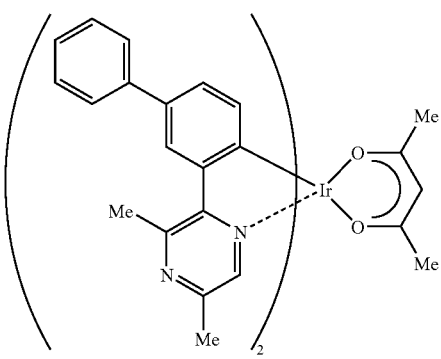
(45)
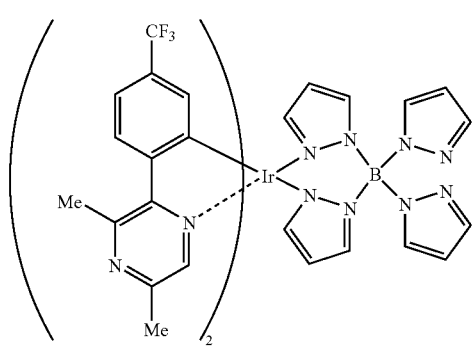
(42)
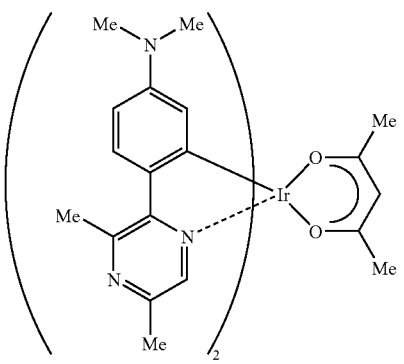
(46)
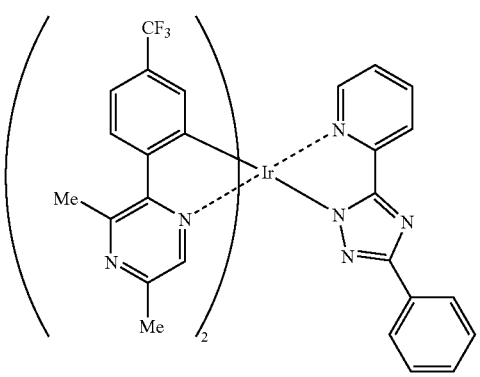
(43)
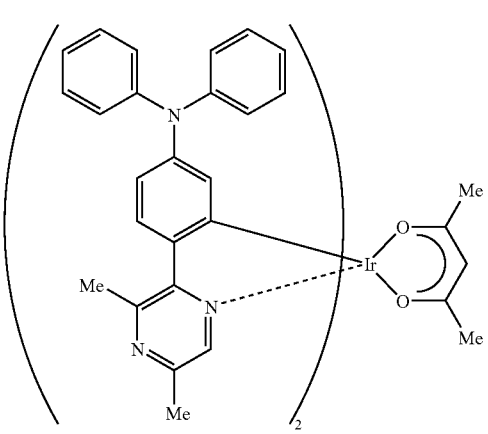
(47)

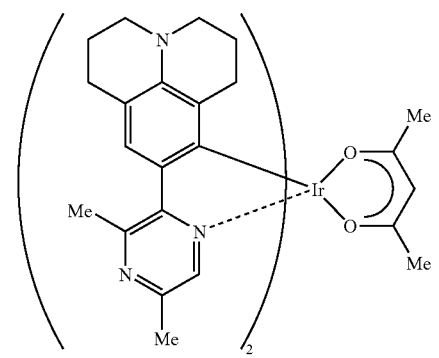
(48)
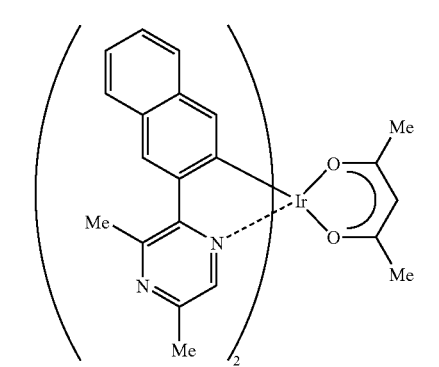
(49)
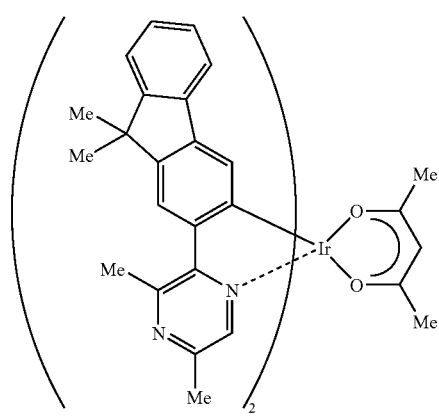
(50)
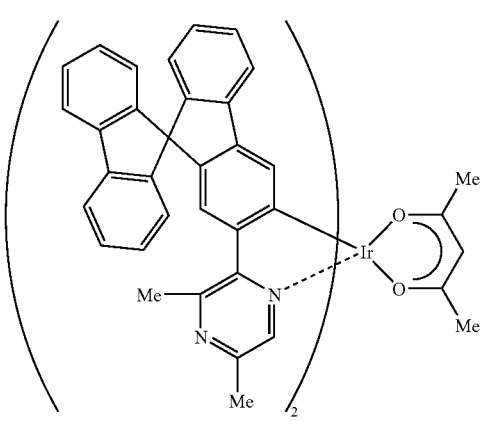
(51)
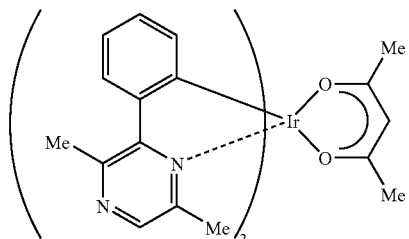
(52)
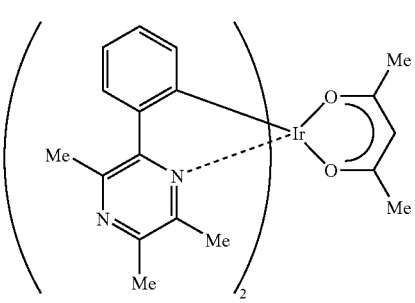
(53)
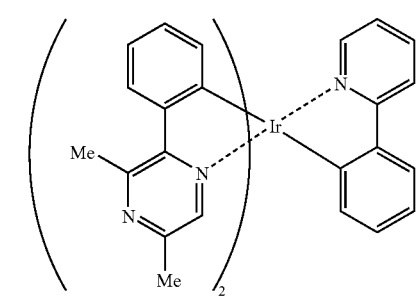
(54)
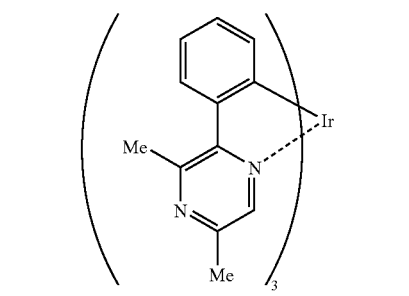
(55)
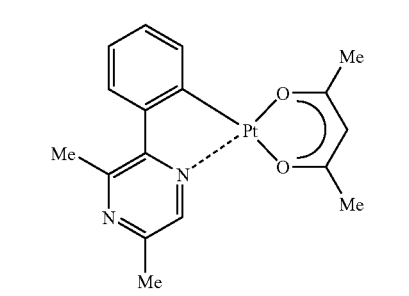
(56)
In the organometallic complexes represented by the above structural formulas (1) to (56), there can be a geometrical isomer and a stereoisomer according to the type of ligand. The organometallic complex of the present invention includes such isomers.
In addition, there are two geometrical isomers of a facial isomer and a meridional isomer as the organometallic complex represented by the structural formula (55). The organometallic complex of the present invention includes such isomers, too.

The foregoing organometallic complex of the present invention can be used as a photosensitizer due to capability of intersystem crossing, and further, emit phosphorescence. Thus, the organometallic complexes of the present invention can be applied as a light-emitting material or a luminescent substance for a light-emitting element.

Embodiment Mode 2

Embodiment Mode 2 will describe a mode of a light-emitting element which has the organometallic complex of the present invention described in Embodiment Mode 1, as a luminescent substance with reference to FIG. 1.

As shown in FIG. 1, a light-emitting element has a light-emitting layer 113 formed between a first electrode 101 and a second electrode 102. The light-emitting layer 113 includes the organometallic complex of the present invention as described in Embodiment Mode 1.

By applying a voltage to such a light-emitting element, holes injected from the first electrode 101 side and electrons injected from the second electrode 102 side recombine with each other in the light-emitting layer 113 to bring the organometallic complex of the present invention to an excited state. And when the organometallic complex in the excited state returns to a ground state, it emits light. As thus described, the organometallic complex of the present invention functions as a luminescent substance of the light-emitting element. In the light-emitting element of Embodiment Mode 2, the first electrode 101 functions as an anode and the second electrode 102 functions as a cathode.

Here, the light-emitting layer 113 includes an organometallic complex of the present invention. The light-emitting layer 113 is preferably a layer including a substance which has a larger energy gap than that of the organometallic complex of the present invention as a host, and as a guest, the organometallic complex of the present invention which is dispersedly contained. Thus, quenching of light emitted from the organometallic complex of the present invention caused depending on the concentration can be prevented. It is to be noted that the triplet excited energy indicates an energy gap between a ground state and a triplet excited state.

There are no particular limitations on the substance (i.e., a host) used for dispersing the organometallic complex of the present invention. In addition to a compound having an arylamine skeleton such as 2,3-bis(4-diphenylaminophenyl)quinoxaline (abbreviation: TPAQn) or 4,4'-bis[N-(1-naphthyl)-N-phenylamino]biphenyl (abbreviation: NPB), a carbazole derivative such as 4,4'-di(N-carbazolyl)biphenyl (abbreviation: CBP) or 4,4',4"-tris(N-carbazolyl)triphenylamine (abbreviation: TCTA), or a metal complex such as bis[2-(2-hydroxyphenyl)pyridinato]zinc (abbreviation: $Znpp_2$), bis[2-(2-hydroxyphenyl)benzoxazolato]zinc (abbreviation: ZnBOX), bis(2-metyl-8-quinolinolato)(4-phenyphenolato)aluminum (abbreviation: BAlq) or tris(8-quinolinolato)aluminum (abbreviation: $Alq_3$), or the like is preferably used. Moreover, a high molecular compound such as poly(N-vinylcarbazole) (abbreviation: PVK) can also be used.

Since the organometallic complex of the present invention has enriched variation of emission color of green light to red light, a light-emitting element which can emit various light of green to red, can be provided. Since the organometallic complex of the present invention has a sharp emission spectrum, a light-emitting element with high color purity can be provided. Furthermore, since the organometallic complex of the present invention has luminous efficiency of phosphorescence, a light-emitting element with high luminous efficiency can be provided.

Although there are no particular limitations on the first electrode 101, the first electrode 101 is preferably formed by using a substance which has a high work function when the first electrode 101 functions as an anode as in Embodiment Mode 2. Specifically, in addition to indium tin oxide (ITO), indium tin oxide containing silicon oxide (ITSO), and indium oxide containing zinc oxide at 2 to 20 wt % (IZO); gold (Au), platinum (Pt), nickel (Ni), tungsten (W), chromium (Cr), molybdenum (Mo), iron (Fe), cobalt (Co), copper (Cu), palladium (Pd), or the like can be used. The first electrode 101 can be formed by, for example, a sputtering method, an evaporation method, or the like.

Further, although there are not particular limitations of the second electrode 102, the second electrode 102 is preferably formed from a substance which has a low work function when the second electrode 102 functions as a cathode as in Embodiment Mode 2. Specifically, in addition to aluminum (Al) or indium (In), an alkali metal such as lithium (Li) or cesium (Cs); an alkali-earth metal such as magnesium (Mg) or calcium (Ca); a rare-earth metal such as erbium (Er) or ytterbium (Yb) or the like can be used. In addition, an alloy such as aluminum-lithium alloy (AlLi) or magnesium-silver alloy (MgAg) can also be used. The second electrode 102 can be formed by, for example, a sputtering method, an evaporation method, or the like.

In order to extract emitted light to the outside, one or both of the first electrode 101 and the second electrode 102 is/are preferably an electrode formed of a conductive film of indium tin oxide (ITO) or the like which can transmit visible light or an electrode with a thickness of several to several tens nm so as to transmit visible light.

In addition, a hole-transporting layer 112 may be provided between the first electrode 101 and the light-emitting layer 113 as shown in FIG. 1. Here, a hole-transporting layer is a layer which has a function of transporting holes injected from the first electrode 101 to the light-emitting layer 113. The hole-transporting layer 112 is provided to keep the first electrode 101 away from the light-emitting layer 113 in this way; thus, quenching of light due to a metal can be prevented. However, the hole-transporting layer 112 is not necessarily provided.

There are no particular limitations on the hole-transporting layer 112, and a layer formed from, for example, an aromatic amine compound (that is, a compound having a benzene ring-nitrogen bond) such as 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4'-bis[N-(9,9-dimetylfluoren-2-yl)-N-phenylamino]biphenyl (abbreviation: DFLDPBi), 4,4',4"-tris(N,N-diphenylamino)triphenylamine (abbreviation: TDATA), or 4,4',4"-tris[N-(3-methylphenyl)-N-phenylamino]triphenylamine (abbreviation: m-DATA) can be used. Moreover, a high molecular compound such as poly(4-vinyl triphenylamine) (abbreviation: PVTPA) can also be used.

In addition, the hole-transporting layer 112 may have a multilayer structure in which two or more layers are stacked, or may be formed by combining two or more substances.

Further, an electron-transporting layer 114 may be provided between the second electrode 102 and the light-emitting layer 113 as shown in FIG. 1. Here, the electron transporting layer is a layer which has a function of transporting electrons injected from the second electrode 102 to the light-emitting layer 113. The electron-transporting layer 114 is provided to keep the second electrode 102 away from the light-emitting layer 113 in this way; thus, quenching of light due to a metal can be prevented. Note that the electron-transporting layer 114 is not necessarily provided.

There are no particular limitations on the electron-transporting layer 114. Typically, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolato)(4-phenylphenolato)aluminum (abbreviation: BAlq), bis[2-(2-hydroxyphenyl)-benzoxazolato]zinc (abbreviation: Zn(BOX)$_2$), or bis[2-(2-hydroxyphenyl)-benzothiazolato]zinc (abbreviation: Zn(BTZ)$_2$) may be used. Further, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), or 4,4'-bis(5-methylbenzoxazol-2-yl)stilbene (abbreviation: BzOs) can also be used. 2,9-Dimethyl-4,7-diphenyl-1,10-phenanthroline), or the like can be used. In addition, a high molecular compound such as poly(2,5-pyridine-diyl) (abbreviation: PPy) can also be used.

In addition, the electron-transporting layer 114 may have a multilayer structure in which two or more layers are stacked, or may be formed by combining two or more substances.

Further, a hole-injecting layer 111 may be provided between the first electrode 101 and the hole-transporting layer 112 as shown in FIG. 1. Here, a hole-injecting layer is a layer that has a function of assisting injection of holes from an electrode functioning as an anode to the hole-transporting layer 112. Note that the hole-injecting layer 111 is not necessarily provided.

There are no particular limitations on the hole-injecting layer 111. For forming the hole-injecting layer 111, a metal oxide such as vanadium oxide ($VO_x$), niobium oxide ($NbO_x$), tantalum oxide ($TaO_x$), chromium oxide ($CrO_x$), molybdenum oxide ($MoO_x$), tungsten oxide ($WO_x$), manganese oxide ($MnO_x$), rhenium oxide ($ReO_x$), or ruthenium oxide ($RuO_x$) can be used. In addition, a phthalocyanine based compound such as phthalocyanine (abbreviation: H$_2$Pc) or copper phthalocyanine (abbreviation: CuPc) can also be used. In addition, substances for forming the hole-transporting layer 112 as described above can also be used. Further, a high molecular compound such as a mixture of poly(ethylenedioxythiophene) and poly(styrene sulfonate) (abbreviation: (PEDOT/PSS)) can also be used.

A composite material which is formed by combining an organic compound and an electron acceptor may be used for the hole-injecting layer 111. The composite material is superior in a hole-injecting property and a hole-transporting property, since holes are generated in the organic compound by the electron acceptor. In this case, the organic compound is preferably a material excellent in transporting the generated holes. Specifically, the foregoing substances for forming the hole-transporting layer 112 (such as aromatic amine-based compound) can be used for example. In addition, as the electron acceptor, a substance showing an electron accepting property to an organic compound may be used, and specifically, a transition metal oxide is preferable. For example, vanadium oxide ($VO_x$), niobium oxide ($NbO_x$), tantalum oxide ($TaO_x$), chromium oxide ($CrO_x$), molybdenum oxide ($MoO_x$), tungsten oxide ($WO_x$), manganese oxide ($MnO_x$), rhenium oxide ($ReO_x$), ruthenium oxide ($RuO_x$) and the like are given. Lewis acid such as iron chloride(III) or aluminum chloride(III) can also be used. In addition, an organic compound such as 7,7,8,8-tetracyano-2,3,5,6-tetrafluoroquinodimethane (abbreviation: F4-TCNQ) can also be used.

The hole-injecting layer 111 may have a multilayer structure in which two or more layers are stacked, or may be formed by combining two or more substances.

Further, an electron-injecting layer 115 may be provided between the second electrode 102 and the electron-transporting layer 114 as shown in FIG. 1. Here, the electron injecting layer is a layer which has a function of assisting injection of electrons from the electrode functioning as a cathode to the electron-transporting layer 114. It is to be noted that the electron-injecting layer 115 is not necessarily provided.

There are no particular limitations on the electron-injecting layer 115. A compound of an alkali metal or an alkali-earth metal such as lithium fluoride (LiF), cesium fluoride (CsF), calcium fluoride (CaF$_2$), lithium oxide (LiOx) or the like can be used. In addition, a rare earth metal compound such as erbium fluoride (ErF$_3$) can also be used. The above-mentioned substances for forming the electron-transporting layer 114 can also be used.

A composite material which is formed by combining an organic compound and an electron donor may be used for the electron-injecting layer 115. The composite material is superior in an electron-injecting property and an electron-transporting property, since electrons are generated in the organic compound by the electron donor. In this case, the organic compound is preferably a material excellent in transporting the generated electrons. Specifically, the foregoing materials for forming the electron transporting layer 114 (for example, a metal complex, a heteroaromatic compound or the like) can be used for example. As the electron donor, a substance showing an electron donating property to the organic compound may be used, and specifically an alkali metal, an alkali-earth metal or a rare earth metal, for example, lithium, cesium, magnesium, calcium, erbium, or ytterbium, is preferable. For example, an alkali metal oxide, or an alkali-earth metal oxide is preferable, and for example, lithium oxide (LiO$_x$), calcium oxide (CaC$_x$), barium oxide (BaO$_x$), or the like can be given. Lewis acid such as magnesium oxide can also be used. In addition, an organic compound such as tetrathiafulvalene (abbreviation: TTF) can also be used.

In the foregoing light-emitting element of the present invention, each of the hole-injecting layer 111, the hole-transporting layer 112, the light-emitting layer 113, the electron-transporting layer 114, and the electron-injecting layer 115 may be formed by any method, for example, an evaporation method, an inkjet method, an application method, or the like. In addition, the first electrode 101 or the second electrode 102 may be formed by any method, for example, a sputtering method, an evaporation method, an inkjet method, an application method, or the like.

Embodiment Mode 3

The light-emitting element of the present invention may have a plurality of light-emitting layers. For example, white light can be obtained by providing a plurality of light-emitting layers and mixing light emitted from each of the light-emitting layers. In Embodiment Mode 3, a light-emitting element having a plurality of light-emitting layers is described with reference to FIG. 2.

Figure 2:
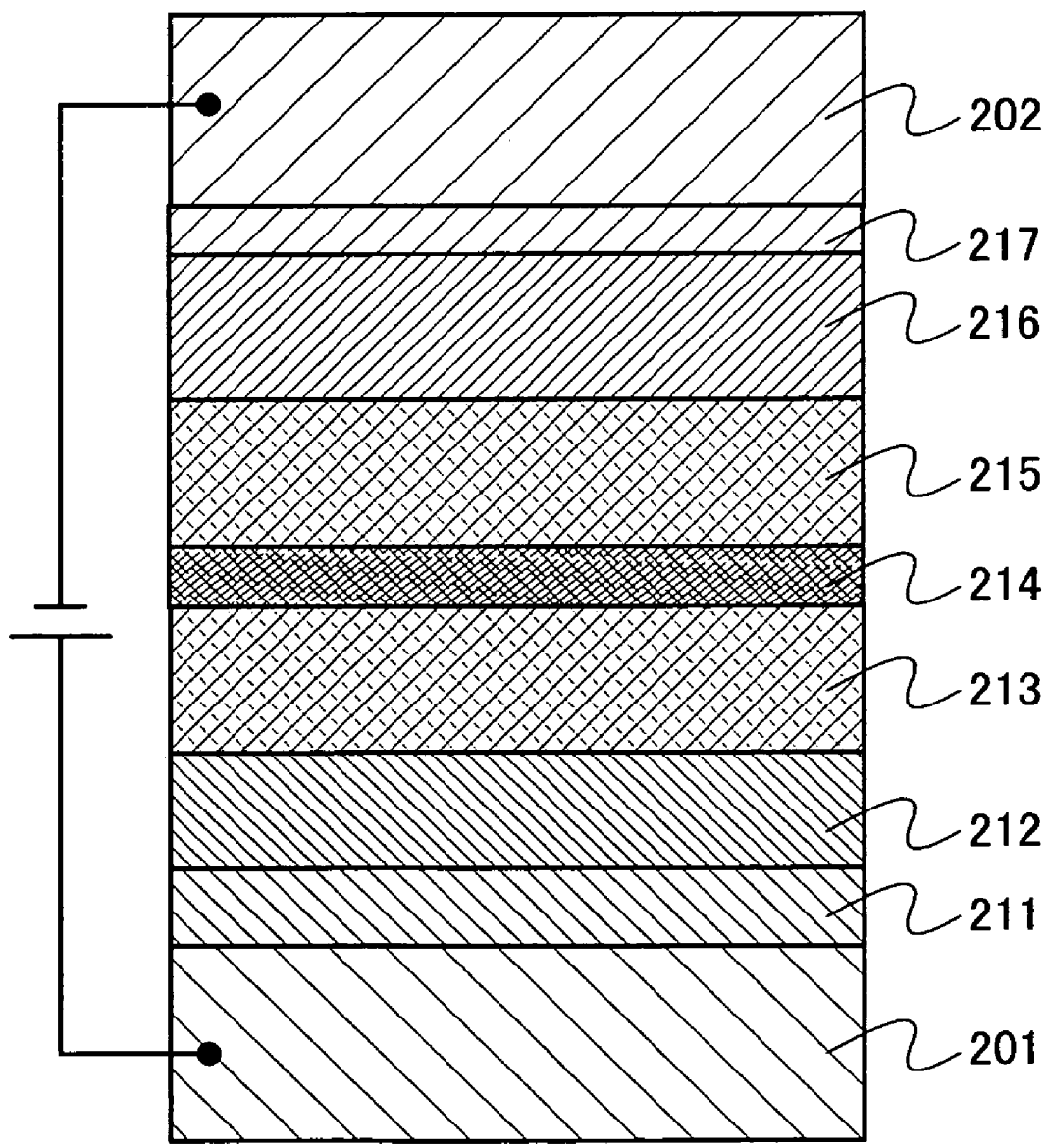
FIG. 2 shows a structure of a light-emitting element using an organometallic complex in accordance with an aspect of the present invention.

In FIG. 2, a first light-emitting layer 213 and a second light-emitting layer 215 are provided between a first electrode 201 and a second electrode 202. Light in which light emitted from the first light-emitting layer 213 and light emitted from the second light-emitting layer 215 are mixed can be obtained. A separation layer 214 is preferably formed between the first light-emitting layer 213 and the second light-emitting layer 215.

When a voltage is applied so that the potential of the first electrode 201 is higher than the potential of the second electrode 202, current flows between the first electrode 201 and the second electrode 202, and holes and electrons are recombined in the first light-emitting layer 213, the second light-emitting layer 215, or the separation layer 214. Generated excitation energy is distributed to the first light-emitting layer 213 and the second light-emitting layer 215 to bring each of a first luminescent substance contained in the first light-emitting layer 213 and a second luminescent substance contained in the second light-emitting layer 215 to an excited state. Then, the first and second luminescent substances in the excited state emit light when returning to the ground state.

The first light-emitting layer 213 contains the first luminescent substance typified by a fluorescent substance such as perylene, 2,5,8,11-tetra(tert-butyl)perylene (abbreviation: TBP), 4,4'-bis(2,2-diphenylvinyl)biphenyl (abbreviation: DPVBi), 4,4'-bis[2-(N-ethylcarbazol-3-yl)vinyl]biphenyl (abbreviation: BCzVBi), bis(2-methyl-8-quinolinolato)(4-phenylphenolato)aluminum (abbreviation: BAlq), or bis(2-methyl-8-quinolinolato)galliumchloride (abbreviation: Gamq$_2$Cl), or a phosphorescent substance such as bis-{2-[3,5-bis(trifluoromethyl)phenyl]pyridinato-N,C$^{2'}$}iridium(III) picolinate (abbreviation Ir(CF$_3$ppy)$_2$(Pic)), bis[2-(4,6-difluorophenyl)pyridinato-N,C$^{2'}$]iridium(III)acetylacetonate (abbreviation FIr(acac)), bis[2-(4,6-difluorophenyl)pyridinato-N,C$^{2'}$]iridium(III)picolinate (abbreviation: FIrpic), or bis[2-(4,6-difuluorophenyl)pyridinato-N,C$^{2'}$]iridium(III) tetra(1-pyrazolyl)borate (abbreviation: FIr6), from which light emission with a peak at 450 to 510 nm in an emission spectrum (i.e., blue light to blue green light) can be obtained. In addition, when the first luminescent substance is a fluorescent compound, the light-emitting layer 213 may have a structure in which a substance having a larger singlet excited energy than the first luminescent substance is used as a first host and the first luminescent substance is dispersedly contained as a guest. Further, when the first luminescent substance is a phosphorescent compound, the light-emitting layer 213 preferably has a structure in which a substance having a larger triplet excited energy than the first luminescent substance is used as a first host and the first luminescent substance is dispersedly contained as a guest. As the first host, 9,10-di(2-naphthyl)anthracene (abbreviation: DNA), 2-tert-butyl-9,10-di(2-naphthyl)anthracene (abbreviation: t-BuDNA) or the like can be used as well as NPB, CBP, TCTA or the like. It is noted that the singlet exited energy is energy difference between a ground state and a singlet excited state and the triplet exited energy is energy difference between a ground state and a triplet excited state.

On the other hand, the second light-emitting layer 215 includes an organometallic complex of the present invention and can exhibit light emission of green to red. The second light-emitting layer 215 may have the same structure as the light-emitting layer 113 described in Embodiment Mode 2.

In addition, the separation layer 214 can be formed from TPAQn, NPB, CBP, TCTA, Znpp$_2$, ZnBOX or the like described above, specifically. In this way, by providing the separation layer 214, a defect that emission intensity of one of the first light-emitting layer 213 and the second light-emitting layer 215 is stronger than the other can be prevented. Note that the separation layer 214 is not necessarily provided, and it may be provided such that the ratio in emission intensity of the first light-emitting layer 213 and the second light-emitting layer 215 can be adjusted.

In Embodiment Mode 3, an organometallic complex of the present invention is used for the second light-emitting layer 215, and another luminescent substance is used for the first light-emitting layer 213; however, the organometallic complex of the present invention may be used for the first light-emitting layer 213, and another luminescent substance is used for the second light-emitting layer 215.

In Embodiment Mode 3, a light-emitting element including two light-emitting layers is described as shown in FIG. 2; however, the number of the light-emitting layers is not limited to two, and may be three, for example. Light emission from each light-emitting layer may be mixed. As a result, white color emission can, for example, be obtained.

In addition, the first electrode 201 may have the same structure as the first electrode 101 described in Embodiment Mode 2. In addition, the second electrode 202 may have the same structure as the second electrode 102 described in Embodiment Mode 2.

In Embodiment Mode 3, as shown in FIG. 2, the hole-injecting layer 211, the hole-transporting layer 212, the electron-transporting layer 216, and the electron-injecting layer 217 are provided; however, also to structures of these layers, the structures of the respective layers described in Embodiment Mode 2 may be applied. However, these layers are not necessarily provided and may be provided according to element characteristics.

Embodiment Mode 4

Embodiment Mode 4 exemplifies a light-emitting element which includes a plurality of light-emitting layers, which has a different element structure from that in Embodiment Mode 3, and in which light is emitted from each light-emitting layer. Therefore, also in Embodiment Mode 4, light in which plural emissions are mixed can be obtained. In other words, white light can be obtained. Hereinafter, description is made with reference to FIG. 3.

Figure 3:
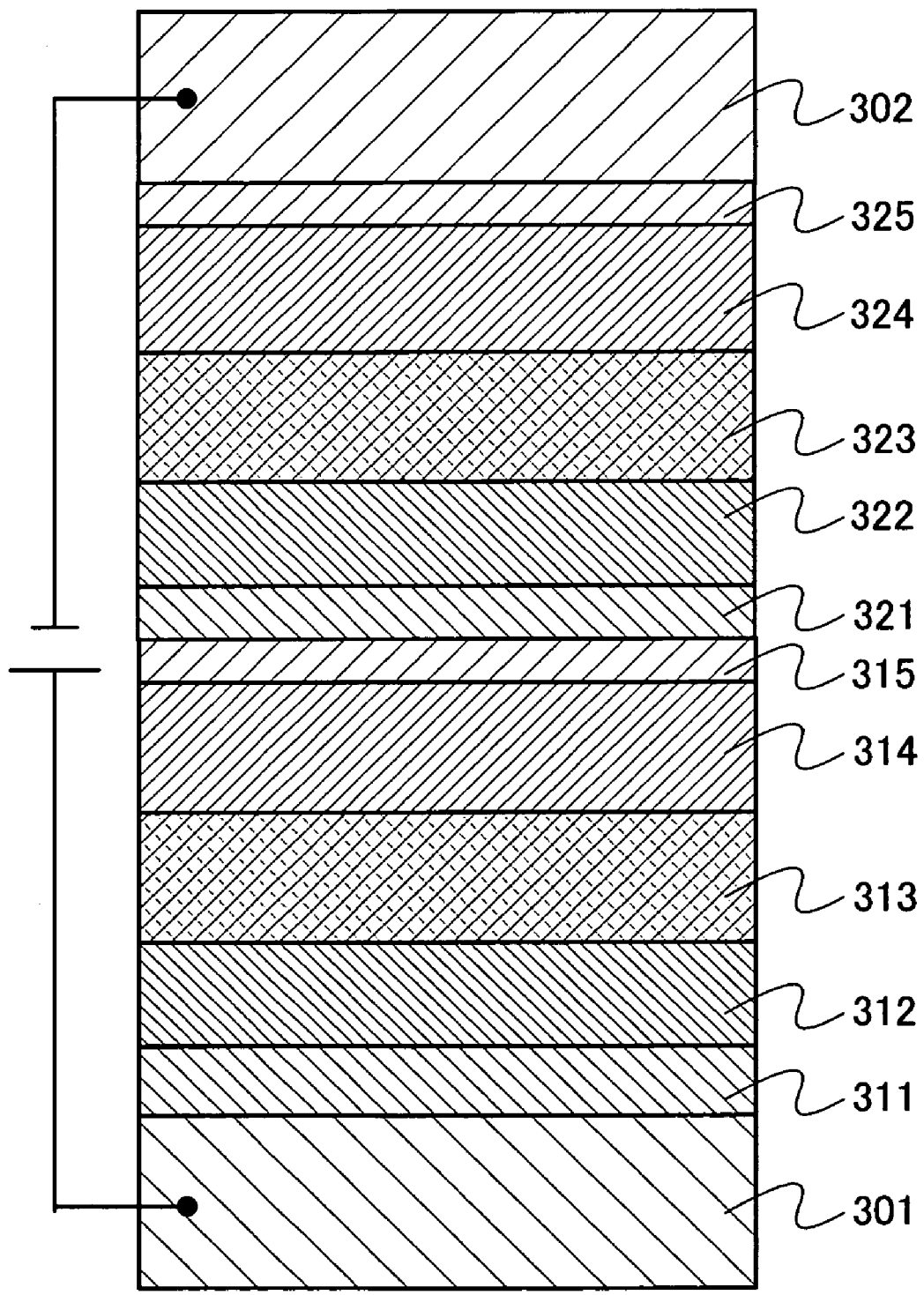
FIG. 3 shows a structure of a light-emitting element using an organometallic complex in accordance with an aspect of the present invention.

In the light-emitting element in FIG. 3, a first light-emitting layer 313 and a second light-emitting layer 323 are provided between a first electrode 301 and a second electrode 302. An N layer 315 and a P layer 321 as charge generating layers are provided between the first light-emitting layer 313 and the second light-emitting layer 323.

The N layer 315 is a layer for generating electrons, and the P layer 321 is a layer for generating holes. When a voltage is applied such that the potential of the first electrode 301 is higher than that of the second electrode 302, holes injected from the first electrode 301 and electrons injected from the N layer 315 are recombined in the first light-emitting layer 313, and thus, a first luminescent substance included in the first light-emitting layer 313 emits light. Further, electrons injected from the second electrode 302 and holes injected from the P layer 321 are recombined in the second light-emitting layer 323, and thus, a second luminescent substance included in the second light-emitting layer 323 emits light.

The first light-emitting layer 313 may have the same structure as the first light-emitting layer 213 in Embodiment Mode 3, and light with a peak of emission spectrum (i.e., blue light to blue green light ) in 450 nm to 510 nm can be emitted. The second light-emitting layer 323 may have the same structure as the second light-emitting layer 215 in Embodiment Mode 3, and includes an organometallic complex of the present invention and green light to red light can be obtained.

The N layer 315 is a layer for generating electrons and thus, may be formed using a composite material in which the organic compound and the electron donor described in Embodiment Mode 2 are combined. By adopting such a structure, electrons can be injected to the first light-emitting 313 side.

The P layer 321 is a layer for generating holes, and thus, may be formed using a composite material in which the organic compound and the electron donor described in Embodiment Mode 2 are combined. By adopting such a structure, holes can be injected to the second light-emitting 323 side. For the P layer 321, a metal oxide having an excellent hole-injecting property, such as $MoO_x$, $VO_x$, ITO, or ITSO can be used.

Here, Embodiment Mode 4 describes a light-emitting element in which the two light-emitting layers are provided as shown in FIG. 3; however, the number of light-emitting layers is not limited to two. For example, the number may be three. Light from each light-emitting layer may be mixed. Consequently, white light can be obtained for example.

The first electrode 301 may have the same structure as the first electrode 101 in Embodiment Mode 2. In addition, the second electrode 302 may have the same structure as the second electrode 102 described in Embodiment Mode 2.

In Embodiment Mode 4, as shown in FIG. 3, a hole-injecting layer 311, hole transporting layers 312 and 322, electron-transporting layers 314 and 324, and an electron-injecting layer 325 are provided. However, the layer structures described in Embodiment Mode 2 may also be applied to the hole-injecting layer 311, the hole transporting layers 312 and 322, the electron-transporting layers 314 and 324, and the electron-injecting layer 325. It is to be noted that these layers may be provided as appropriate in accordance with element characteristics, since these layers are not necessarily provided.

Embodiment Mode 5

A mode of a light-emitting element using the organometallic complex of the present invention as a sensitizer is explained with reference to FIG. 1.

FIG. 1 shows the light-emitting element having the light-emitting layer 113 between the first electrode 101 and the second electrode 102. The light-emitting layer 113 contains the organometallic complex of the present invention described in Embodiment Mode 1, and a fluorescent compound which can emit light with a longer wavelength than the organometallic complex of the present invention.

In the light-emitting element like this, holes injected from the first electrode 101 and electrons injected from the second electrode 102 are recombined in the light-emitting layer 113 to bring the fluorescent compound to an excited state. Then, light is emitted when the fluorescent compound in the excited state returns to the ground state. In this case, the organometallic complex of the present invention acts as a sensitizer for the fluorescent compound to make more molecules of the fluorescent compound be in the singlet excited state. As described above, a light-emitting element with excellent luminous efficiency can be obtained by using the organometallic complex of the present invention as a sensitizer. It is to be noted that the first electrode 101 functions as an anode and the second electrode 102 functions as a cathode in the light-emitting element in Embodiment Mode 5.

Here, the light-emitting layer 113 includes an organometallic complex of the present invention, and a fluorescent compound which can emit light with a longer wavelength than the organometallic complex of the present invention. The light-emitting layer 113 may have a structure in which a substance having a larger singlet excited energy than the fluorescent substance as well as a larger triplet excited energy than the organometallic complex of the present invention is used as a host, and the organometallic complex of the present invention and the fluorescent compound are dispersedly contained as a guest.

There are no particular limitations on a substance (i.e., host) used for dispersing the organometallic complex of the present invention and the fluorescent compound; a substance which is used as a host as in Embodiment Mode 2, or the like can be used.

In addition, there are also no particular limitations on the fluorescent complex; however, a compound which can exhibit emission of red light to infrared light is preferable, for example, 4-dicyanomethylene-2-isopropyl-6-[2-(1,1,7,7-tetramethyljulolidin-9-yl)ethenyl]-4H-pyran (abbreviation: DCJTI), magnesium phthalocyanine, magnesium porphyrin, phthalocyanine and the like are preferable.

Note that the first electrode 101 and the second electrode 102 may both have the same structure as the first electrode and the second electrode in Embodiment Mode 2, respectively.

In Embodiment Mode 5, as shown in FIG. 1, the hole-injecting layer 111, the hole-transporting layer 112, the electron-transporting layer 114, and the electron-injecting layer 115 are provided; also to these layers, the structures of the respective layers described in Embodiment Mode 2 may be applied. It is to be noted that these layers may be provided as appropriate in accordance with element characteristics, since these layers are not necessarily provided.

The foregoing light-emitting element can emit light highly efficiently by using the organometallic complex of the present invention as a sensitizer.

Embodiment Mode 6

Figure 4A:
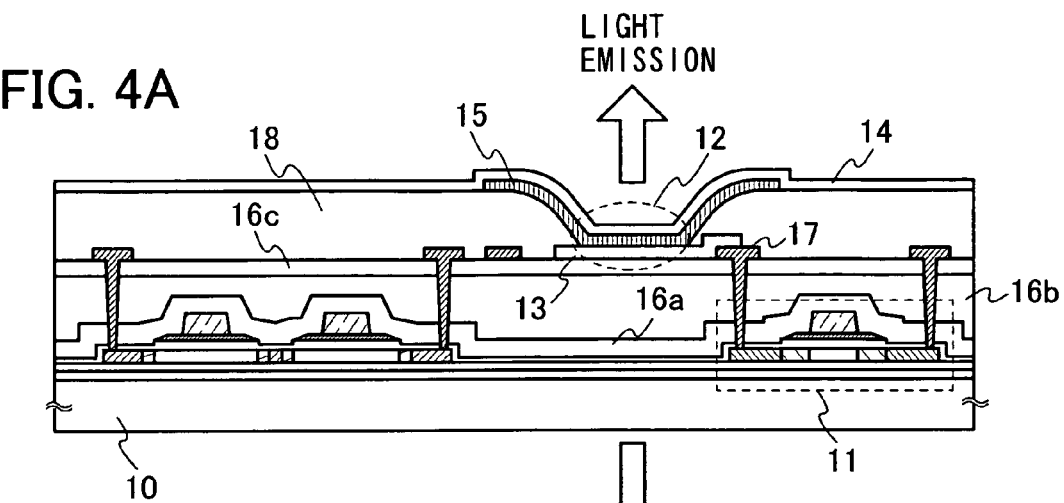
FIGS. 4A to 4C each show a light-emitting device using a light-emitting element in accordance with an aspect of the present invention.
Figure 4B:
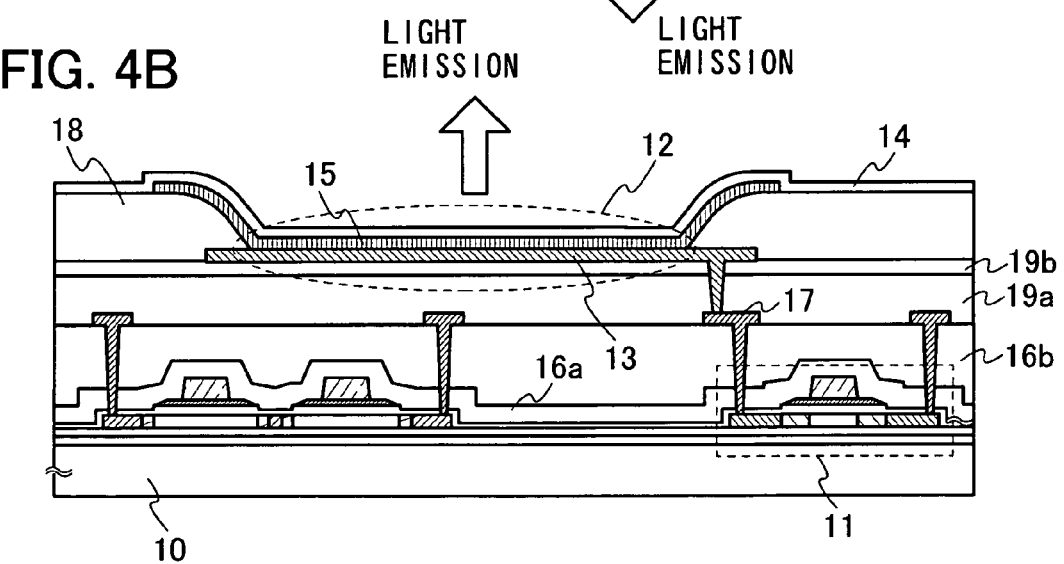
Figure 4C:
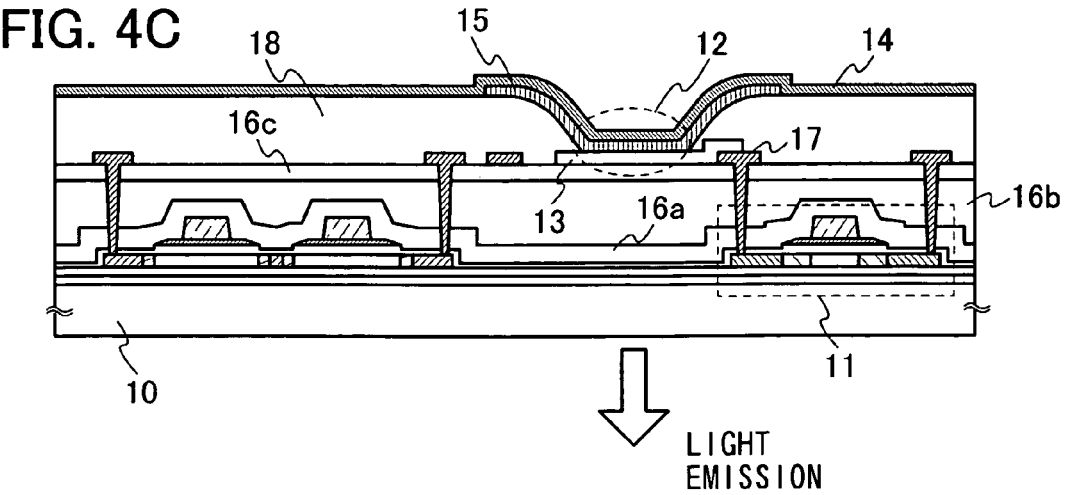

In Embodiment Mode 6, modes of light-emitting devices including the light-emitting element of the present invention are explained with reference to FIGS. 4A to 4C. FIGS. 4A to 4C show cross-sectional views of the light-emitting devices.

In FIGS. 4A to 4C, a portion surrounded by dotted lines of a rectangular shape is a transistor 11 which is provided to drive a light-emitting element 12 of the present invention. The light-emitting element 12 is a light-emitting element of the present invention in which a layer 15 including a light-emitting layer is formed between a first electrode 13 and a second electrode 14, and the light-emitting layer includes an organometallic complex of the present invention. Specifically, the light-emitting element 12 has the structure as shown in Embodiment Mode 2. A drain region of the transistor 11 is electrically connected to the first electrode 13 by a wire 17 penetrating a first interlayer insulating film 16 (16a, 16b, and 16c). The light-emitting element 12 is separated from other adjacently-provided light-emitting elements by a partition layer 18. The light-emitting device having such a structure of the present invention is provided over a substrate 10 in Embodiment Mode 6.

Note that each of the transistors 11 shown in FIGS. 4A to 4C is a top gate type in which a gate electrode is provided on a side opposite to a substrate, regarding the semiconductor layer as a center. However, there are no particular limitations on the structure of the transistor 11; for example, a bottom gate type may be used. In the case of a bottom gate type, the transistor 11 may have a structure in which a protective film is formed over the semiconductor layer forming a channel (a channel protective type) or a structure in which a part of the semiconductor layer forming a channel is depressed (a channel etch type). Note that reference numeral 21 denotes a gate electrode; 22, a gate insulting film; 23, a semiconductor layer; 24, an n-type semiconductor layer; 25, an electrode; and 26, a protective film.

Alternatively, the semiconductor layer included in the transistor 11 may be either crystalline or amorphous. Further, it may be semiamorphous or the like.

Note that the semiamorphous semiconductor is as follows. It has an intermediate structure between an amorphous structure and a crystalline structure (including a single crystal and a polycrystal) and a third state which is stable in terms of free energy, and it includes a crystalline region having short-range order and lattice distortion. At least a part of a region in the film contains a crystal grain of 0.5 nm to 20 nm. A Raman spectrum derived from L-O phonon is shifted to a lower wavenumber side than 520 cm$^{-1}$. Diffraction peaks of (111) and (220) caused by a crystal lattice of silicon are observed in X-ray diffraction. Hydrogen or halogen of at least 1 atomic% is contained to terminate a dangling bond. It is also referred to as a microcrystalline semiconductor. The semiamorphous semiconductor is formed by performing glow discharge decomposition (plasma CVD) on a gas including silicon. SiH$_4$ is given as the gas including silicon. In addition, Si$_2$H$_6$, SiH$_2$Cl$_2$, SiHCl$_3$, SiCl$_4$, SiF$_4$, or the like can also be used as the gas including silicon. The gas including silicon may be diluted with H$_2$, or H$_2$ and one or more rare gas elements of helium (He), argon (Ar), krypton (Kr), and neon (Ne). A dilution ratio thereof may range from 2 times to 1000 times; pressures, approximately 0.1 Pa to 133 Pa; power supply frequency, 1 MHz to 120 MHz, preferably, 13 MHz to 60 MHz. A substrate heating temperature may be 300° C. or less, preferably, 100° C. to 250° C. A concentration of an atmospheric constituent impurity such as oxygen, nitrogen, or carbon, as impurities element in the film, is preferably 1×10$^{20}$/cm$^3$ or less; specifically, a concentration of oxygen is 5×10$^{19}$/cm$^3$ or less, preferably 1×10$^{19}$/cm$^3$ or less. Note that the mobility of a TFT (thin film transistor) using the semiamorphous semiconductor is approximately 1 cm$^2$/sec to 10 cm$^2$/Vsec.

As a specific example of the crystalline semiconductor layer, a layer formed of single crystal or polycrystalline silicon, silicon germanium, or the like can be given. It may be formed by laser crystallization or may be formed by crystallization through a solid phase growth method using, for example, nickel.

When the semiconductor layer is formed of an amorphous substance, for example, amorphous silicon, a light-emitting device preferably has a circuit in which the transistor 11 and the other transistors (transistors included in a circuit for driving a light-emitting element) are all n-channel transistors. Other than this point, a light-emitting device may have a circuit including either n-channel transistors or p-channel transistors, or a display device may have a circuit including both types of transistors.

The first interlayer insulating films 16a to 16c may have a multilayer structure as shown in FIGS. 4A and 4C, or a single-layer structure. Note that the interlayer insulating film 16a is made from an inorganic material such as silicon oxide or silicon nitride; the interlayer insulating film 16b is made from acrylic, siloxane (an organic group including a skeleton of a silicon-oxygen bond (Si—O bond) and including at least hydrogen as a substituent) or a self-planarizing substance which can be formed as a film by an application method, such as silicon oxide. In addition, the interlayer insulating film 16c is made from a silicon nitride film containing argon (Ar). Note that there are no particular limitations on materials forming each layer, and a material other than the foregoing materials may also be used. A layer made from a material other than the foregoing materials may be further combined. As described above, the first interlayer insulating films 16a to 16c may be formed with either an inorganic material or an organic material, or both of them.

The partition layer 18 preferably has a shape in which a curvature radius changes continuously in an edge portion. In addition, the partition layer 18 is formed with acrylic, siloxane, resist, silicon oxide, or the like. Note that the partition layer 18 may be formed with either an inorganic material or an organic material, or both of them.

In FIGS. 4A and 4C, only the first interlayer insulating films 16a to 16c are provided between the transistor 11 and the light-emitting element 12. However, as shown in FIG. 4B, a second interlayer insulating film 19 (19a and 19b) may also be provided in addition to the first interlayer insulating film 16 (16a and 16b). In the light-emitting device shown in FIG. 4B, the first electrode 13 penetrates the second interlayer insulating film 19 and connects to the wire 17.

The second interlayer insulating film 19 may have a multilayer structure or a single-layer structure like the first interlayer insulating film 16. The second interlayer insulating film 19a is made from acrylic, siloxane (an organic group including a skeleton of a silicon-oxygen bond (Si—O bond) and including at least hydrogen as a substituent), or a self-planarizing substance which can be formed as a film by an application method, such as silicon oxide. The second interlayer insulating film 19b is formed from a silicon nitride film containing argon (Ar). Note that there are no particular limitations on materials forming each layer, and a material other than the foregoing materials can also be used. A layer made from a material other than the foregoing materials may be further combined. As described above, the second interlayer insulating film 19 may be formed with either an inorganic material or an organic material, or both of them.

When both the first electrode 13 and the second electrode 14 are formed from light-transmitting materials in the light-emitting element 12, light emission can be extracted through both the first electrode 13 and the second electrode 14 as indicated by the outlined arrows in FIG. 4A. When only the second electrode 14 is formed from a light-transmitting material, light emission can be extracted through only the second electrode 14 as indicated by the outlined arrow in FIG. 4B. In this case, it is preferable to form the first electrode 13 from a highly reflective material or provide a film formed from a highly reflective material (reflective film) below the first electrode 13. When only the first electrode 13 is formed from a light-transmitting material, light emission can be extracted through only the first electrode 13 as indicated by the outlined arrow in FIG. 4C. In this case, it is preferable to form the second electrode 14 from a highly reflective material or provide a reflective film above the second electrode 14.

In the light-emitting element 12, the layer 15 may have such a stacked structure as to operate the light-emitting element 12 when a voltage is applied so that a potential of the second electrode 14 becomes higher than that of the first electrode 13, or the layer 15 may have such a stacked structure as to operate the light-emitting element 12 when a voltage is applied so that a potential of the second electrode 14 becomes lower than that of the first electrode 13. In the former case, the transistor 11 is an n-channel transistor, and in the latter case, the transistor 11 is a p-channel transistor.

As described above, an active light-emitting device in which drive of the light-emitting element is controlled by transistors is explained in this embodiment mode. However, a passive light-emitting device, in which the light-emitting element is driven without providing a particular drive element such as a transistor, may also be employed.

The light-emitting device shown in Embodiment Mode 6 has a feature of realizing various emission colors, since the light-emitting device uses a light-emitting element of the present invention. Further, the light-emitting device also has a feature of emission color with high color purity. Furthermore, the light-emitting device also has a feature of high luminous efficiency and low power consumption.

Embodiment Mode 7

A light-emitting device including the light-emitting element of the present invention can display a preferable image. Therefore, electronic devices that are capable of providing an excellent image can be obtained by applying the light-emitting device of the present invention to display portions of the electronic devices. In addition, the light-emitting device including the light-emitting element of the present invention can be driven with low power consumption because it has excellent luminous efficiency. Therefore, electronic devices with low power consumption can be obtained by applying the light-emitting device of the present invention to the display portions of the electronic devices, and for example, a telephone or the like that has long battery standing time, and the like can be obtained. Hereinafter, some examples of electronic devices incorporating a light-emitting device to which a light-emitting element of the present invention is applied are shown.

Figure 5A:
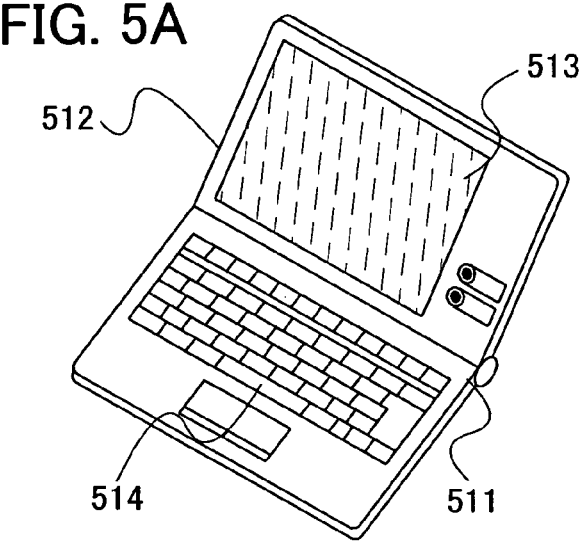
FIGS. 5A to 5C each show an electronic device using a light-emitting device in accordance with an aspect of the present invention.

FIG. 5A is a computer manufactured by applying the present invention, which includes a main body 511, a casing 512, a display portion 513, a keyboard 514, and the like. The computer can be completed by incorporating the light-emitting device including the light-emitting element of the present invention in the display portion.

Figure 5B:
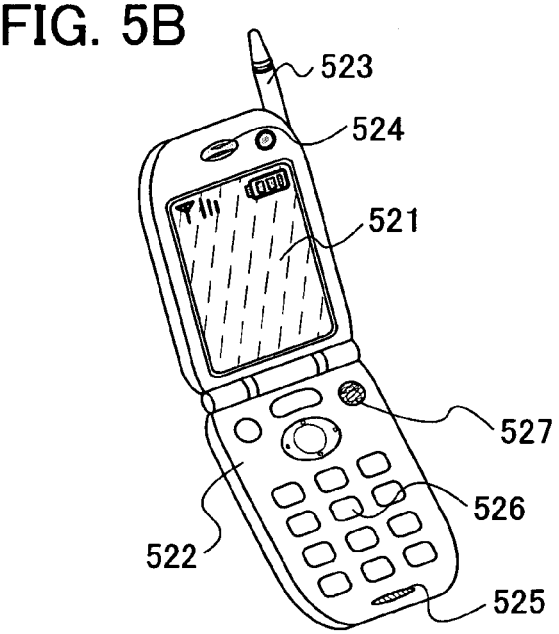

FIG. 5B is a telephone manufactured by applying the present invention, in which a main body 522 includes a display portion 521, an audio output portion 524, an audio input portion 525, operation switches 526 and 527, an antenna 523, and the like. The telephone can be completed by incorporating the light-emitting device including the light-emitting element of the present invention in the display portion.

Figure 5C:
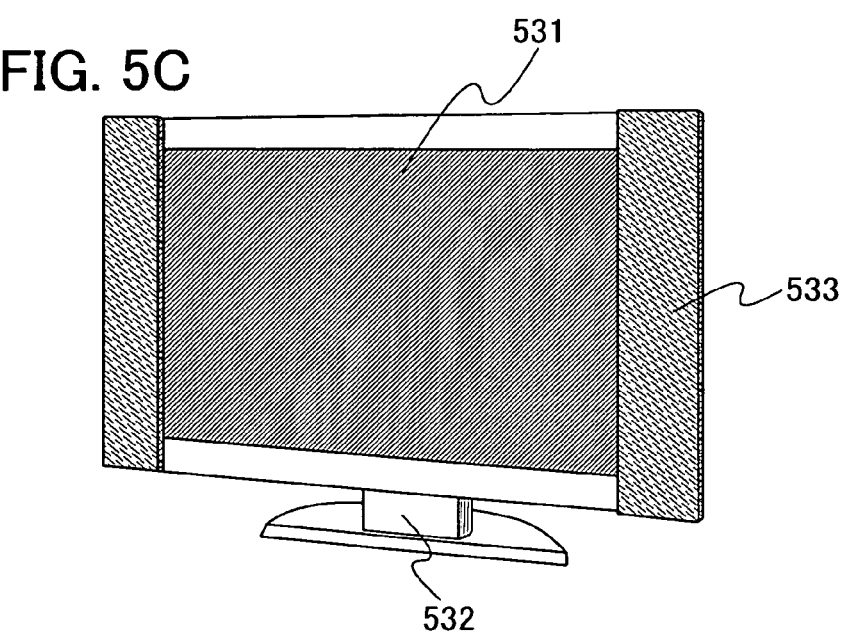

FIG. 5C is a television set manufactured by applying the present invention, which includes a display portion 531, a casing 532, a speaker 533, and the like. The television set can be completed by incorporating the light-emitting device including the light-emitting element of the present invention in the display portion.

As described above, the light-emitting devices of the present invention are extremely suitable for the display portions of various kinds of electronic devices.

Although the computer and the like are described in Embodiment Mode 7, besides, the light-emitting device including the light-emitting element of the present invention may also be incorporated in a navigation system, a lighting apparatus, or the like.

EXAMPLE 1

SYNTHESIS EXAMPLE 1

Synthesis example 1 specifically exemplifies synthesis of an organometallic complex of the present invention represented by the structural formula (1) in Embodiment Mode 1, (acetylacetonato)bis(2-methyl-3-phenylpyrazinato)iridium (III) (abbreviation: [Ir(mppr)$_2$(acac)]).

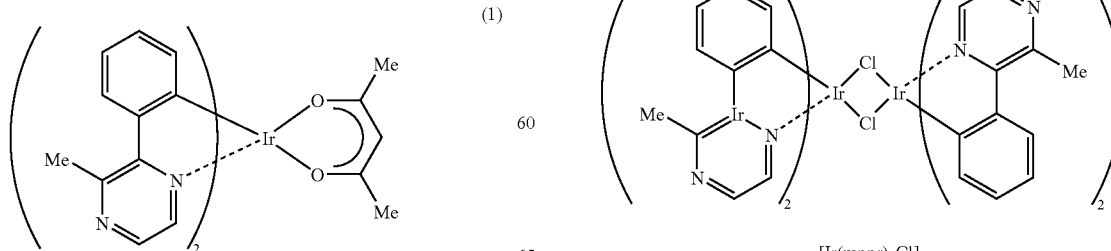

(1)

<Step 1: Synthesis of 2-metyl-3-phenylpyrazine (abbreviation: Hmppr)>

First, in a nitrogen atmosphere, 50 mL of a dibutyl ether solution containing phenyl lithium (produced by Wako Pure Chemical Industries, Ltd, 2.1 mol/L) and 250 mL of diethylether were mixed. Then, 8.98 g of 2-methylpyrazine (produced by Tokyo Chemical Industries Co., Ltd) was dropped into this solution while the solution was being cooled with ice, and stirred at a room temperature for three hours. Water was added into the reacted solution and an organic layer was extracted with diethylether. The obtained organic layer was washed with water and dried with magnesium sulfate. After the solvent was distilled off, the obtained residue was purified by column chromatography using dichloromethane as a developing solvent, thereby obtaining a pyrazine derivative Hmppr (yellow oily matter, yield: 22%). A synthesis scheme of Step 1 is shown by the following (a-1).

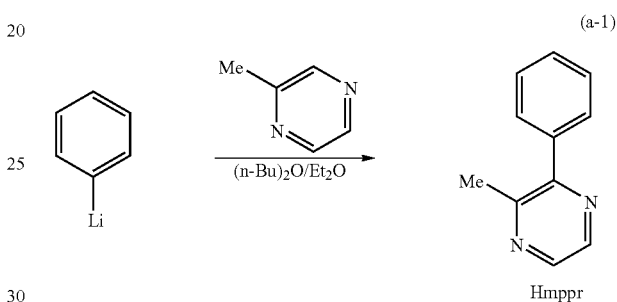

(a-1)

<Step 2: Synthesis of di-μ-chloro-bis [bis(2-methyl-3-phenylpyrazinato)iridium(III)] (abbreviation: [Ir(mppr)$_2$Cl]$_2$)>

Next, 3.61 g of the pyrazine derivative Hmppr obtained in the above step 1 and 2.35 g of iridium chloride hydrate (IrCl$_3$—H$_2$O) (produced by Aldrich Corp.) were mixed in a mixture including 30 mL of 2-ethoxyethanol and 10 mL of water and serving as a solvent, and then refluxed in a nitrogen atmosphere for 15 hours, thereby obtaining a dinuclear complex [Ir(mppr)$_2$Cl]$_2$ (dark green powder, yield: 74%). A synthesis scheme of Step 2 is shown by the following (b-1).

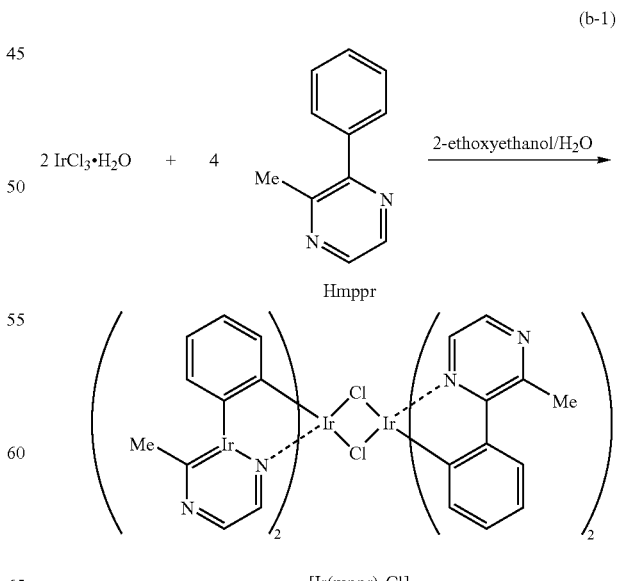

(b-1)

<Step 3: Synthesis of (acetylacetonato)bis(2-methyl-3-phenylpyrazinato)iridium(III) (abbreviation: [Ir(mppr)$_2$(acac)]>

Further, 1.57 g of the dinuclear complex [Ir(mpq)$_2$Cl]$_2$ obtained in the Step 2, 0.43 mL of acetylacetone and 1.47 g of sodium carbonate were mixed in a solvent of 2-ethoxyethanol (60 mL), and refluxed in a nitrogen atmosphere for 16 hours. The reacted solution was cooled naturally to a room temperature and powder obtained by filtrating was recrystallized with dichloromethane, thereby obtaining an organometallic complex [Ir(mppr)$_2$(acac)] of the present invention (orange powder, yield: 26%). A synthesis scheme of Step 3 is shown by the following (c-1).

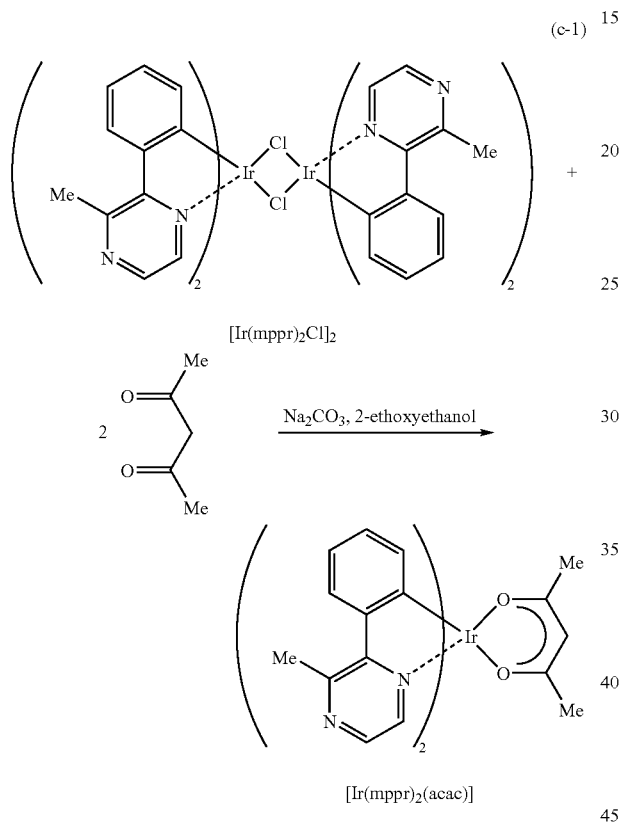

(c-1)

Figure 6A:
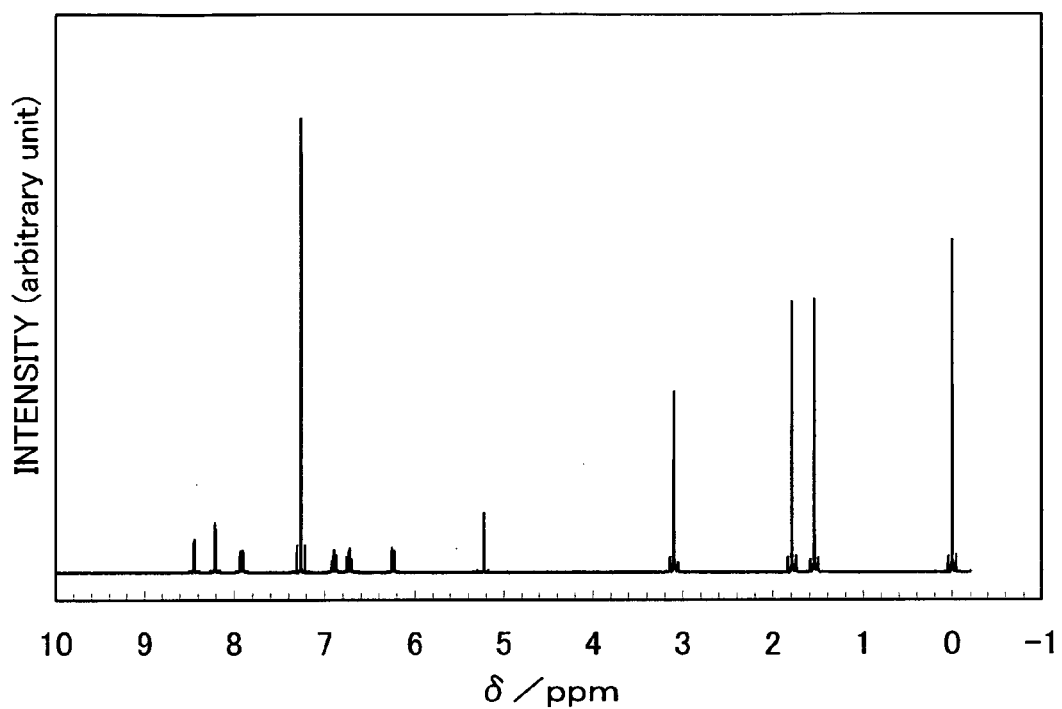
FIGS. 6A and 6B are $^1$H-NMR charts of [Ir(mppr)$_2$(acac)] which is an organometallic complex in accordance with an aspect of the present invention.
Figure 6B:
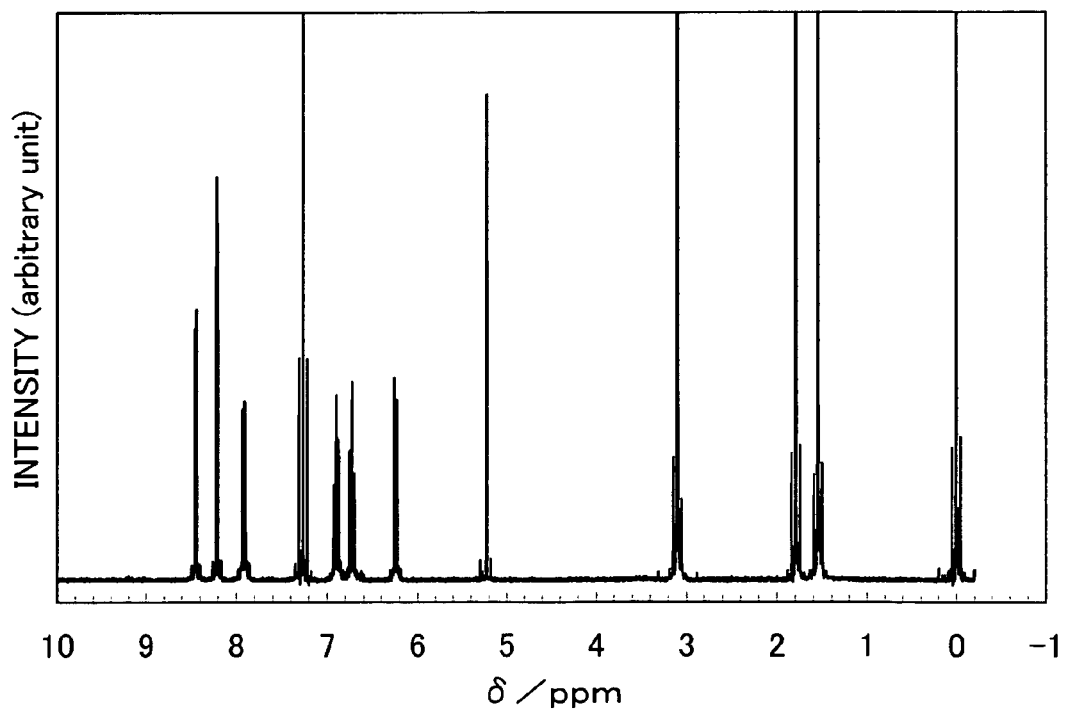

Analysis result of the orange powder obtained in the Step 3 by nuclear magnetic resonance spectrometry ($^1$H-NMR) is shown below. $^1$H-NMR chart is shown in FIGS. 6A and 6B. FIG. 6B shows an enlarged view of FIG. 6A on the vertical axis side. From FIGS. 6A and 6B, it was found that the organometallic complex [Ir(mppr)$_2$(acac)] of the present invention represented by the above structural formula (1) was obtained in this synthesis example 1.

$^1$H-NMR. δ (CDCl$_3$): 1.79 (s, 6H), 3.10 (s, 6H), 5.23 (s, 1H), 6.24 (dd, 2H), 6.73 (td, 2H), 6.90 (td, 2H), 7.92 (d, 2H), 8.21 (d, 2H), 8.42 (d, 2H).

A decomposition temperature T$_d$ of the obtained organometallic complex [Ir(mppr)$_2$(acac)] of the present invention was measured by Thermo-Gravimetric/Differential Thermal Analyzer (manufactured by Seiko Instrument Inc., TG/DTA 320 type), and the result was T$_d$=332° C. It is found that the obtained product showed favorable heat resistance.

Figure 7:
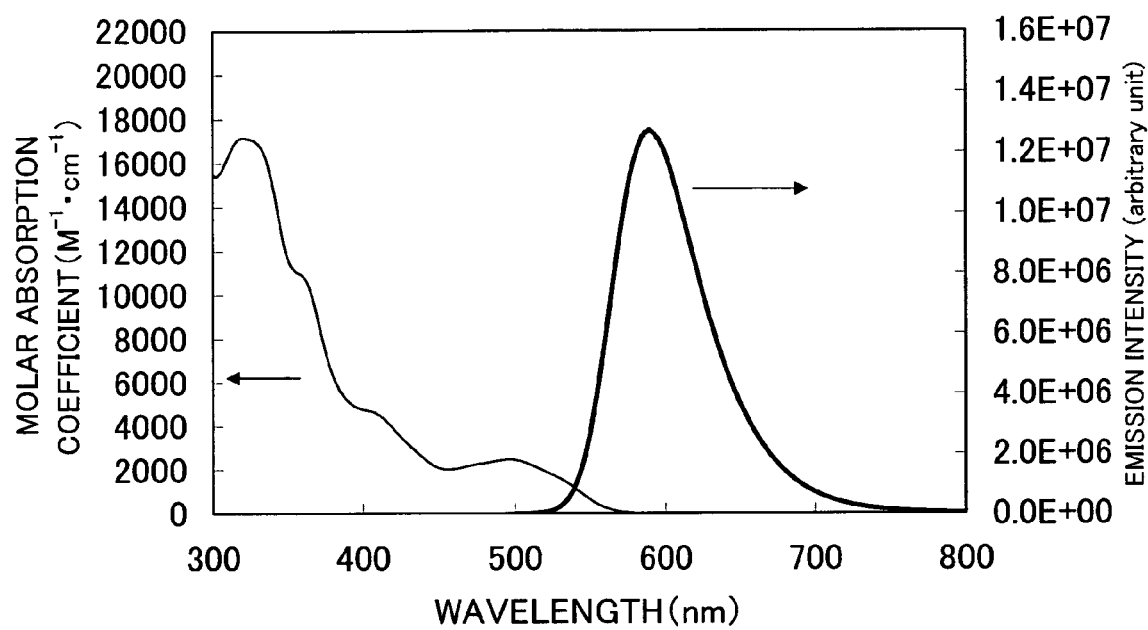
FIG. 7 is a chart showing an absorption spectrum and an emission spectrum of ultraviolet/visible of an organometallic complex [Ir(mppr)$_2$(acac)] which is an organometallic complex in accordance with an aspect of the present invention.

Next, an absorption spectrum and an emission spectrum (excitation wavelength: 468 nm) of [Ir(mppr)$_2$(acac)] were measured by using an ultraviolet-visible light spectrophotometer, (manufactured by Japan Spectroscopy Corporation, V550 type) and a fluorescence spectrophotometer (manufactured by Hamamatsu Photonics Corporation, FS920) respectively. The measurement was conducted by using a degassed dichloromethane solution (0.19 mmol/L) at a room temperature. FIG. 7 shows measurement result. The horizontal axis represents a wavelength and the vertical axis represents a molar absorption coefficient and emission intensity.

As shown in FIG. 7, the organometallic complex [Ir(mppr)$_2$ (acac)] of the present invention has absorption peaks at 320 nm, 360 nm (sh), 408 nm (sh), 496 nm, 536 nm (sh) and 570 nm (sh). In addition, the organometallic complex has a peak of emission spectrum at 598 nm, and exhibits orange light. Full width at half-maximum of the emission spectrum was 70 nm and the spectrum was sharp.

Further, it is observed that the organometallic complex [Ir(mppr)$_2$(acac)] of the present invention has some absorption peaks in a visible light region. This is an absorption unique to some organometallic complexes, which is often observed in an ortho metalation complex or the like, and is considered to correspond to singlet MLCT transition, triplet π-π* transition, triplet MLCT transition, or the like. In particular, the absorption peak on the longest wavelength side spreads toward the bottom broadly in the visible region, which is believed to be triplet MLCT transition. In other words, it was found that [Ir(mppr)$_2$(acac)] which was an organometallic complex of the present invention, was a compound capable of direct photo-excitation to a triplet excited state and intersystem crossing. Therefore, it can be considered that obtained emission was light emission from the triplet excited state, in other words, phosphorescence.

COMPARATIVE EXAMPLE 1

In order to compare emission spectra, a conventional organometallic complex represented by the following structural formula (i), (acetylacetonato)bis(2,3-diphenylpyrazinato)iridium(III) (abbreviation [Ir(dpdp)$_2$(acac)]) was synthesized. Note that this [Ir(dpdp)$_2$(acac)] is a compound disclosed in Reference 2.

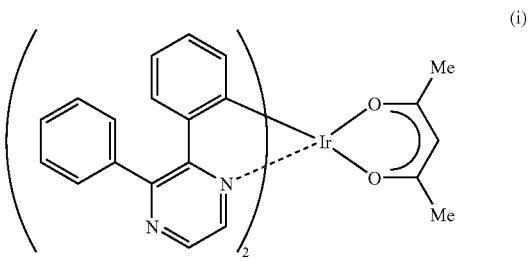

(i)

Figure 8:
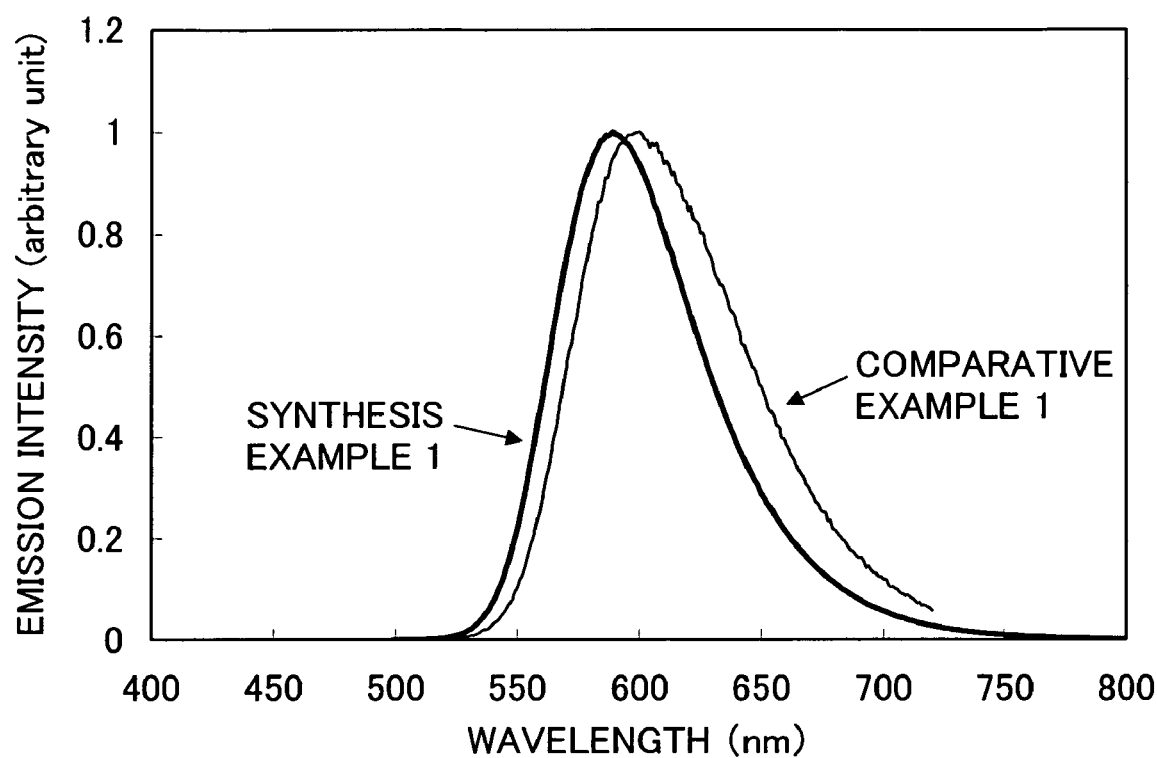
FIG. 8 is a graph showing comparison of emission spectra of Synthesis example 1 and Comparison example 1.

FIG. 8 shows an emission spectrum (excitation wavelength: 468 nm) of [Ir(dphp)$_2$(acac)] in a dichloromethane solution. The horizontal axis denotes a wavelength and the vertical axis denotes emission intensity. FIG. 8 also shows an emission spectrum of [Ir(mppr)$_2$(acac)], an organometallic complex of the present invention which was synthesized in the above synthesis example 1.

As shown in FIG. 8, the full width at half-maximum of an emission spectrum of [Ir(dphp)$_2$(acac)] is 80 nm, and it is found that the spectrum is broader than [Ir(mppr)2(acac)], an organometallic complex of the present invention which was synthesized in the above synthesis example 1.

EXAMPLE 2

Example 2 shows a specific example of a light-emitting element using [Ir(mppr)$_2$(acac)], an organometallic complex of the present invention which was synthesized in the above synthesis example 1 of Example 1, as a luminescent substance. FIG. 1 shows an element structure.

First, a glass substrate over which indium tin oxide including silicon oxide (ITSO) of 110 nm thick had been formed was prepared. The periphery of ITSO surface was covered with an insulating film in such a way that a portion of 2 mm×2 mm of the surface could be exposed. ITSO was formed as a first electrode 101 serving as an anode of the light-emitting element. As a pretreatment for forming the light-emitting element over the substrate, the surface of the substrate was washed with a porous resin brush, and baked at 200° C. for one hour, then, a UV ozone treatment was conducted for 370 seconds.

Then, the substrate was fixed on a holder provided in a vacuum evaporation apparatus such that the surface of the substrate provided with ITSO faces down.

After reducing the pressure of the vacuum evaporation apparatus to $10^{-4}$ Pa, NPB represented by the following structural formula (ii) and molybdenum oxide(VI) were co-evaporated such that NPB: molybdenum oxide(VI)=4:1 (mass ratio) was obtained, thereby forming the hole-injecting layer 111. The thickness of the hole-injecting layer 111 was 50 nm thick. Note that the co-evaporation is an evaporation method in which some different substances are evaporated from some different evaporation sources at the same time. Next, NPB of 10 nm thick was formed by evaporation as the hole-transporting layer 112. Over the hole-transporting layer 112, CBP represented by the following structural formula (iii) and [Ir(mppr)$_2$(acac)] synthesized in Synthesis example 1 were co-evaporated such that CBP: [Ir(mppr)$_2$(acac)]=1:0.05 (mass ratio) was obtained, thereby forming the light-emitting layer 113. The thickness of the light-emitting layer was 30 nm. Then, BCP represented by the following structural formula (iv) of 10 nm thick was deposited by evaporation to form the electron-transporting layer 114. The electron-injecting layer 115 was formed over the electron-transporting layer 114 by co-evaporating Alq$_3$ represented by the following structural formula (v) and lithium (Li) such that Alq$_3$: Li=1:0.01 (mass ratio). The thickness of the electron-injecting layer 115 was 45 nm. Lastly, aluminum of 200 nm was deposited as the second electrode 102 serving as a cathode, and a light-emitting element of the present invention was obtained. Note that in all of the above evaporation steps, a resistance heating method was adopted.

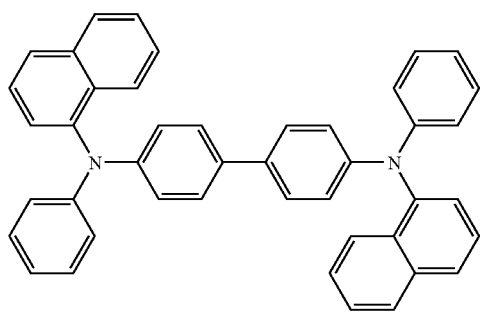

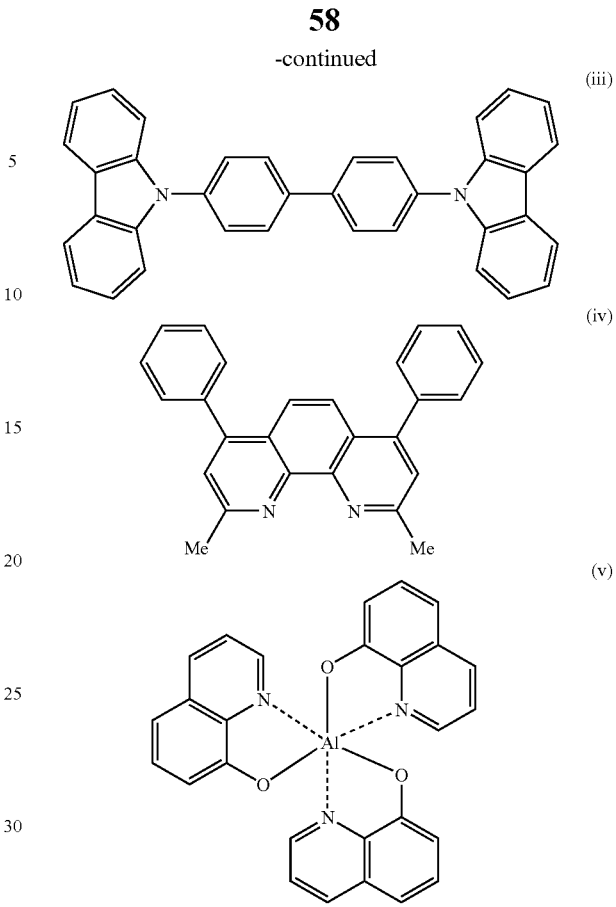

After sealing this light-emitting element in a gloved box with a nitrogen atmosphere so as not to expose the light-emitting element to the air, operation characteristics of the light-emitting element were measured. The measurement was conducted at a room temperature (an atmosphere kept at 25° C.).

Figure 9A:
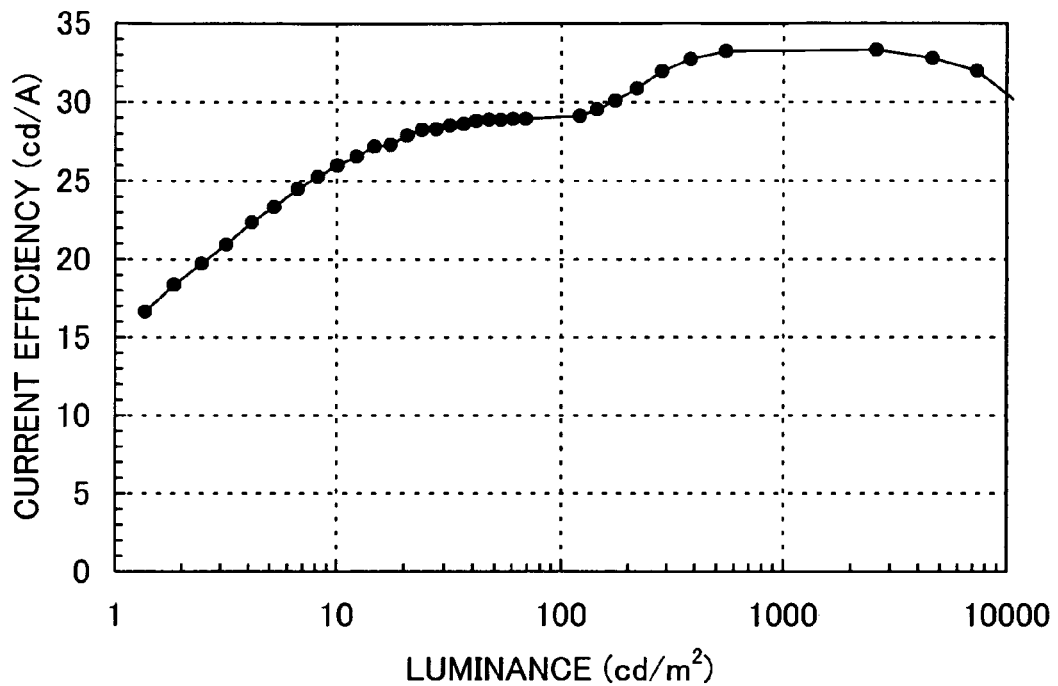
FIGS. 9A and 9B show luminous efficiency of a light-emitting element using [Ir(mppr)$_2$(acac)] which is an organometallic complex in accordance with an aspect of the present invention.
Figure 9B:
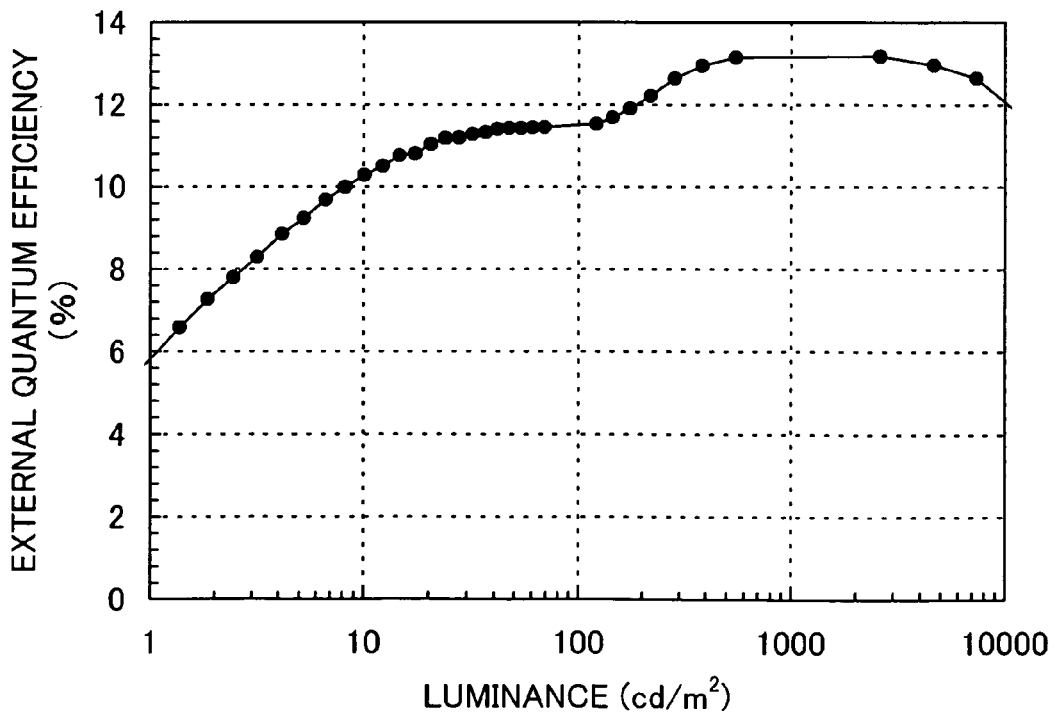
Figure 10:
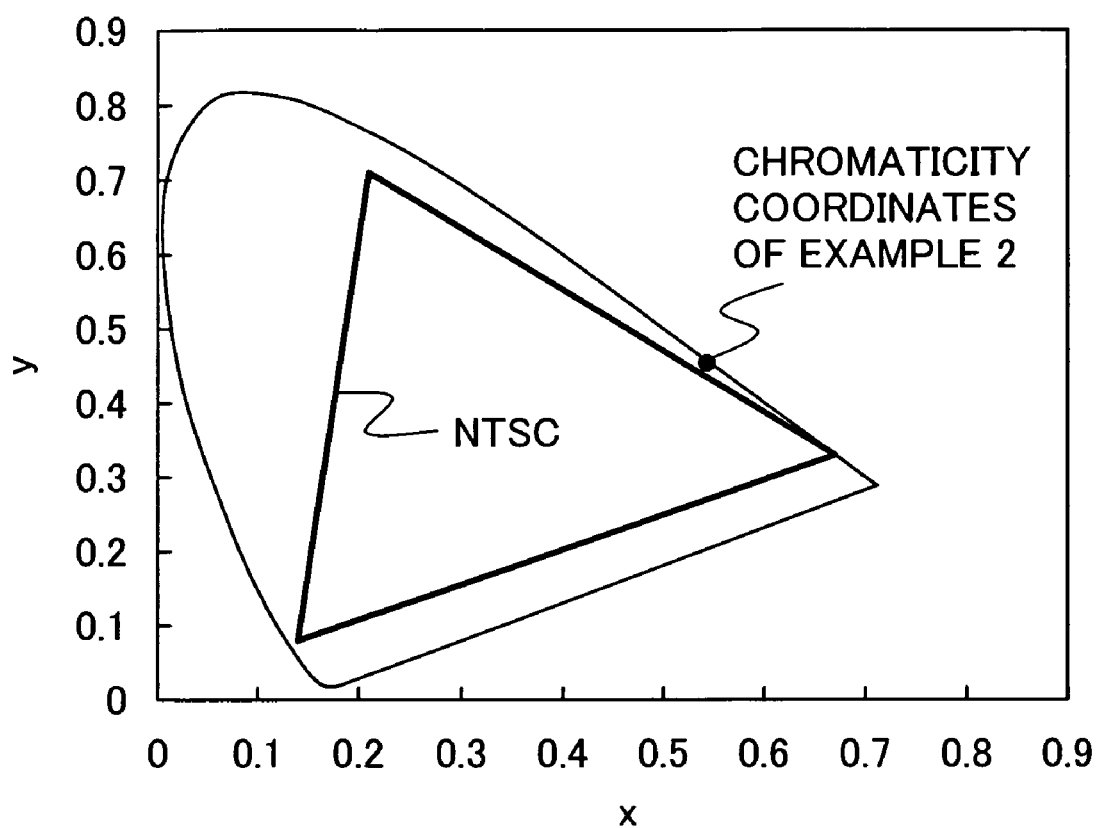
FIG. 10 shows NTSC chromaticity coordinate of a light-emitting element using [Ir(mppr)$_2$(acac)] which is an organometallic complex in accordance with an aspect of the present invention.

FIG. 9A shows luminance-current efficiency characteristics of the light-emitting element, and FIG. 9B is a graph in which the vertical axis of FIG. 9A is converted to external quantum efficiency. This light-emitting element emits light at a luminance of 2600 cd/m$^2$ by allowing current flow with a current density of 7.80 mA/cm$^2$. At this time, the current efficiency was 33.3 cd/A and the external quantum efficiency was 13.2%, and thus, the light-emitting element represented a high luminous efficiency. In addition, FIG. 10 shows CIE chromaticity coordinates at this time and the CIE chromaticity coordinates were (x, y)=(0.54, 0.45). Thus, orange light emission was obtained. As shown in FIG. 10, the CIE chromaticity coordinates of the light-emitting element of this example exist outside the color reproduction region of NTSC standard (which is the inside of the triangle in FIG. 10), and thus, it is known that the light-emitting element exhibits high color purity.

Figure 11:
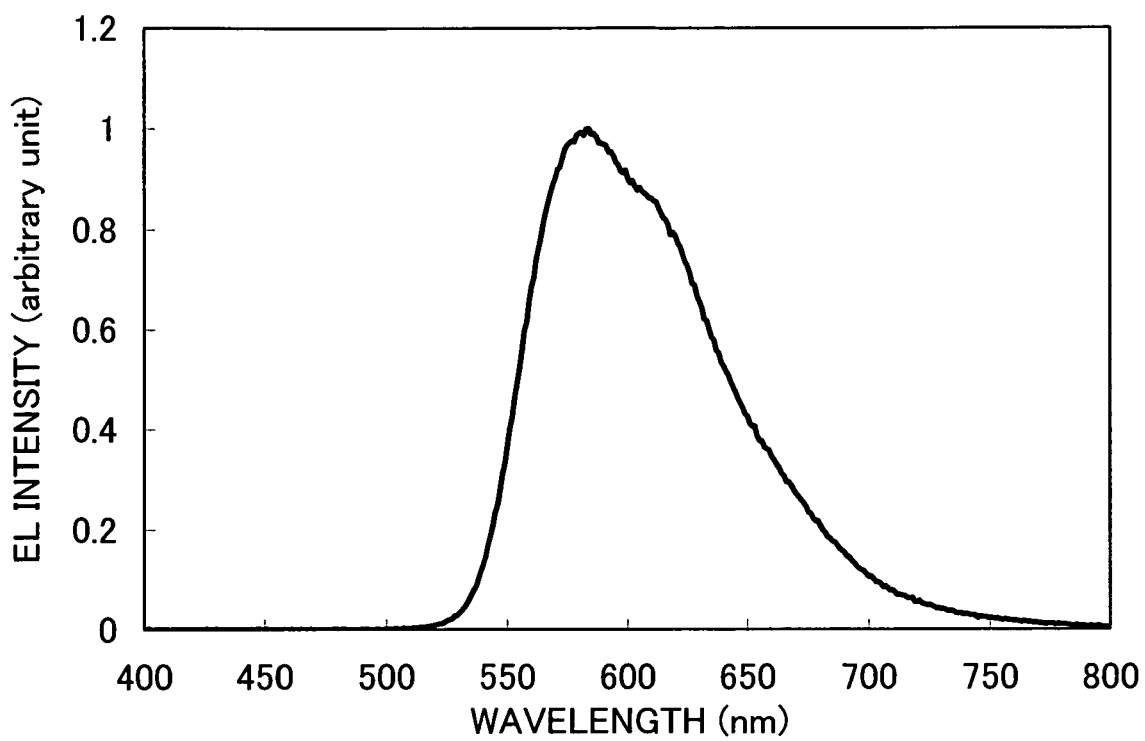
FIG. 11 shows emission spectrum of a light-emitting element using [Ir(mppr)2(acac)] which is an organometallic complex in accordance with an aspect of the present invention.

FIG. 11 shows an emission spectrum when a current at a current density of 25 mA/cm$^2$ was supplied to this light-emitting element. As shown in FIG. 11, the emission spectrum has a peak at 584 nm, and it is indicated that the peak results from emission of [Ir(mppr)2(acac)] which is an organometallic complex of the present invention.

EXAMPLE 3

SYNTHESIS EXAMPLE 2

Synthesis example 2 shows a specific example of synthesis of (acetylacetonato)bis(3,5-dimethyl-2-phenylpyrazinato)iridium(III) (abbreviation: [Ir(mppr-Me)$_2$(acac)]) which is an organometallic complex of the present invention represented by the structural formula (28) in Embodiment Mode 1.

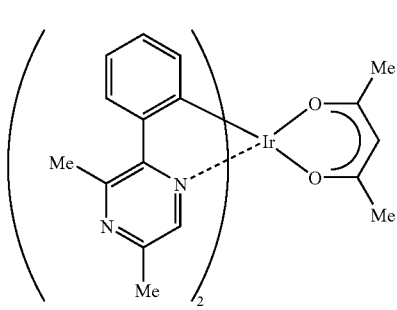

(28)

<Step 1: Synthesis of 3,5-dimethyl-2-phenylpyrazine (abbreviation: Hmppr-Me)>

First, in a nitrogen atmosphere, 50 mL of a dibutylether solution containing phenyl lithium (produced by Wako Pure Chemical Industries, Ltd, 2.1 mol/L) and 250 mL of diethyl ether were mixed. Then, 10.33 g of 2,6-dimethylpyrazine was added into this solution while the solution was being cooled with ice, and stirred at a room temperature for 24 hours. Water was added into this mixture and an organic layer was extracted with diethylether. The obtained organic layer was washed with water and dried with magnesium sulfate. After the drying, the solution was filtrated. After the solvent of the filtrate was distilled off, the obtained residue was purified by silicagel column chromatography using dichloromethane as a developing solvent, thereby obtaining an objective pyrazine derivative Hmppr-Me (reddish brown liquid, yield: 16%). A synthesis scheme of Step 1 is shown by the following (a-2).

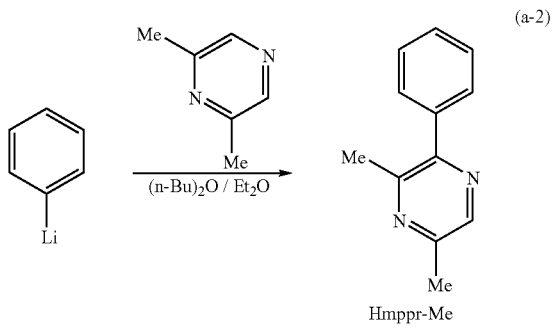

(a-2)

<Step 2: Synthesis of di-µ-chloro-bis[bis(3,5-dimethyl-2-phenylpyrazinato)iridium(III)] (abbreviation: [Ir(mppr-Me)$_2$Cl]$_2$>

Next, 2.88 g of the pyrazine derivative Hmppr-Me obtained in the above step 1 and 1.49 g of iridium chloride hydrate (IrCl$_3$—H$_2$O) (produced by Sigma-Aldrich Corp.) were mixed in a mixture including 30 mL of 2-ethoxyethanol and 10 mL of water and serving as a solvent, then refluxed in a nitrogen atmosphere for 15 hours, and reacted. Powder precipitated from the reacted solution was filtrated and washed with ethanol, thereby obtaining a dinuclear complex [Ir(mppr-Me)$_2$Cl]$_2$ (brown powder, yield: 89%). A synthesis scheme of Step 2 is shown by the following (b-2).

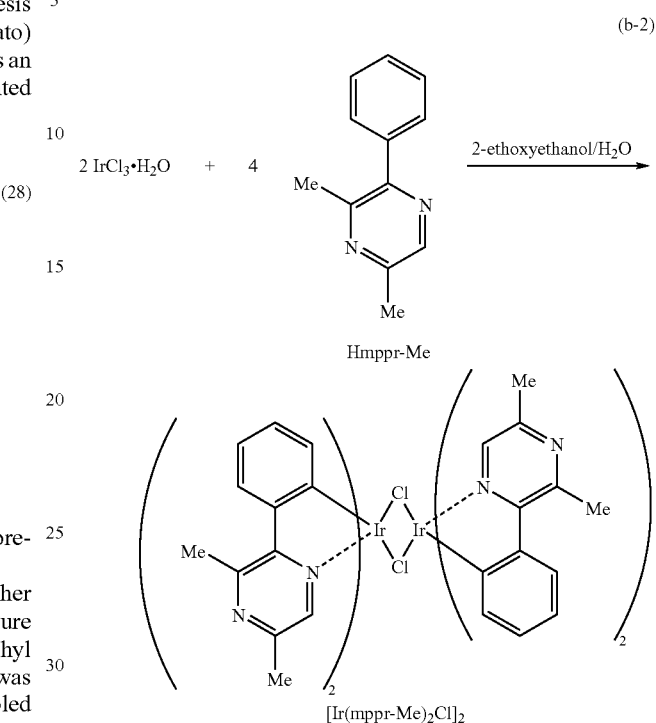

(b-2)

<Step 3: Synthesis of (acetylacetonato)bis(3,5-dimethyl-2-phenylpyrazinato)iridium(III) (abbreviation: [Ir(mppr-Me)$_2$(acac)])>

Further, 1.51 g of the dinuclear complex [Ir(mppr-Me)$_2$Cl]$_2$ obtained in the Step 2, 0.39 mL of acetylacetone and 1.35 g of sodium carbonate were mixed in a solvent of 2-ethoxyethanol (30 mL), and refluxed in a nitrogen atmosphere for 18 hours, and reacted. The reacted solution was cooled naturally to a room temperature and filtrated. The obtained filtrate was washed with ethanol, dissolved in dichloromethane and recrystallized, thereby obtaining an organometallic complex [Ir(mppr-Me)$_2$(acac)] of the present invention (orange powder, yield: 24%). A synthesis scheme of Step 3 is shown by the following (c-2).

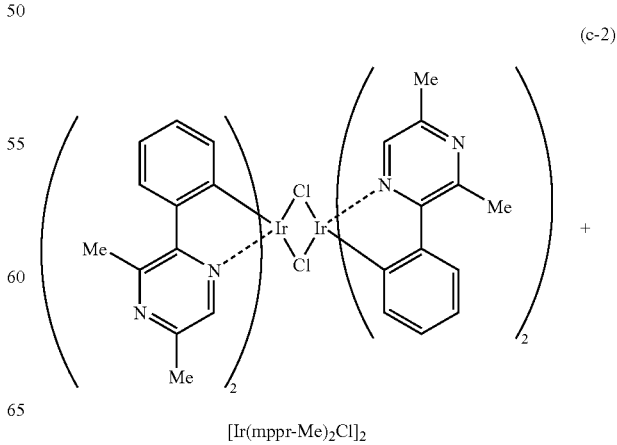

(c-2)

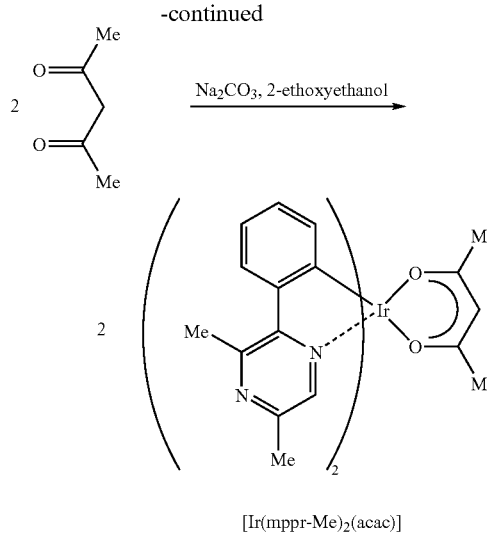

[Ir(mppr-Me)₂(acac)]

Figure 12A:
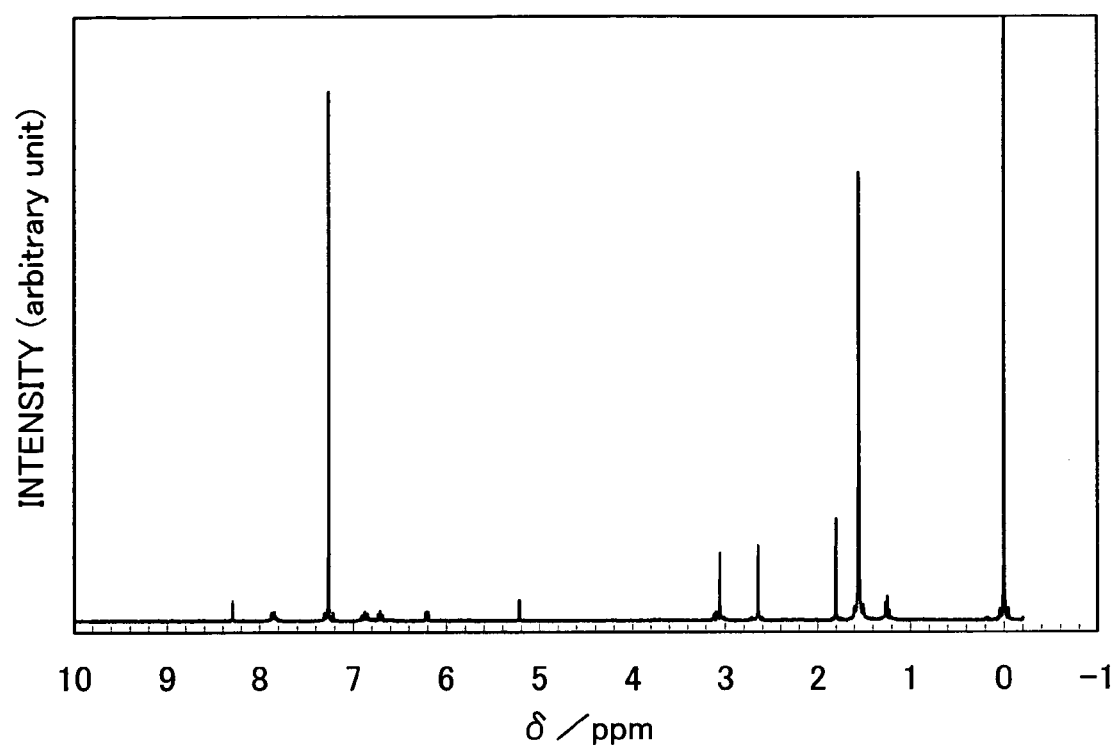
FIGS. 12A and 12B are $^1$H-NMR charts of [Ir(mppr-Me)$_2$(acac)] which is an organometallic complex in accordance with an aspect of the present invention.
Figure 12B:
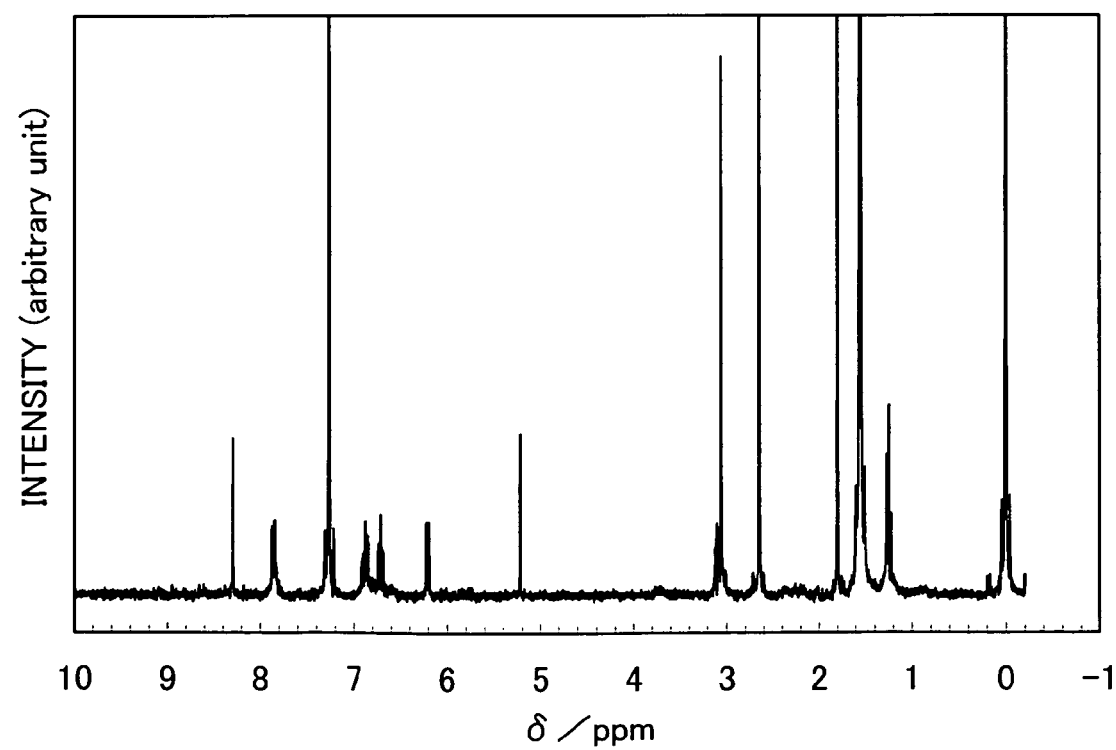

Analysis result of the orange powder obtained in the Step 3 by nuclear magnetic resonance spectrometry ($^1$H-NMR) is shown below. $^1$H-NMR chart is shown in FIGS. 12A and 12B. FIG. 12B shows an enlarged view of FIG. 12A on the vertical axis side. From FIGS. 12A and 12B, it was found that the organometallic complex [Ir(mppr-Me)₂(acac)] of the present invention represented by the above structural formula (28) was obtained in this synthesis example 1.

$^1$H-NMR. δ (CDCl₃):1.80 (s, 6H), 2.65 (s, 6H), 3.09 (s, 6H), 5.22 (s, 1H), 6.21 (dd, 2H), 6.70 (td, 2H), 6.87 (td, 2H), 7.86 (d, 2H), 8.29 (s, 2H).

Thermo-Gravimetric/Differential Thermal Analysis (TG-DTA) measurement of 15 the obtained organometallic complex [Ir(mppr-Me)₂(acac)] of the present invention was conducted. The measurement was conducted by using a high vacuum differential type differential thermal balance (manufactured by Bruker AXS K. K., TG/DTA 2410SA). The measurement was carried out in a nitrogen atmosphere under a normal pressure. From the relation of gravity and temperature (thermogravimetric measurement), the temperature when the gravity becomes 95% or less with respect to the gravity at the start of the measurement, was 292° C., and it was found that an excellent heat resistance was exhibited.

Figure 13:
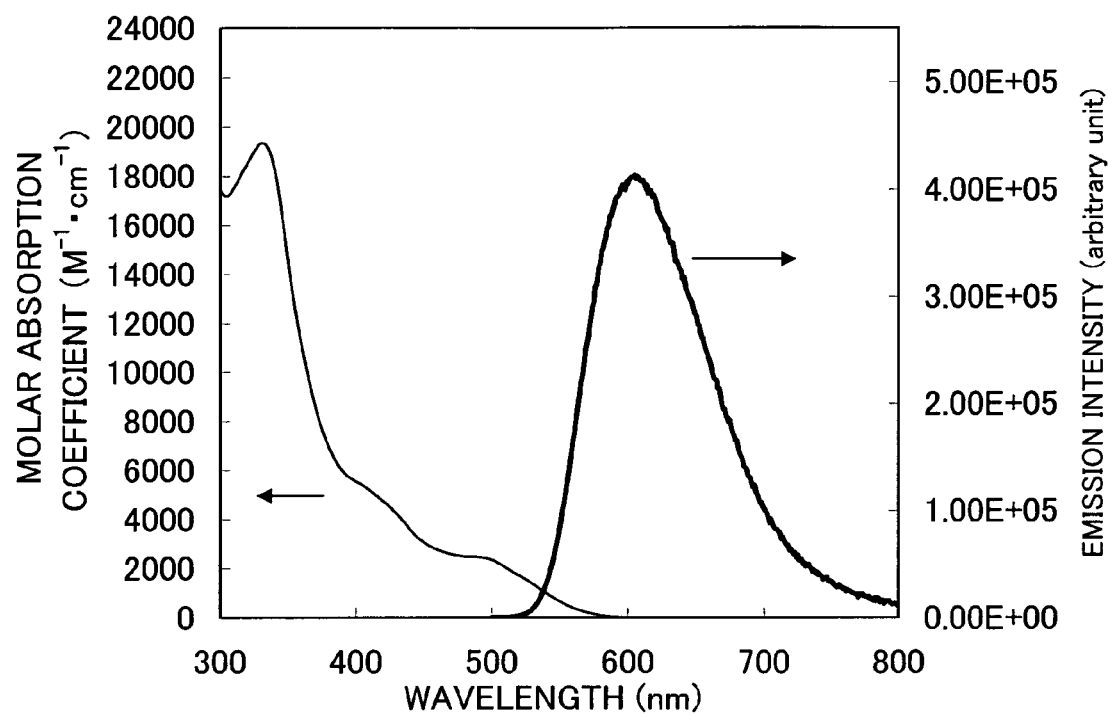
FIG. 13 is a chart showing an absorption spectrum and an emission spectrum of ultraviolet/visible of [Ir(mppr-Me)$_2$(acac)] which is an organometallic complex in accordance with an aspect of the present invention.

Then, an absorption spectrum of [Ir(mppr-Me)₂(acac)] was measured by an ultraviolet-visible light spectrophotometer, (manufactured by Japan Spectroscopy Corporation, V550 type). The measurement was conducted at a room temperature after adjusting and degassing a dichloromethane solution (0.13 mmol/L) of [Ir(mppr-Me)₂(acac)]. In addition, an emission spectrum (excitation wavelength: 465 nm) of [Ir(mppr-Me)₂(acac)] was measured by a fluorescence spectrophotometer (manufactured by Hamamatsu Photonics Corporation, FS920). The measurement was conducted at a room temperature after adjusting and degassing a dichloromethane solution (0.47 mmol/L) of [Ir(mppr-Me)₂(acac)]. FIG. 13 shows measurement result. The horizontal axis represents a wavelength and the vertical axis represents a molar absorption coefficient and emission intensity.

As shown in FIG. 13, it is found that the organometallic complex [Ir(mppr-Me)₂(acac)] of the present invention has an emission peak at 605 nm and exhibits reddish-orange light emission.

EXAMPLE 4

Example 4 specifically exemplifies a light-emitting element using as a luminescent substance, the organometallic complex of the present invention which was synthesized in Synthesis example 2 of Example 3, [Ir(mppr-Me)₂(acac)]. FIG. 1 shows the element structure.

The element structure was obtained in a similar manner to that in Example 2, except that a light-emitting layer 113 has the following structure. The light-emitting layer 113 was formed by co-evaporating CBP and [Ir(mppr-Me)₂(acac)] synthesized in Synthesis example 2 such that CBP: [Ir(mppr-Me)₂(acac)]=1:0.06 (mass ratio) was obtained. The thickness was 30 nm.

After sealing this light-emitting element in a gloved box with a nitrogen atmosphere so as not to expose the light-emitting element to the air, operation characteristics of the light-emitting element were measured. The measurement was conducted at a room temperature (an atmosphere kept at 25° C.).

Figure 14:
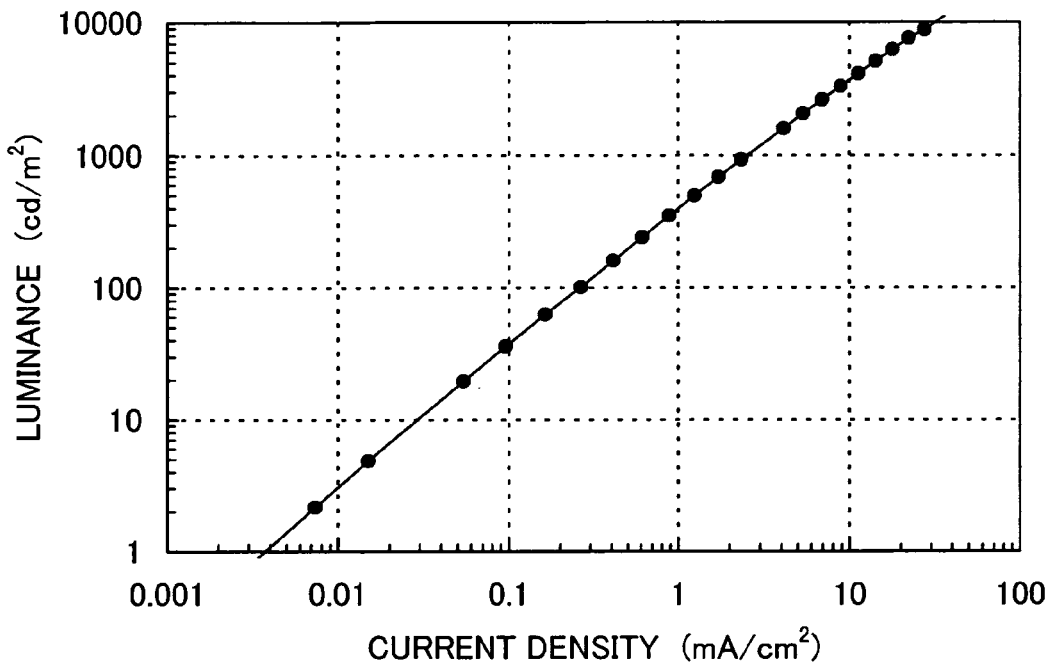
FIG. 14 shows current density-luminance characteristics of a light-emitting element using [Ir(mppr-Me)$_2$(acac)] which is an organometallic complex in accordance with an aspect of the present invention.
Figure 15:
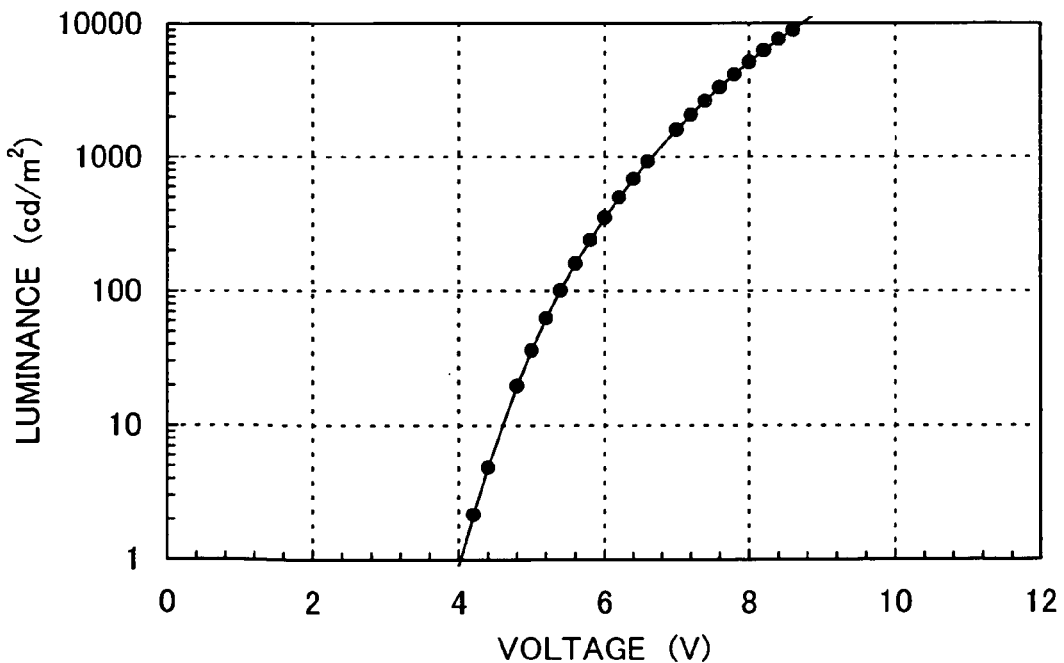
FIG. 15 shows voltage-luminance characteristics of a light-emitting element using [Ir(mppr-Me)$_2$(acac)] which is an organometallic complex in accordance with an aspect of the present invention.
Figure 16A:
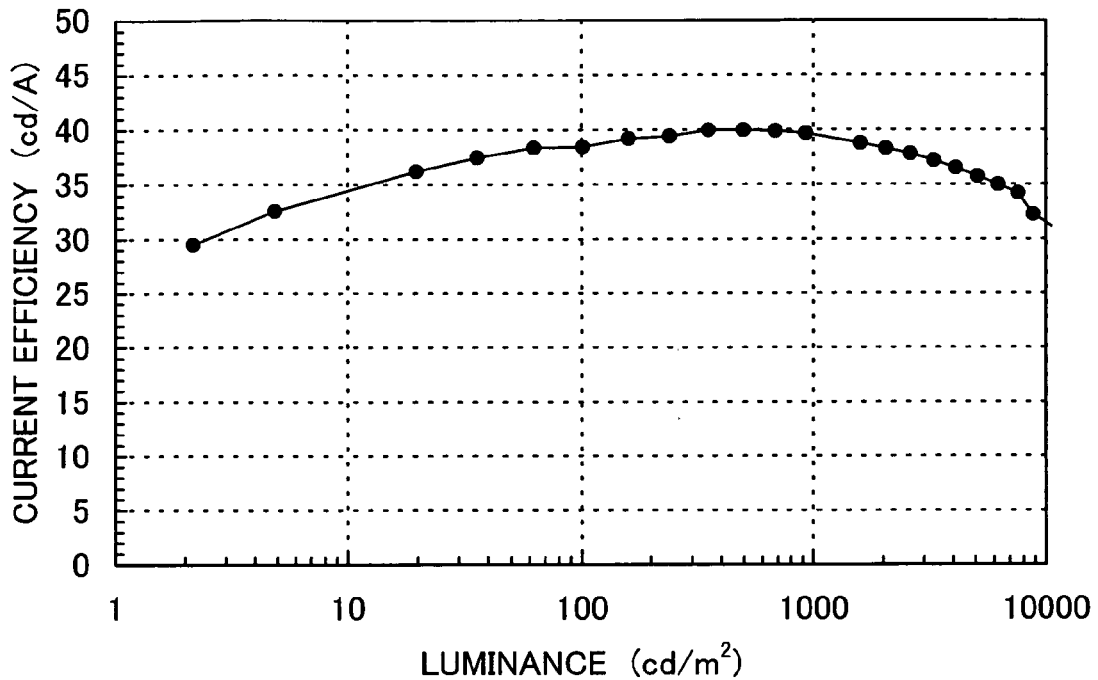
FIGS. 16A and 16B show luminous efficiency of a light-emitting element using [Ir(mppr-Me)$_2$(acac)] which is an organometallic complex in accordance with an aspect of the present invention.
Figure 16B:
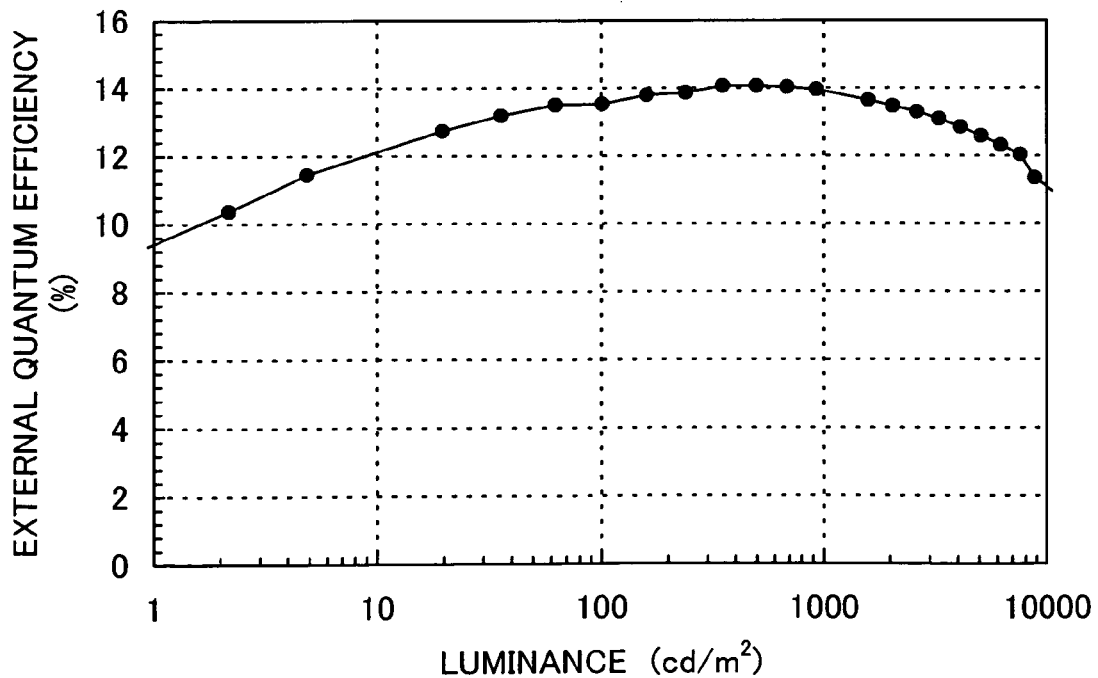

FIG. 14 and FIG. 15 show luminance-current density characteristics, and voltage-luminance characteristics, respectively. This light-emitting element emits light at a luminance of 2600 cd/m² by applying a voltage of 7.4 V thereto to allow current to flow with a current density of 6.94 mA/cm². FIG. 16A shows luminance-current efficiency characteristics, and FIG. 16B is a graph in which the vertical axis of FIG. 9A is converted to external quantum efficiency. The current efficiency was 37.8 cd/A and the external quantum efficiency was 13.3% when light was emitted at a luminance of 2600 cd/m². It is known that high luminous efficiency was exhibited. In addition, CIE chromaticity coordinates at this time were (x, y )=(0.53, 0.47), and it was yellow orange light.

Figure 17:
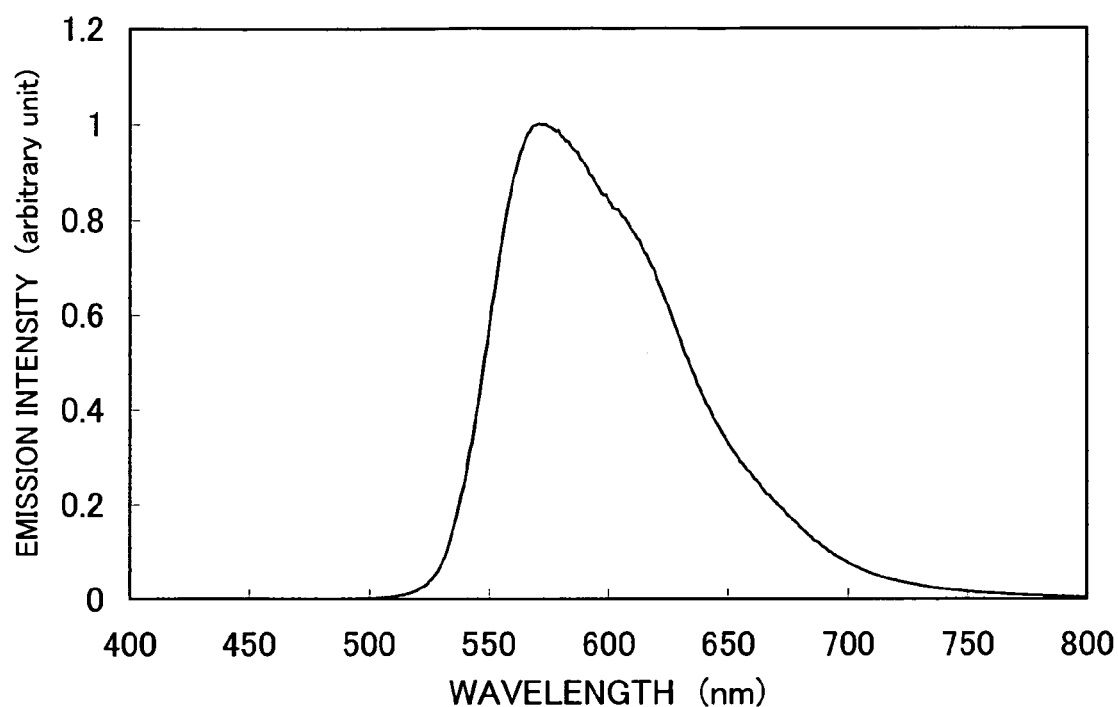
FIG. 17 shows an emission spectrum of a light-emitting element using [Ir(mppr-Me)$_2$(acac)] which is an organometallic complex in accordance with an aspect of the present invention.

FIG. 17 shows an emission spectrum when a current at a current density of 25mA/cm² was supplied to this light-emitting element. As shown in FIG. 17, the emission spectrum has a peak at 571 nm, and it is indicated that the peak results from emission of [Ir(mppr-Me)₂(acac)] which is an organometallic complex of the present invention. The light-emitting element of Example 4 has an emission spectrum which is shifted to a short wavelength by about 13 nm as compared with the light-emitting element of Example 2. In this manner, as for the organometallic complex of the present invention, adjustment of emission color can be made easily by molecular design.

EXAMPLE 5

SYNTHESIS EXAMPLE 3

In Synthesis example 3, synthesis of an organometallic complex of the present invention represented by the structural formula (57), (acetylacetonato)bis(5-isopropyl-3-methyl-2-phenylpyrazinato)iridium(III) (abbreviation: [Ir(mppr-iPr)₂(acac)]) will be exemplified specifically.

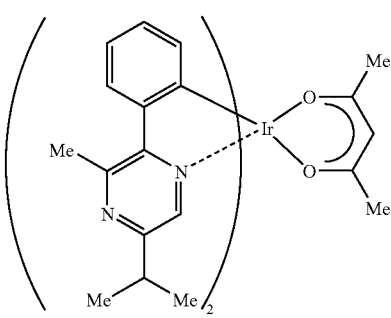

(57)

<Step 1: Synthesis of 5-isopropyl-3-methyl-2-phenylpyrazine (abbreviation Hmppr-iPr)>

20 mL of dehydrated ethanol, 2.22 g of 1-phenyl-1,2-propanedione and 0.90 g of anhydrous ethylenediamine were put in an eggplant flask with a reflux pipe, and the inside air of the flask was substituted by argon. Then, it was irradiated with microwave (2.45 GHz, 1 to 100W) for 10 minutes and reacted. Then, into this reacted solution, 2.20 mL of acetone and 1.01 g of potassium hydroxide were added, and irradiated with microwave (2.45 GHz, 1 to 100 W) for 20 minutes. Water was added into this mixture and an organic layer was extracted with ethyl acetate. The obtained organic layer was washed with water and dried with magnesium sulfate. The solution after drying was filtrated and a solvent of the filtrate was distilled off. The obtained residue was purified by silica-gel column chromatography using dichloromethane as a developing solvent, thereby obtaining an objective pyrazine derivative Hmppr-iPr (orange liquid, yield: 35%). For the irradiation of microwave, a microwave synthesis system (Discovery, manufactured by CEM Corporation) was used. A synthesis scheme of Step 1 is shown by the following (a-3).

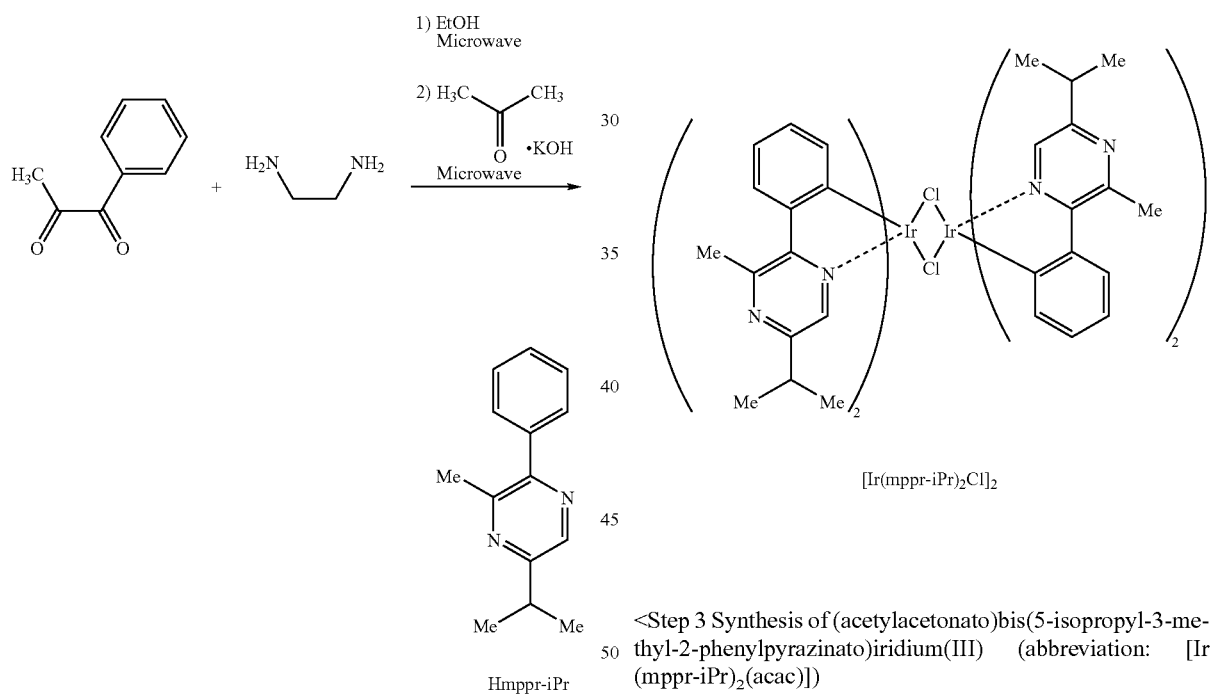

<Step 2: Synthesis of di-μ-chloro-bis[bis(5-isopropyl-3-methyl-2-phenylpyrazinato)iridium(III)](abbreviation: [Ir(mppr-iPr)$_2$Cl]$_2$>

Next, 24 mL of 2-ethoxyethanol, 8 mL of water, 1.12 g of the pyrazine derivative Hmppr-iPr obtained the above step 1 and 0.72 g of iridium chloride hydrate (IrCl$_3$—H$_2$O) (produced by Aldrich Corp.) were put in an eggplant flask with a reflux pipe and the inside air of the flask was substituted by argon. Then, it was irradiated with microwave (2.45 GHz, 150 W) for 30 minutes and reacted. The powder precipitated from the reacted solution was filtrated and washed with ethanol thereby obtaining a dinuclear complex [Ir(mppr-iPr)$_2$Cl]$_2$ (dark orange powder, yield: 52%). A synthesis scheme of Step 2 is shown by the following (b-3).

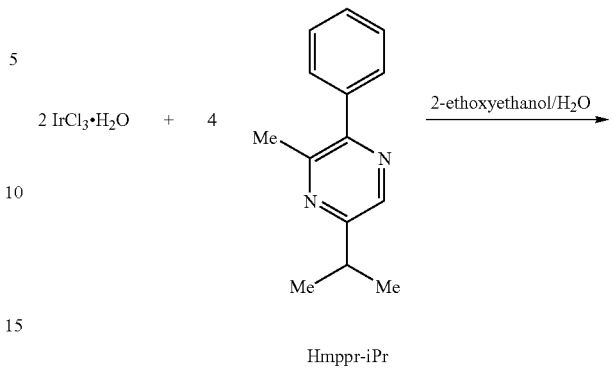

<Step 3 Synthesis of (acetylacetonato)bis(5-isopropyl-3-methyl-2-phenylpyrazinato)iridium(III) (abbreviation: [Ir(mppr-iPr)$_2$(acac)])

Further, 30 mL of 2-ethoxyethanol, 0. 81 g of the dinuclear complex [Ir(mppr-iPr)$_2$Cl]$_2$ obtained in the above step 2, 0.19 mL of acetylacetone and 0.66 g of sodium carbonate were put in an eggplant flask with a reflux pipe and the inside air of the flask was substituted by argon. Then, it was irradiated with microwave (2.45 GHz, 150 W) for 30 minutes and reacted. The reacted solution was cooled naturally to a room temperature and filtrated. The obtained filtrate was concentrated and hardened by drying, and the precipitated residue was recrystallized with ethanol, thereby obtaining [Ir(mppr-iPr)$_2$C(acac)] which was an organometallic complex of the present invention (orange microcrystal, yield: 57%). A synthesis scheme of Step 3 is shown by the following (c-3).

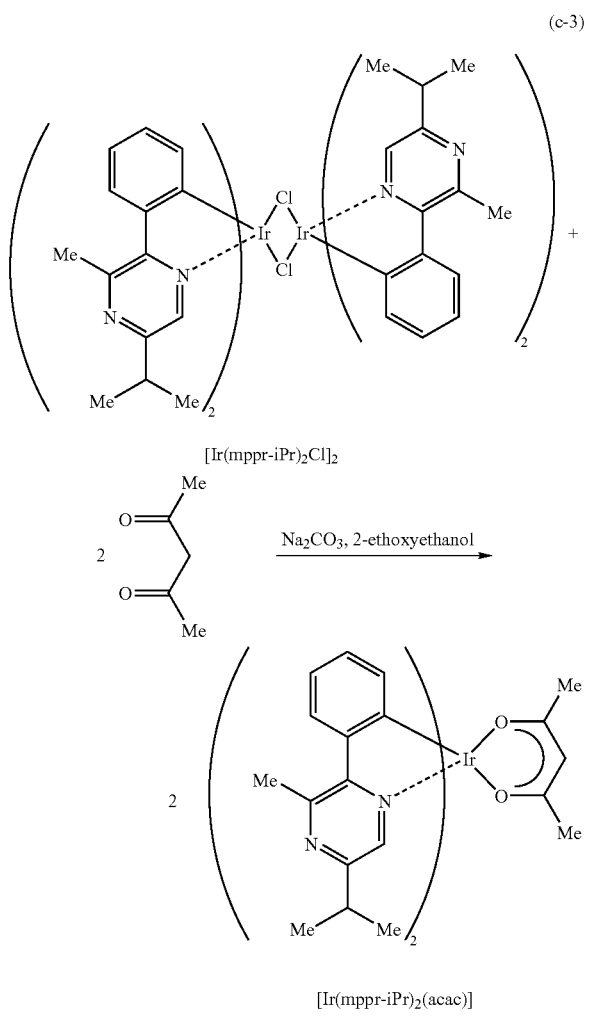

[Ir(mppr-iPr)₂Cl]₂

Na₂CO₃, 2-ethoxyethanol

[Ir(mppr-iPr)₂(acac)]

Figure 18A:
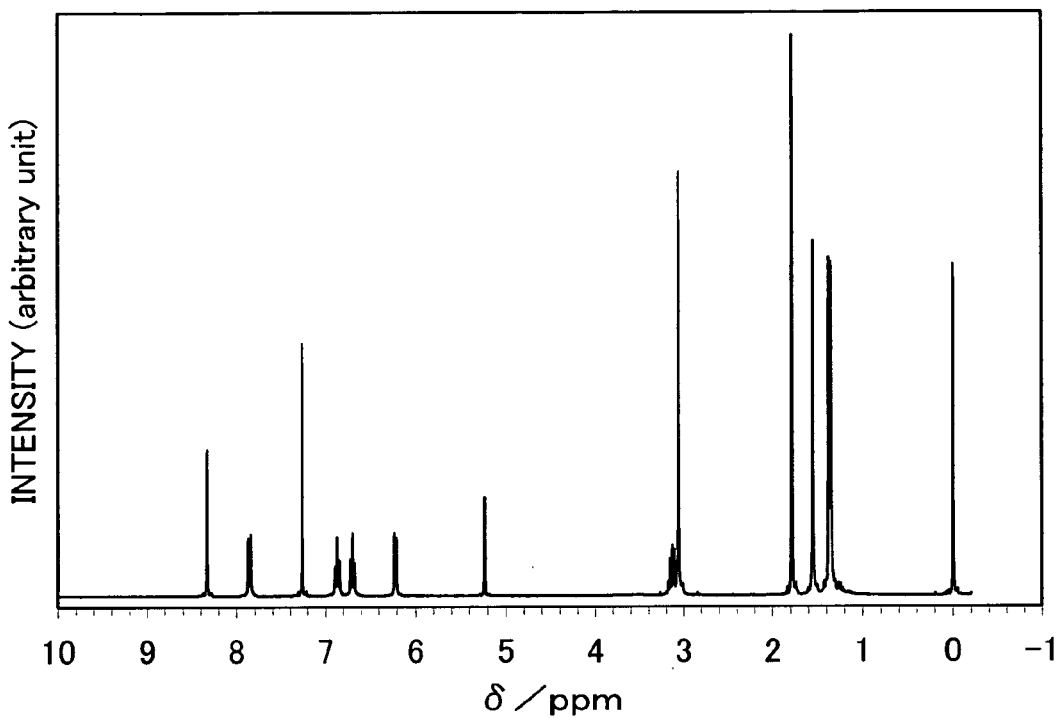
FIGS. 18A and 18B are $^1$H-NMR charts of [Ir(mppr-iPr)$_2$(acac)] which is an organometallic complex in accordance with an aspect of the present invention.
Figure 18B:
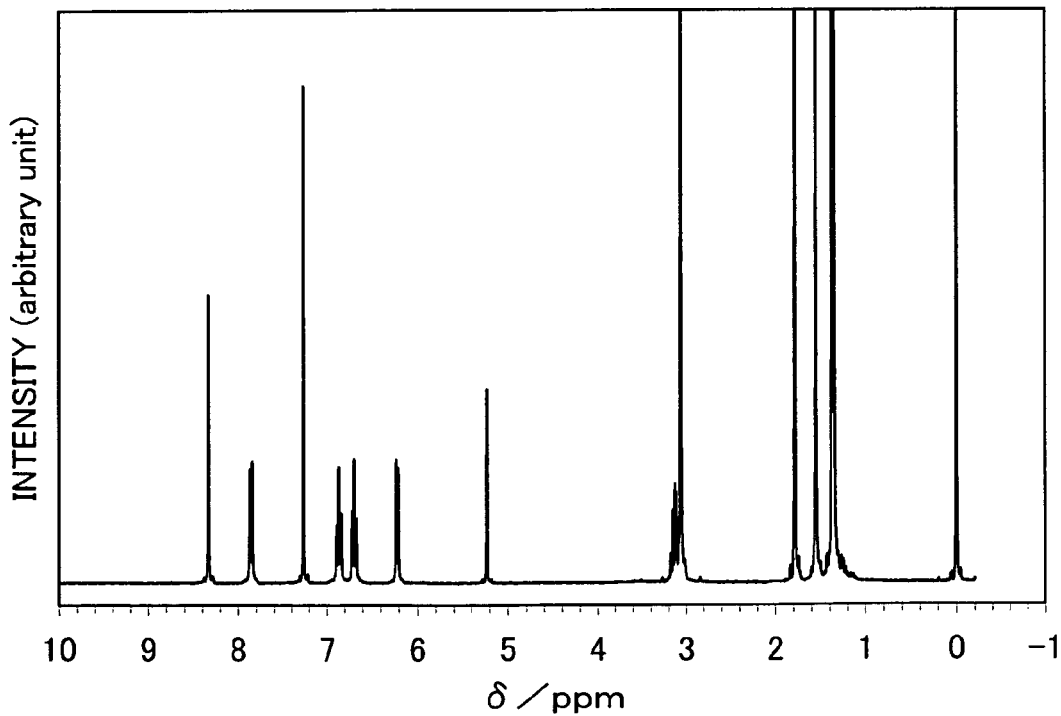

Analysis result of the orange powder obtained in the Step 3 by nuclear magnetic resonance spectrometry (¹H-NMR) is shown below. ¹H-NMR chart is shown in FIGS. 18A and 18B. FIG. 18B shows an enlarged view of FIG. 18A in the vertical axis side. From FIGS. 18A and 18B, it was found that the organometallic complex [Ir(mppr-iPr)₂C(acac)] of the present invention represented by the above structural formula (57) was obtained in this synthesis example 3.

¹H-NMR. δ (CDCl₃): 1.36 (m, 12H), 1.79 (s, 6H), 3.06 (s, 6H), 3.13 (m, 2H), 5.23 (s, 1H), 6.22 (d, 2H), 6.70 (td, 2H), 6.87 (t, 2H), 7.86 (d, 2H), 8.33 (s, 2H).

Decomposition temperature of the obtained organometallic complex [Ir(mppr-iPr)₂C(acac)] of the present invention was measured. The measurement was conducted by a high vacuum differential type differential thermal balance (manufactured by Bruker AXS K. K., TG/DTA 2410SA). The rising temperature was set 10° C./min and the temperature was raised. When the temperature was 300° C., 5% of gravity reduction was seen and it was found that the organometallic complex exhibited excellent heat resistance.

Figure 19:
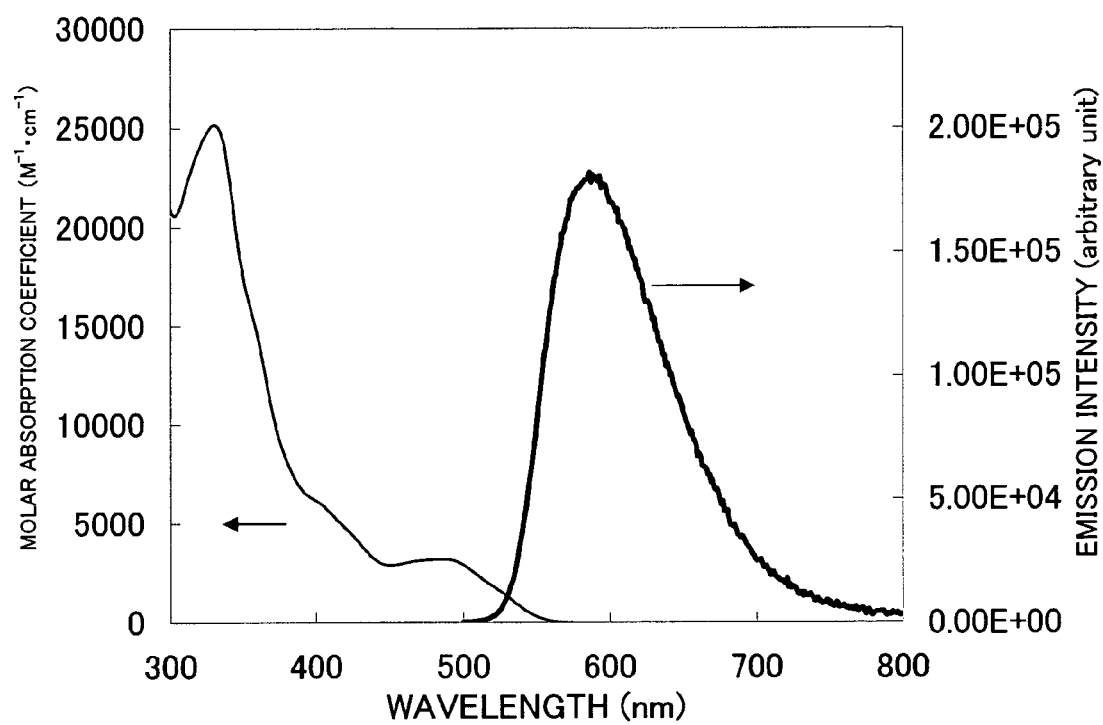
FIG. 19 is a chart showing an absorption spectrum and an emission spectrum of ultraviolet/visible of [Ir(mppr-iPr)$_2$(acac)] which is an organometallic complex in accordance with an aspect of the present invention.

Subsequently, an absorption spectrum of [Ir(mppr-iPr)₂(acac)] was measured by an ultraviolet-visible light spectrophotometer, (manufactured by Japan Spectroscopy Corporation, V550 type). The measurement was conducted at a room temperature by using a dichloromethane solution (0.11 mmol/L). In addition, an emission spectrum of [Ir(mppr-iPr)₂(acac)] (excitation wavelength: 467 nm) was measured. The measurement of the emission spectrum was conducted by a fluorescence spectrophotometer (manufactured by Hamamatsu Photonics Corporation, FS920) using the degassed dichloromethane solution (0.41 mmol/L) at a room temperature. FIG. 19 shows measurement result. The horizontal axis represents a wavelength and the vertical axis represents a molar absorption coefficient and emission intensity.

As shown in FIG. 19, it is found that the organometallic complex [Ir(mppr-iPr)₂(acac)] of the present invention has an emission peak at 586 nm and the solution exhibits orange light emission.

The present application is based on Japanese Patent application No. 2005-350807 filed on Dec. 5, 2005 in the Japanese Patent Office, the entire contents of which are hereby incorporated by reference.

The invention claimed is:
1. An organometallic complex comprising a structure represented by a general formula (G10):

(G10)

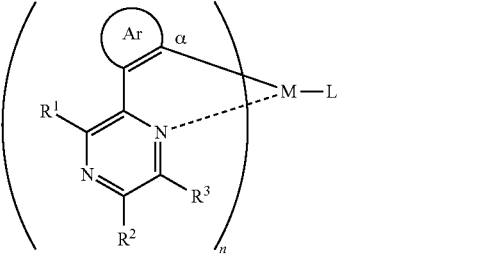

(G7)

(G8)

(G9)

wherein $R^1$ represents an alkyl group having 1 to 4 carbon atoms; $R^2$ and $R^3$ each represent any one of hydrogen and an alkyl group having 1 to 4 carbon atoms; Ar represents any one of formulas (G7) to (G9); $R^7$ and $R^8$ each represent an alkyl group having 1 to 4 carbon atoms; M is a center metal selected from Group 9 element; α represents a position of carbon which bonds the center metal in the arylene group; L represents a monoanionic ligand; and n is 2;

wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

2. The organometallic complex according to claim 1, wherein the monoanionic ligand is represented by any one of (L1) to (L8)

(L1) 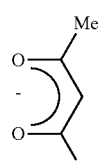

(L2) 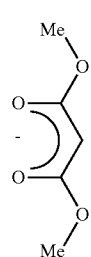

(L3) 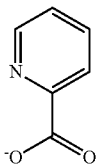

(L4) 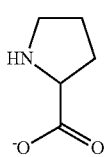

(L5) 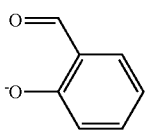

(L6) 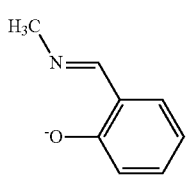

(L7) 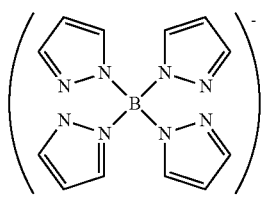

(L8) 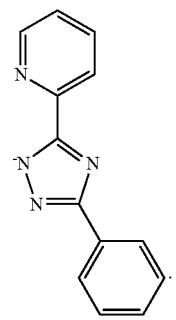

3. The organometallic complex according to claim 1, wherein the center metal is iridium.

4. A lighting apparatus comprising a light-emitting element, wherein the light-emitting element includes the organometallic complex according to claim 1.

5. A light-emitting element including the organometallic complex according to claim 1.

6. A light-emitting device including the light-emitting element according to claim 5.

7. An electronic device including the light-emitting element according to claim 5.

8. An organometallic complex comprising a structure represented by a general formula (G11):

(G11) 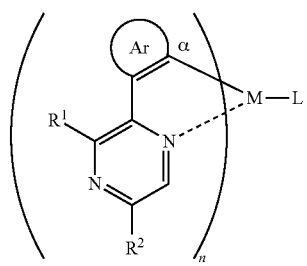

(G7) 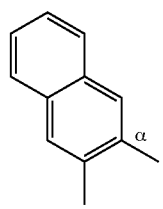

(G8)

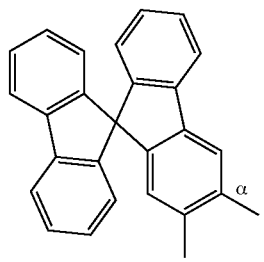

(G9)

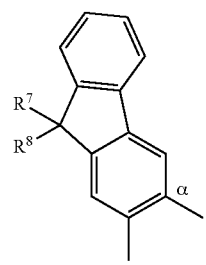

wherein R¹ represents an alkyl group having 1 to 4 carbon atoms; R² represents any one of hydrogen and an alkyl group having 1 to 4 carbon atoms; Ar represents any one of formulas (G7) to (G9); R⁷ and R⁸ each represent an alkyl group having 1 to 4 carbon atoms; M is a center metal selected from Group 9 element; α represents a position of carbon which bonds the center metal in the arylene group; L represents a monoanionic ligand; and n is 2;

wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

9. The organometallic complex according to claim 8, wherein the monoanionic ligand is represented by any one of (L1) to (L8)

(L1)

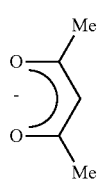

(L2)

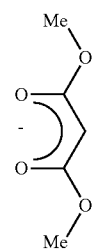

(L3)

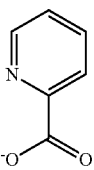

(L4)

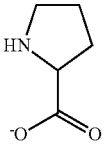

(L5)

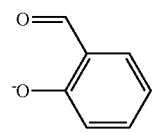

(L6)

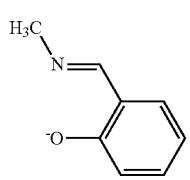

(L7)

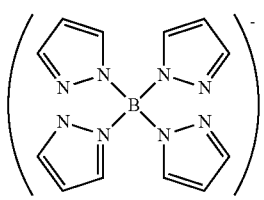

(L8)

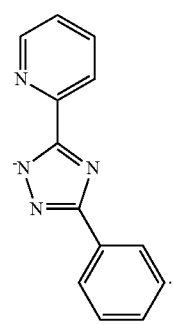

10. The organometallic complex according to claim 8, wherein the center metal is iridium.

11. A lighting apparatus comprising a light-emitting element,
    wherein the light-emitting element includes the organometallic complex according to claim 8.

12. A light-emitting element including the organometallic complex according to claim 8.

13. A light-emitting device including the light-emitting element according to claim 12.

14. An electronic device including the light-emitting element according to claim 12.

15. An organometallic complex comprising a structure represented by a general formula (G12):

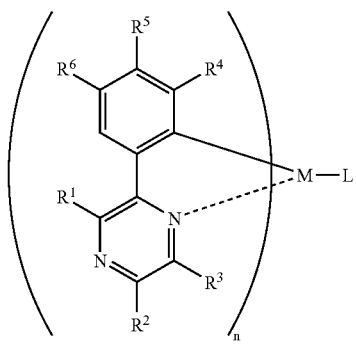

(G12)

wherein $R^1$ represents an alkyl group having 1 to 4 carbon atoms; $R^2$ and $R^3$ each represent any one of hydrogen and an alkyl group having 1 to 4 carbon atoms; $R^4$ to $R^6$ each represent a hydrogen or an electron-donating group selected from the group consisting of an unsubstituted alkyl group having 1 to 4 carbon atoms, an alkoxy group having 1 to 4 carbon atoms, a dialkylamino group having 2 to 8 carbon atoms, or a diarylamino group having 12 to 24 carbon atoms;

M is a center metal selected from Group 9 element; L represents a monoanionic ligand; and n is 2;

wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

16. The organometallic complex according to claim 15, wherein the monoanionic ligand is represented by any one of (L1) to (L8)

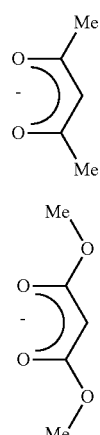

(L1)

(L2)

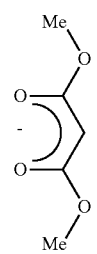

(L3)

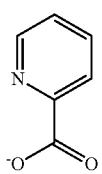

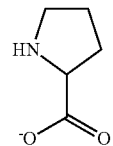

(L4)

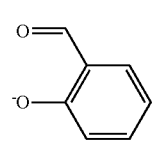

(L5)

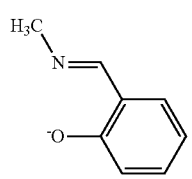

(L6)

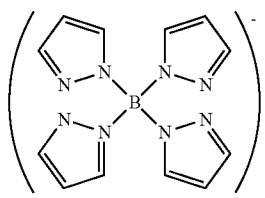

(L7)

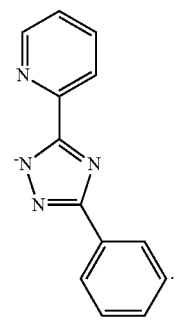

(L8)

17. The organometallic complex according to claim 15, wherein the center metal is iridium.

18. A lighting apparatus comprising a light-emitting element,
wherein the light-emitting element includes the organometallic complex according to claim 15.

19. A light-emitting element including the organometallic complex according to claim 15.

20. A light-emitting device including the light-emitting element according to claim 19.

21. An electronic device including the light-emitting element according to claim 19.

22. An organometallic complex comprising a structure represented by a general formula (G13):

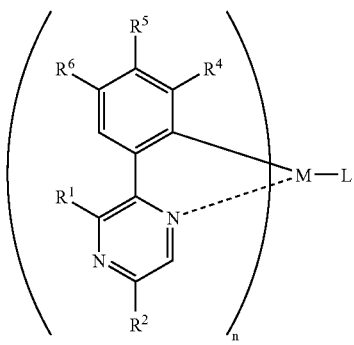
(G13)

wherein $R^1$ represents an alkyl group having 1 to 4 carbon atoms; $R^2$ represents any one of hydrogen and an alkyl group having 1 to 4 carbon atoms; $R^4$ to $R^6$ each represent a hydrogen or an electron-donating group selected from the group consisting of an unsubstituted alkyl group having 1 to 4 carbon atoms, an alkoxy group having 1 to 4 carbon atoms, a dialkylamino group having 2 to 8 carbon atoms, or a diarylamino group having 12 to 24 carbon atoms;

M is a center metal selected from Group 9 element; L represents a monoanionic ligand; and n is 2;

wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

23. The organometallic complex according to claim 22, wherein the monoanionic ligand is represented by any one of (L1) to (L8)

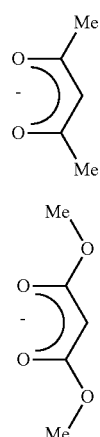
(L1)

(L2)

(L3)

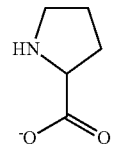
(L4)

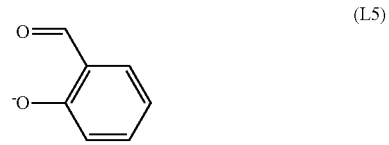
(L5)

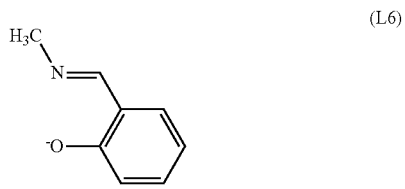
(L6)

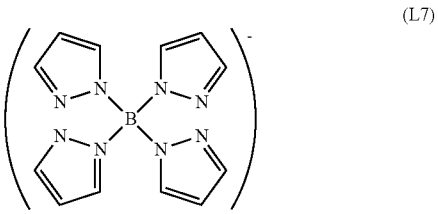
(L7)

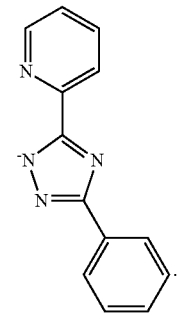
(L8)

24. The organometallic complex according to claim 22, wherein the center metal is iridium.

25. A lighting apparatus comprising a light-emitting element,
wherein the light-emitting element includes the organometallic complex according to claim 22.

26. A light-emitting element including the organometallic complex according to claim 22.

27. A light-emitting device including the light-emitting element according to claim 26.

28. An electronic device including the light-emitting element according to claim 26.

29. An organometallic complex comprising a structure represented by a general formula (G14):

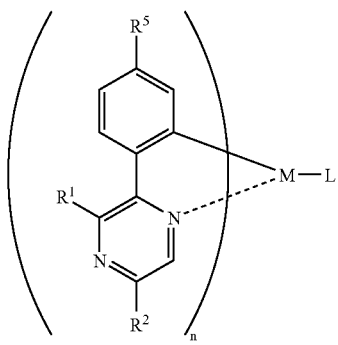
(G14)

wherein $R^1$ represents an alkyl group having 1 to 4 carbon atoms; $R^2$ represents any one of hydrogen and an alkyl group having 1 to 4 carbon atoms; $R^5$ represents a hydrogen or an electron-donating group selected from the group consisting of an unsubstituted alkyl group having 1 to 4 carbon atoms, an alkoxy group having 1 to 4 carbon atoms, a dialkylamino group having 2 to 8 carbon atoms, or a diarylamino group having 12 to 24 carbon atoms;

M is a center metal selected from Group 9 element; L represents a monoanionic ligand; and n is 2;

wherein the monoanionic ligand is any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

30. The organometallic complex according to claim 29, wherein the monoanionic ligand is represented by any one of (L1) to (L8)

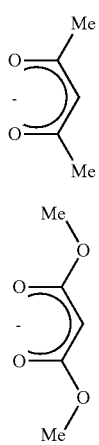
(L2)

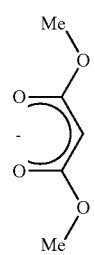
(L3)

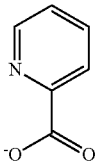
(L3)

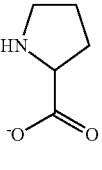
(L4)

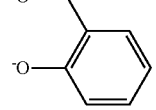
(L5)

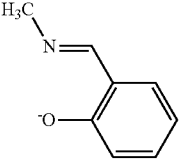
(L6)

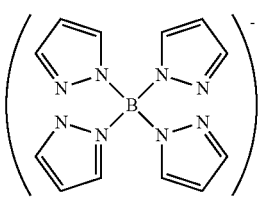
(L7)

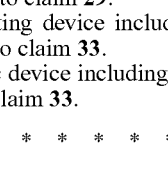
(L8)

31. The organometallic complex according to claim 29, wherein the center metal is iridium.

32. A lighting apparatus comprising a light-emitting element,
wherein the light-emitting element includes the organometallic complex according to claim 29.

33. A light-emitting element including the organometallic complex according to claim 29.

34. A light-emitting device including the light-emitting element according to claim 33.

35. An electronic device including the light-emitting element according to claim 33.

* * * * *